(12) United States Patent
Xing

(10) Patent No.: US 10,920,281 B2
(45) Date of Patent: Feb. 16, 2021

(54) RASAL1 IS A MAJOR TUMOR SUPPRESSOR GENE IN THYROID CANCER

(71) Applicant: THE JOHNS HOPKINS UNIVERSITY, Baltimore, MD (US)

(72) Inventor: Michael MingZhao Xing, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 147 days.

(21) Appl. No.: 15/967,824

(22) Filed: May 1, 2018

(65) Prior Publication Data

US 2018/0274042 A1  Sep. 27, 2018

Related U.S. Application Data

(62) Division of application No. 14/909,590, filed as application No. PCT/US2014/049535 on Aug. 4, 2014, now Pat. No. 10,047,402.

(60) Provisional application No. 61/861,822, filed on Aug. 2, 2013.

(51) Int. Cl.
  *C12Q 1/68*  (2018.01)
  *C12Q 1/6886*  (2018.01)
  *A61K 38/17*  (2006.01)

(52) U.S. Cl.
  CPC ........ *C12Q 1/6886* (2013.01); *A61K 38/1709* (2013.01); *C12Q 1/68* (2013.01); *C12Q 2600/118* (2013.01); *C12Q 2600/154* (2013.01); *C12Q 2600/156* (2013.01)

(58) Field of Classification Search
  None
  See application file for complete search history.

(56) References Cited

PUBLICATIONS

Liu D, Yang C, Bojdani E, Murugan AK, Xing M. Identification of RASAL1 as a Major Tumor Suppressor Gene in Thyroid Cancer. J Natl Cancer Inst. 2013; 105(21):1617-1627. (Year: 2013).*
Jin H et al. Epigenetic silencing of a Ca2-regulated Ras GTPase-activating protein RASAL defines a new mechanism of Ras activation in human cancers. PNAS Jul. 24, 2007 vol. 104 No. 30 12353-12358 (Year: 2007).*
Allen M, Chua S, Brillb S, Stotlera C, Bucklera A. Restricted tissue expression pattern of a novel human rasGAP-relatedgene and its murine ortholog. Gene 218 (1998) 17-25 (Year: 1998).*
Seto M et al. Reduced expression of RAS protein activator like-1 in gastric cancer. Int. J. Cancer: 128, 1293-1302 (2011) (Year: 2011).*
Chen H, Yang XW, Zhang H, Yang Q, Wang Z, Liu Y, Lu FL, Zhou BY, Qiu-Xi CH, Lu SL. In vivo and in vitro expression of the RASAL1 gene in human gastric adenocarcinoma and its clinicopathological significance. Oncol Lett. 2012;3:535-40. (Year: 2012).*
Derks S, Lentjesa MHFM, Hellebrekersa DMEI, de Bruïnea AP, Hermanb JG and van Engeland M. Methylation-specific PCR unraveled. Cellular Oncology 26 (2004) 291-299. (Year: 2004).*
Choi MR et al. Gene expression during long-term culture of mesenchymal stem cells obtained from patients with amyotrophic lateral sclerosis. BioChip J. (2012) 6(4): 342-353 (Year: 2012).*
Liu D, Yang C, Bojdani E, Murugan AK, Xing M. Identification of RASAL1 as a Major Tumor Suppressor Gene in Thyroid Cancer. J Natl Cancer Inst. 2013; 105(21):1617-1627. Supplementary Information. (Year: 2013).*
Pai et al. A Genome-Wide Study of DNA Methylation Patterns and Gene Expression Levels in Multiple Human and Chimpanzee Tissues. PLoS Genetics;2011;7;2: e1001316. (Year: 2011).*
Zhang et al. Functional DNA methylation differences between tissues, cell types, and across individuals discovered using the M&M algorithm. Genome Res;Jun. 2013;23;9:1522-1540. (Year: 2013).*
Liu D, Hu S, Hou P, Jiang D, Condouris S, Xing M. Suppression of BRAF/MEK/MAP kinase pathway restores expression of iodide-metabolizing genes in thyroid cells expressing the V600E BRAF mutant. Clin Cancer Res;Feb. 15, 2007;13(4):1341-9. (Year: 2007).*
Rebollo et al. Ras proteins: recent advances and new functions. Blood. 1999;94 (9):2971-2980.
Vigil et al. Ras superfamily GEFs and GAPs: validated and tractable targets for cancer therapy? Nat Rev Cancer. 2010;10 (12):842-857.
Kolfschoten et al. A genetic screen identifies PITX1 as a suppressor of RAS activity and tumorigenicity. Cell. 2005;121 (6):849-858.
Jin et al. Epigenetic silencing of a Ca(2+)-regulated Ras GTPase-activating protein RASAL defines a new mechanism of Ras activation in human cancers. Proc Natl Aced Sci USA. 2007;104 (30):12353-12358.
Ohta et al. Decreased expression of the RAS-GTPase activating protein RASALI is associated with colorectal tumor progression. Gastroenterology. 2009; 136 (1):206-216.
Yohay. The genetic and molecular pathogenesis of NFI and NF2. Semin Pediatr Neurol. 2006; 13 (1):21-26.
Johannessen et al. The NF1 tumor suppressor critically regulates TSC2 and mTOR. Proc Natl Acad Sci USA. 2005;102 (24):8573-8578.

(Continued)

*Primary Examiner* — Juliet C Switzer
*Assistant Examiner* — Wahwah T Johnson
(74) *Attorney, Agent, or Firm* — Johns Hopkins Technology Ventures

(57) ABSTRACT

The present invention relates to the field of cancer. More specifically, the present invention provides methods and compositions useful for treating thyroid cancer. In certain embodiments, the method comprises the steps of (a) treating DNA isolated from a sample collected from the patient using bisulfate; (b) measuring the DNA methylation level of the promoter region of the RASAL1 gene from the bisulfate-treated DNA using methylation-specific polymerase chain reaction (MSP), wherein the MSP creates a methylation and unmethylation band; (c) normalizing the measured DNA methylation level using an internal reference gene; (d) calculating the percentage of allelic methylation using the formula $[M/(M+U) \times 100\%]$, wherein M and U represent the density of the methylation and unmethylation band; and (e) predicting an increased risk of thyroid cancer in the subject if the percentage of allelic methylation is at least 40%.

2 Claims, 21 Drawing Sheets
Specification includes a Sequence Listing.

(56) References Cited

PUBLICATIONS

Viskochil. Genetics of neurofibromatosis 1 and the NF1 gene. J Child Neurol. 2002;17 (8):562-570.

Wakioka et al. Spred is a Sprouty-related suppressor of Ras signalling. Nature. 2001;412 (6847):647-651.

Sasaki et al. Identification of a dominant negative mutant of Sprouty that potentiates fibroblast growth factor—but not epidermal growth factor-induced ERK activation. J Biol Chem. 2001;276 (39):36804-36808.

Granovsky et al. Raf kinase inhibitory protein: a signal transduction modulator and metastasis suppressor. Cell Res. 2008;18 (4):452-457.

Ueda et al. Dual-specificity phosphatase 5 (DUSP5) as a direct transcriptional target of tumor suppressor p53. Oncogene. 2003;22 (36):5586-5591.

Furukawa et al. Potential tumor suppressive pathway involving DUSP6/MKP-3 in pancreatic cancer. Am J Pathol. 2003;162 (6):1807-1815.

Wrighton. Tumour suppressors: Role of nuclear PTEN revealed. Nat Rev Cancer. 2011;11 (3):154.

Hezel et al. LKB1; linking cell structure and tumor suppression. Oncogene. 2008;27 (55):6908-6919.

Van Veelen et al. The long and winding road to rational treatment of cancer associated with LKBI/AMPK/TSC/mTORC1 signaling. Oncogene. 2011. 30(20):2289-2303.

Richter et al. The RASSF proteins in cancer; from epigenetic silencing to functional characterization. Biochem Biophys Acta. 2009;1796 (2): 114-128.

Bentires-Alj et al. Stops along the RAS pathway in human genetic disease. Nat Med. 2006; 12 (3):283-285.

Brems et al. Germline loss-of-function mutations in SPRED1 cause a neurofibromatosis 1-like phenotype. Nat Genet. 2007;39 (9):1120-1126.

Jemal et al. Global cancer statistics. CA Cancer J Clin. 2011;61 (2):69-90.

Xing. Molecular pathogenesis and mechanisms of thyroid cancer. Nat Rev Cancer. 2013;13 (3):184-199.

Xing. BRAF mutation in thyroid cancer. Endocr Relat Cancer. 2005;12 (2):245-262.

Xing. BRAF mutation in papillary thyroid cancer: pathogenic role, molecular bases, and clinical implications. Endocr Rev. 2007;28 (7):742-762.

Xing. Genetic alterations in the phosphatidylinositol-3 kinase/Akt pathway in throid cancer. Thyroid. 2010;20 (7):697-706.

Hou et al. Genetic alterations and their relationship in the phosphatidylinositol 3-kinase/Akt pathway in thyroid cancer. Clin Cancer Res. 2007;13 (4):1161-1170.

Xing et al. Early occurrence of RASSF1A hypermethylation and its mutual exclusion with BRAF mutation in thyroid tumorigenesis. Cancer Res. 2004;64 (5):1664-1668.

Ishizaka et al. eDNA cloning and characterization of ret activated in a human papillary thyroid carcinoma cell line. Biochem Biophys Res Commun. 1990;168 (2):402-408.

Shapira et al. The tumor suppressor neurofibromin confers sensitivity to apoptosis by Ras-dependent and Ras-Independent pathways. Cell Death Differ. 2007;14 (5):895-906.

Nur-E-Kamal et al. The GTPase-activating NF1 fragment of 91 amino acids reverses v-Ha-Ras-induced malignant phenotype. J Biol Chem. 1993;268 (30):22331-22337.

Gutmann et al. The neurofibromatosis type 1 gene and its protein product, neurofibromin. Neuron. 1993;10(3):335-343.

Nucera et al. B-Raf(V600E) and thrombospondin-1 promote thyroid cancer progression. Proc Natl Acad Sci USA. 2010; 107(23): 10649-10654.

Chakravarty et al. Small-molecule MAPK inhibitors restore radioiodine incorporation in mouse thyroid cancers with conditional BRAF activation. J Clin Invest. 2011;121 (12):4700-4711.

Hu et al. Association of aberrant methylation of tumor suppressor genes with tumor aggressiveness and BRAF mutation in papillary thyroid cancer. Int J Cancer. 2006; 119 (10):2322-2329.

Todorova et al. Large majority of single-nucleotide mutations along the dystrophin gene can be explained by more than one mechanism of mutagenesis. Hum Mutat. 1997;9 (6):537-547.

Liu et al. Genetic alterations in the phosphoinositide 3-kinase/Akt signaling pathway confer sensitivity of thyroid cancer cells to therapeutic targeting of Akt and mammalian target of rapamycin. Cancer Res. 2009;69 (18):7311-7319.

Liu et al. Suppression of BRAF/MEK/MAP kinase pathway restores expression of iodide-metabolizing genes in thyroid cells expressing the V600E BRAF mutant. Clin Cancer Res. 2007;13 (4):1341-1349.

Chen, H., et al., "In vivo and in vitro expression of the RASAL1 gene in human gastric adenocarcinoma and its clinicopathological significance" Oncology Letters (2012) vol. 3, pp. 535-540.

Jin, H., et al., "Epigenetic silencing of a Ca2+-regulated Ras GTPase-activating protein RASAL defines a new mechanism of Ras activation in human cancers" PNAS (2007) vol. 104, No. 30, pp. 12353-12358.

Liu, D., et al., "Identification of RASAL1 as a Major Tumor Suppressor Gene in Thyroid Cancer" J Natl Cancer Inst (2013) vol. 105, pp. 1617-1627.

Concolino, P., et al., "The Unsolved Enigma of CDH1 Down-Regulation in Hereditary Diffuse Gastric Cancer" (2004) Journal of Surgical Research 121, 50-55.

Qiao, F., et al. "Enforced expression of RASAL1 suppresses cell proliferation and the transformation ability of gastric cancer cells" Oncology Reports (2012) vol. 28, pp. 1475-1481.

Seto, M., et al., "Reduced expression of RAS protein activator like-1 in gastric cancer" Int. J. Cancer (2011) vol. 128, pp. 1293-1302.

* cited by examiner

SEQUENCE LISTING

```
<160> NUMBER OF SEQ ID NOS: 86

<210> SEQ ID NO 1
<211> LENGTH: 15
<212> TYPE: DNA
<213> ORGANISM: Homo sapiens

<400> SEQUENCE: 1
cgttctaact ccctg                                                    15

<210> SEQ ID NO 2
<211> LENGTH: 14
<212> TYPE: DNA
<213> ORGANISM: Homo sapiens

<400> SEQUENCE: 2
tggatccctg caag                                                     14

<210> SEQ ID NO 3
<211> LENGTH: 16
<212> TYPE: DNA
<213> ORGANISM: Homo sapiens

<400> SEQUENCE: 3
tcaaaggcgc actctc                                                   16

<210> SEQ ID NO 4
<211> LENGTH: 15
<212> TYPE: DNA
<213> ORGANISM: Homo sapiens

<400> SEQUENCE: 4
ctgcccgccc gccat                                                    15
```

```
<210> SEQ ID NO 5
<211> LENGTH: 15
<212> TYPE: DNA
<213> ORGANISM: Homo sapiens

<400> SEQUENCE: 5
gccatgcgcc tcgcc                                                    15

<210> SEQ ID NO 6
<211> LENGTH: 15
<212> TYPE: DNA
<213> ORGANISM: Homo sapiens

<400> SEQUENCE: 6
gccatgcgcc tcgcc                                                    15

<210> SEQ ID NO 7
<211> LENGTH: 14
<212> TYPE: DNA
<213> ORGANISM: Homo sapiens

<400> SEQUENCE: 7
cgattcttcg cacc                                                     14

<210> SEQ ID NO 8
<211> LENGTH: 15
<212> TYPE: DNA
<213> ORGANISM: Homo sapiens

<400> SEQUENCE: 8
acgtctggct cagcg                                                    15

<210> SEQ ID NO 9
<211> LENGTH: 20
<212> TYPE: DNA
<213> ORGANISM: Artificial Sequence
<220> FEATURE:
<223> OTHER INFORMATION: Forward primer for RASAL1

<400> SEQUENCE: 9
gtggatgtgg atgggatga                                                20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for RASAL1

<400> SEQUENCE: 10
ttcttgcact ggaggtaggt                                               20

<210> SEQ ID NO 11
<211> LENGTH: 20
<212> TYPE: DNA
<213> ORGANISM: Artificial Sequence
<220> FEATURE:
<223> OTHER INFORMATION: Forward primer for DAB2IP

<400> SEQUENCE: 11
catggaggaa gaggtggtca                                               20

<210> SEQ ID NO 12
<211> LENGTH: 20
<212> TYPE: DNA
```

```
<213> ORGANISM: Artificial Sequence
<220> FEATURE:
<223> OTHER INFORMATION: Reverse primer for DAB2IP

<400> SEQUENCE: 12
aggtacttct tcttggctgg                                            20

<210> SEQ ID NO 13
<211> LENGTH: 20
<212> TYPE: DNA
<213> ORGANISM: Artificial Sequence
<220> FEATURE:
<223> OTHER INFORMATION: Forward primer for NF1

<400> SEQUENCE: 13
tggcactgca agcaaatgga                                            20

<210> SEQ ID NO 14
<211> LENGTH: 20
<212> TYPE: DNA
<213> ORGANISM: Artificial Sequence
<220> FEATURE:
<223> OTHER INFORMATION: Reverse primer for NF1

<400> SEQUENCE: 14
taggccacgc tctgtgtatt                                            20

<210> SEQ ID NO 15
<211> LENGTH: 20
<212> TYPE: DNA
<213> ORGANISM: Artificial Sequence
<220> FEATURE:
<223> OTHER INFORMATION: Forward primer for SPRED1

<400> SEQUENCE: 15
gatgactcaa gtggtggatg                                            20

<210> SEQ ID NO 16
<211> LENGTH: 20
<212> TYPE: DNA
<213> ORGANISM: Artificial Sequence
<220> FEATURE:
<223> OTHER INFORMATION: Reverse primer for SPRED1

<400> SEQUENCE: 16
cctctatcaa aagccctagc                                            20

<210> SEQ ID NO 17
<211> LENGTH: 20
<212> TYPE: DNA
<213> ORGANISM: Artificial Sequence
<220> FEATURE:
<223> OTHER INFORMATION: Forward primer for SPRED2

<400> SEQUENCE: 17
tcatccatgg tgaacgacag                                            20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for SPRED2

<400> SEQUENCE: 18
atggatggtg gaagatgacg                                            20
```

<210> SEQ ID NO 19
<211> LENGTH: 20
<212> TYPE: DNA
<213> ORGANISM: Artificial Sequence
<220> FEATURE:
<223> OTHER INFORMATION: Forward primer for SPRY1

<400> SEQUENCE: 19
tccactgatt gccagaactc                                               20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for SPRY1

<400> SEQUENCE: 20
ttcttgtctt ggtgctgtcc                                               20

<210> SEQ ID NO 21
<211> LENGTH: 20
<212> TYPE: DNA
<213> ORGANISM: Artificial Sequence
<220> FEATURE:
<223> OTHER INFORMATION: Forward primer for SPRY2

<400> SEQUENCE: 21
ttggtgcaaa gccgcgatca                                               20

<210> SEQ ID NO 22
<211> LENGTH: 20
<212> TYPE: DNA
<213> ORGANISM: Artificial Sequence
<220> FEATURE:
<223> OTHER INFORMATION: Reverse primer for SPRY2

<400> SEQUENCE: 22
ttggtgtttc ggatggctct                                               20

<210> SEQ ID NO 23
<211> LENGTH: 20
<212> TYPE: DNA
<213> ORGANISM: Artificial Sequence
<220> FEATURE:
<223> OTHER INFORMATION: Forward primer for RKIP

<400> SEQUENCE: 23
gcccacccag gttaagaata                                               20

<210> SEQ ID NO 24
<211> LENGTH: 20
<212> TYPE: DNA
<213> ORGANISM: Artificial Sequence
<220> FEATURE:
<223> OTHER INFORMATION: Reverse primer for RKIP

<400> SEQUENCE: 24
ctcgtaaacc agccagacat                                               20

<210> SEQ ID NO 25
<211> LENGTH: 20
<212> TYPE: DNA
<213> ORGANISM: Artificial Sequence
<220> FEATURE:

<223> OTHER INFORMATION: Forward primer for DUSP5

<400> SEQUENCE: 25
cttcctcaaa gggggatatg                                           20

<210> SEQ ID NO 26
<211> LENGTH: 20
<212> TYPE: DNA
<213> ORGANISM: Artificial Sequence
<220> FEATURE:
<223> OTHER INFORMATION: Reverse primer for DUSP5

<400> SEQUENCE: 26
tcgcacttgg atgcatggta                                           20

<210> SEQ ID NO 27
<211> LENGTH: 20
<212> TYPE: DNA
<213> ORGANISM: Artificial Sequence
<220> FEATURE:
<223> OTHER INFORMATION: Forward primer for DUSP6

<400> SEQUENCE: 27
agcgactgga acgagaatac                                           20

<210> SEQ ID NO 28
<211> LENGTH: 20
<212> TYPE: DNA
<213> ORGANISM: Artificial Sequence
<220> FEATURE:
<223> OTHER INFORMATION: Reverse primer for DUSP6

<400> SEQUENCE: 28
cgatgtccga ggaagagtca                                           20

<210> SEQ ID NO 29
<211> LENGTH: 20
<212> TYPE: DNA
<213> ORGANISM: Artificial Sequence
<220> FEATURE:
<223> OTHER INFORMATION: Forward primer for TSC1

<400> SEQUENCE: 29
caacaagcaa atgtcgggga                                           20

<210> SEQ ID NO 30
<211> LENGTH: 20
<212> TYPE: DNA
<213> ORGANISM: Artificial Sequence
<220> FEATURE:
<223> OTHER INFORMATION: Reverse primer for TSC1

<400> SEQUENCE: 30
aggatggata aacgagtggc                                           20

<210> SEQ ID NO 31
<211> LENGTH: 20
<212> TYPE: DNA
<213> ORGANISM: Artificial Sequence
<220> FEATURE:
<223> OTHER INFORMATION: Forward primer for TSC2

<400> SEQUENCE: 31
tgttggcttg tcctcggaat                                           20

```
<210> SEQ ID NO 32
<211> LENGTH: 20
<212> TYPE: DNA
<213> ORGANISM: Artificial Sequence
<220> FEATURE:
<223> OTHER INFORMATION: Reverse primer for TSC2

<400> SEQUENCE: 32
caggcagttg tagcagacca                                               20

<210> SEQ ID NO 33
<211> LENGTH: 20
<212> TYPE: DNA
<213> ORGANISM: Artificial Sequence
<220> FEATURE:
<223> OTHER INFORMATION: Forward primer for LKB1

<400> SEQUENCE: 33
atggacacgt tcatccaccg                                               20

<210> SEQ ID NO 34
<211> LENGTH: 20
<212> TYPE: DNA
<213> ORGANISM: Artificial Sequence
<220> FEATURE:
<223> OTHER INFORMATION: Reverse primer for LKB1

<400> SEQUENCE: 34
gccgtaacct cctcagtagt                                               20

<210> SEQ ID NO 35
<211> LENGTH: 23
<212> TYPE: DNA
<213> ORGANISM: Artificial Sequence
<220> FEATURE:
<223> OTHER INFORMATION: MSP forward methylation primer for RASAL1

<400> SEQUENCE: 35
gtttttattt gtagagttcg gac                                           23

<210> SEQ ID NO 36
<211> LENGTH: 20
<212> TYPE: DNA
<213> ORGANISM: Artificial Sequence
<220> FEATURE:
<223> OTHER INFORMATION: MSP reverse methylation primer for RASAL1

<400> SEQUENCE: 36
atcccaatac cgcctatccg                                               20

<210> SEQ ID NO 37
<211> LENGTH: 24
<212> TYPE: DNA
<213> ORGANISM: Artificial Sequence
<220> FEATURE:
<223> OTHER INFORMATION: MSP forward unmethylation primer for RASAL1

<400> SEQUENCE: 37
ggtttttatt tgtagagttt ggat                                          24

<210> SEQ ID NO 38
<211> LENGTH: 21
<212> TYPE: DNA
<213> ORGANISM: Artificial Sequence
<220> FEATURE:
<223> OTHER INFORMATION: MSP reverse unmethylation primer for RASAL1
```

<400> SEQUENCE: 38
aatcccaata ccacctatcc a                                              21

<210> SEQ ID NO 39
<211> LENGTH: 22
<212> TYPE: DNA
<213> ORGANISM: Artificial Sequence
<220> FEATURE:
<223> OTHER INFORMATION: Forward primer for RASAL1 Exon2

<400> SEQUENCE: 39
tgaagcaggt gacatgtaga cg                                             22

<210> SEQ ID NO 40
<211> LENGTH: 21
<212> TYPE: DNA
<213> ORGANISM: Artificial Sequence
<220> FEATURE:
<223> OTHER INFORMATION: Reverse primer for RASAL1 Exon2

<400> SEQUENCE: 40
gggcatctgc taactctagg c                                              21

<210> SEQ ID NO 41
<211> LENGTH: 21
<212> TYPE: DNA
<213> ORGANISM: Artificial Sequence
<220> FEATURE:
<223> OTHER INFORMATION: Forward primer for RASAL1 Exon 3

<400> SEQUENCE: 41
tatttctatg ggtggaagcc c                                              21

<210> SEQ ID NO 42
<211> LENGTH: 21
<212> TYPE: DNA
<213> ORGANISM: Artificial Sequence
<220> FEATURE:
<223> OTHER INFORMATION: Reverse primer for RASAL1 Exon 3

<400> SEQUENCE: 42
aattcttggt cccagattcc c                                              21

<210> SEQ ID NO 43
<211> LENGTH: 21
<212> TYPE: DNA
<213> ORGANISM: Artificial Sequence
<220> FEATURE:
<223> OTHER INFORMATION: Forward primer for RASAL1 Exon 4

<400> SEQUENCE: 43
gtgtctgggt ctccaggtgt c                                              21

<210> SEQ ID NO 44
<211> LENGTH: 21
<212> TYPE: DNA
<213> ORGANISM: Artificial Sequence
<220> FEATURE:
<223> OTHER INFORMATION: Reverse primer for RASAL1 Exon 4

<400> SEQUENCE: 44
acgtgaaggt ctgagtcagg g                                              21

<210> SEQ ID NO 45
<211> LENGTH: 20

```
<212> TYPE: DNA
<213> ORGANISM: Artificial Sequence
<220> FEATURE:
<223> OTHER INFORMATION: Forward primer for RASAL1 Exon 5

<400> SEQUENCE: 45
cacccagacc ttgacacctg                                              20

<210> SEQ ID NO 46
<211> LENGTH: 21
<212> TYPE: DNA
<213> ORGANISM: Artificial Sequence
<220> FEATURE:
<223> OTHER INFORMATION: Reverse primer for RASAL1 Exon 5

<400> SEQUENCE: 46
tatgatagca ccaccgcact c                                            21

<210> SEQ ID NO 47
<211> LENGTH: 20
<212> TYPE: DNA
<213> ORGANISM: Artificial Sequence
<220> FEATURE:
<223> OTHER INFORMATION: Forward primer for RASAL1 Exon 6

<400> SEQUENCE: 47
caacagaacc agaccctgtg                                              20

<210> SEQ ID NO 48
<211> LENGTH: 20
<212> TYPE: DNA
<213> ORGANISM: Artificial Sequence
<220> FEATURE:
<223> OTHER INFORMATION: Reverse primer for RASAL1 Exon 6

<400> SEQUENCE: 48
ggactgagga ggtcccaaac                                              20

<210> SEQ ID NO 49
<211> LENGTH: 21
<212> TYPE: DNA
<213> ORGANISM: Artificial Sequence
<220> FEATURE:
<223> OTHER INFORMATION: Forward primer for RASAL1 Exon 7

<400> SEQUENCE: 49
gtttggacgg tcatggttag g                                            21

<210> SEQ ID NO 50
<211> LENGTH: 21
<212> TYPE: DNA
<213> ORGANISM: Artificial Sequence
<220> FEATURE:
<223> OTHER INFORMATION: Reverse primer for RASAL1 Exon 7

<400> SEQUENCE: 50
ggaagcgagt cttcttgatg g                                            21

<210> SEQ ID NO 51
<211> LENGTH: 21
<212> TYPE: DNA
<213> ORGANISM: Artificial Sequence
<220> FEATURE:
<223> OTHER INFORMATION: Forward primer for RASAL1 Exon 8

<400> SEQUENCE: 51
```
cagagcttgg agacctcagt g         21

<210> SEQ ID NO 52
<211> LENGTH: 21
<212> TYPE: DNA
<213> ORGANISM: Artificial Sequence
<220> FEATURE:
<223> OTHER INFORMATION: Reverse primer for RASAL1 Exon 8

<400> SEQUENCE: 52
gctgtacatc caccttctg a          21

<210> SEQ ID NO 53
<211> LENGTH: 21
<212> TYPE: DNA
<213> ORGANISM: Artificial Sequence
<220> FEATURE:
<223> OTHER INFORMATION: Forward primer for RASAL1 Exon 9

<400> SEQUENCE: 53
ctgttcttcc agggctaggt g         21

<210> SEQ ID NO 54
<211> LENGTH: 22
<212> TYPE: DNA
<213> ORGANISM: Artificial Sequence
<220> FEATURE:
<223> OTHER INFORMATION: Reverse primer for RASAL1 Exon 9

<400> SEQUENCE: 54
ggtgaacggg tgtaaagtga ac        22

<210> SEQ ID NO 55
<211> LENGTH: 20
<212> TYPE: DNA
<213> ORGANISM: Artificial Sequence
<220> FEATURE:
<223> OTHER INFORMATION: Forward primer for RASAL1 Exons 10-11

<400> SEQUENCE: 55
atcgtgttcg gccagatctt           20

<210> SEQ ID NO 56
<211> LENGTH: 20
<212> TYPE: DNA
<213> ORGANISM: Artificial Sequence
<220> FEATURE:
<223> OTHER INFORMATION: Reverse primer for RASAL1 Exons 10-11

<400> SEQUENCE: 56
tcctgcaagc ccaccattga           20

<210> SEQ ID NO 57
<211> LENGTH: 20
<212> TYPE: DNA
<213> ORGANISM: Artificial Sequence
<220> FEATURE:
<223> OTHER INFORMATION: Forward primer for RASAL1 Exons 12-13

<400> SEQUENCE: 57
gttcagctcc ctaaatccca           20

<210> SEQ ID NO 58
<211> LENGTH: 20
<212> TYPE: DNA
<213> ORGANISM: Artificial Sequence

```
<220> FEATURE:
<223> OTHER INFORMATION: Reverse primer for RASAL1 Exons 12-13

<400> SEQUENCE: 58
aggtcagggt cctcaggctt                                               20

<210> SEQ ID NO 59
<211> LENGTH: 20
<212> TYPE: DNA
<213> ORGANISM: Artificial Sequence
<220> FEATURE:
<223> OTHER INFORMATION: Forward primer for RASAL1 Exon 14

<400> SEQUENCE: 59
aagatgagtc ctctcggagc                                               20

<210> SEQ ID NO 60
<211> LENGTH: 20
<212> TYPE: DNA
<213> ORGANISM: Artificial Sequence
<220> FEATURE:
<223> OTHER INFORMATION: Reverse primer for RASAL1 Exon 14

<400> SEQUENCE: 60
cagttctgtc ctgactcctc                                               20

<210> SEQ ID NO 61
<211> LENGTH: 20
<212> TYPE: DNA
<213> ORGANISM: Artificial Sequence
<220> FEATURE:
<223> OTHER INFORMATION: Forward primer for RASAL1 Exon 15

<400> SEQUENCE: 61
tgtggcttcc tggtcaattc                                               20

<210> SEQ ID NO 62
<211> LENGTH: 20
<212> TYPE: DNA
<213> ORGANISM: Artificial Sequence
<220> FEATURE:
<223> OTHER INFORMATION: Reverse primer for RASAL1 Exon 15

<400> SEQUENCE: 62
gctctgctcc taccatgctt                                               20

<210> SEQ ID NO 63
<211> LENGTH: 20
<212> TYPE: DNA
<213> ORGANISM: Artificial Sequence
<220> FEATURE:
<223> OTHER INFORMATION: Forward primer for RASAL1 Exon 16

<400> SEQUENCE: 63
tgcccggcaa tatgagtctt                                               20

<210> SEQ ID NO 64
<211> LENGTH: 20
<212> TYPE: DNA
<213> ORGANISM: Artificial Sequence
<220> FEATURE:
<223> OTHER INFORMATION: Reverse primer for RASAL1 Exon 16

<400> SEQUENCE: 64
gaagtccctg agtggtgtct                                               20
```

```
<210> SEQ ID NO 65
<211> LENGTH: 20
<212> TYPE: DNA
<213> ORGANISM: Artificial Sequence
<220> FEATURE:
<223> OTHER INFORMATION: Forward primer for RASAL1 Exon 17

<400> SEQUENCE: 65
ctaggggagc agagaaccat                                               20

<210> SEQ ID NO 66
<211> LENGTH: 20
<212> TYPE: DNA
<213> ORGANISM: Artificial Sequence
<220> FEATURE:
<223> OTHER INFORMATION: Reverse primer for RASAL1 Exon 17

<400> SEQUENCE: 66
acaaagaggc agcacactga                                               20

<210> SEQ ID NO 67
<211> LENGTH: 20
<212> TYPE: DNA
<213> ORGANISM: Artificial Sequence
<220> FEATURE:
<223> OTHER INFORMATION: Forward primer for RASAL1 Exon 18

<400> SEQUENCE: 67
atggacgagc acacagagca                                               20

<210> SEQ ID NO 68
<211> LENGTH: 19
<212> TYPE: DNA
<213> ORGANISM: Artificial Sequence
<220> FEATURE:
<223> OTHER INFORMATION: Reverse primer for RASAL1 Exon 18

<400> SEQUENCE: 68
ccatcgcggt ggggtctca                                                19

<210> SEQ ID NO 69
<211> LENGTH: 20
<212> TYPE: DNA
<213> ORGANISM: Artificial Sequence
<220> FEATURE:
<223> OTHER INFORMATION: Forward primer for RASAL1 Exon 19

<400> SEQUENCE: 69
aaggtgagac cccaccgcga                                               20

<210> SEQ ID NO 70
<211> LENGTH: 20
<212> TYPE: DNA
<213> ORGANISM: Artificial Sequence
<220> FEATURE:
<223> OTHER INFORMATION: Reverse primer for RASAL1 Exon 19

<400> SEQUENCE: 70
ccacgagata ggcactgtta                                               20

<210> SEQ ID NO 71
<211> LENGTH: 20
<212> TYPE: DNA
<213> ORGANISM: Artificial Sequence
<220> FEATURE:
<223> OTHER INFORMATION: Forward primer for RASAL1 Exon 20
```

<400> SEQUENCE: 71
agtagtaggt ttgaggaggg                                              20

<210> SEQ ID NO 72
<211> LENGTH: 20
<212> TYPE: DNA
<213> ORGANISM: Artificial Sequence
<220> FEATURE:
<223> OTHER INFORMATION: Reverse primer for RASAL1 Exon 20

<400> SEQUENCE: 72
atccaccaac acacatggga                                              20

<210> SEQ ID NO 73
<211> LENGTH: 20
<212> TYPE: DNA
<213> ORGANISM: Artificial Sequence
<220> FEATURE:
<223> OTHER INFORMATION: Forward primer for RASAL1 Exon 21

<400> SEQUENCE: 73
gtgatggtga tggttcagga                                              20

<210> SEQ ID NO 74
<211> LENGTH: 19
<212> TYPE: DNA
<213> ORGANISM: Artificial Sequence
<220> FEATURE:
<223> OTHER INFORMATION: Reverse primer for RASAL1 Exon 21

<400> SEQUENCE: 74
tgggctcaag caattctca                                               19

<210> SEQ ID NO 75
<211> LENGTH: 21
<212> TYPE: DNA
<213> ORGANISM: Artificial Sequence
<220> FEATURE:
<223> OTHER INFORMATION: Forward primer for RASAL1 Exon 22

<400> SEQUENCE: 75
agcatgagaa accattgggt c                                            21

<210> SEQ ID NO 76
<211> LENGTH: 21
<212> TYPE: DNA
<213> ORGANISM: Artificial Sequence
<220> FEATURE:
<223> OTHER INFORMATION: Reverse primer for RASAL1 Exon 22

<400> SEQUENCE: 76
gactaggcac gtctctggga g                                            21

<210> SEQ ID NO 77
<211> LENGTH: 29
<212> TYPE: DNA
<213> ORGANISM: Artificial Sequence
<220> FEATURE:
<223> OTHER INFORMATION: Mutagenesis forward primer for RASAL1 N344S

<400> SEQUENCE: 77
ccctcttccg ttctagctcc ctggcatcc                                    29

<210> SEQ ID NO 78

```
<211> LENGTH: 29
<212> TYPE: DNA
<213> ORGANISM: Artificial Sequence
<220> FEATURE:
<223> OTHER INFORMATION: Mutagenesis reverse primer for RASAL1 N344S

<400> SEQUENCE: 78
ggatgccagg gagctagaac ggaagaggg                                            29

<210> SEQ ID NO 79
<211> LENGTH: 30
<212> TYPE: DNA
<213> ORGANISM: Artificial Sequence
<220> FEATURE:
<223> OTHER INFORMATION: Mutagenesis forward primer for RASAL1 P385S

<400> SEQUENCE: 79
acatggagct ggattcctgc aagatggacc                                           30

<210> SEQ ID NO 80
<211> LENGTH: 30
<212> TYPE: DNA
<213> ORGANISM: Artificial Sequence
<220> FEATURE:
<223> OTHER INFORMATION: Mutagenesis reverse primer for RASAL1 P385S

<400> SEQUENCE: 80
ggtccatctt gcaggaatcc agctccatgt                                           30

<210> SEQ ID NO 81
<211> LENGTH: 25
<212> TYPE: DNA
<213> ORGANISM: Artificial Sequence
<220> FEATURE:
<223> OTHER INFORMATION: Mutagenesis forward primer for RASAL1 R438C

<400> SEQUENCE: 81
ccgcccgcca tgtgcctcgc cttca                                                25

<210> SEQ ID NO 82
<211> LENGTH: 25
<212> TYPE: DNA
<213> ORGANISM: Artificial Sequence
<220> FEATURE:
<223> OTHER INFORMATION: Mutagenesis reverse primer for RASAL1 R438C

<400> SEQUENCE: 82
tgaaggcgag gcacatggcg ggcgg                                                25

<210> SEQ ID NO 83
<211> LENGTH: 31
<212> TYPE: DNA
<213> ORGANISM: Artificial Sequence
<220> FEATURE:
<223> OTHER INFORMATION: Mutagenesis forward primer for RASAL1 P474L

<400> SEQUENCE: 83
ctcttcttgc gattcttagc acctgccatc c                                         31

<210> SEQ ID NO 84
<211> LENGTH: 31
<212> TYPE: DNA
<213> ORGANISM: Artificial Sequence
<220> FEATURE:
<223> OTHER INFORMATION: Mutagenesis reverse primer for RASAL1 P474L

<400> SEQUENCE: 84
```

```
ggatggcagg tgctaagaat cgcaagaaga g                                       31

<210> SEQ ID NO 85
<211> LENGTH: 3841
<212> TYPE: DNA
<213> ORGANISM: Homo sapiens

<400> SEQUENCE: 85
gtgtttaact ggaaactaga acgagatgga aggggatgtt caaggcccct cccttgactc        60
tgaacggacc cccagggaac atgcgaccct ctctctggcg acgcctccca cccaccacta       120
atacttgctc ctggaccggg gggcgcgag  gttggagaga ggaggcaggt gtctgcatgc       180
tacccgggtc tcggacaggc ggcactggga ccacgaggca gggagccagg cttgaagcag       240
gtgacatgta gacgtcccct ggtccagcct cggaacctga gcgcccttct gcctggaaag       300
tttgtggcta ggcgccatgg ccaagagcag ctccctgaat gttcgcgtgg tggagggccg       360
cgcgctgcct gccaaggacg tgtctggag  cagcgacccc tactgcctag tgaaagtgga       420
cgacgaggtg gtggccagga cagctactgt ctggaggagc ctgggcccct ctgggggga       480
ggagtacacg gtgcacctgc ctctggattt ccaccagctg gccttctacg tgctggatga       540
ggacactgtc gggcacgacg acatcatcgg caagatctcg ctgagcaggg aggcgattac       600
agccgacccc cgagggattg acagctggat taacttgagc cgagtggacc cagatgcaga       660
agtgcagggt gagatctgcc tgtcagtgca gatgctggag gatgggcagg gccgctgcct       720
tcgctgccat gtgcttcagg ccagggacct ggctcccaga gacatctctg gcacatctga       780
cccatttgca cgtgtgtttt ggggcagcca gagcttggag acctcaacca tcaagaagac       840
tcgcttcccg cactgggatg aagtgctgga gctgcgggag atgccaggtg ccccgtcccc       900
actgcgggtg gagctctggg actgggacat ggtgggcaag aatgacttct gggcatggt       960
ggagttctct ccaaagaccc tccagcagaa gccacctaaa ggctggttcc gcctcctgcc      1020
ctttcccaga gccgaggagg attctggggg gaacctgggt gccctgcgag tgaaggtacg      1080
cctgattgag gaccgcgtcc tgccctccca gtgctaccag cctctcatgg agctgctcat      1140
ggagtctgtg caggggccag cagaggagga cactgctagc cccttggctt tgctggaaga      1200
gctgaccttg ggggactgcc gccaggacct tgccaccaag ctggtgaaac tctttcttgg      1260
ccggggactg gctgggcgct ttctggacta tctcacccgg cgtgaggtgg ctcggaccat      1320
ggaccccaac accctcttcc gttctaactc cctggcatcc aagtcgatgg aacagtttat      1380
gaagctcgtg ggcatgccct acctgcacga ggtcctgaag cctgtgatta gccgtgtctt      1440
tgaggagaag aagtacatgg agctggatcc ctgcaagatg gacctgggcc gcacccggag      1500
gatctccttc aaaggcgcac tctcggagga gcagatgcgg gagaccagcc tgggctgct       1560
gacgggctac ctggggccca tcgtggacgc catcgtgggc tccgtgggc  gctgccgcc       1620
cgccatgcgc ctcgccttca gcagctgca  ccggcgagtg gaggagcgct ccccccaggc      1680
cgagcaccag gatgtgaagt acctggccat cagtggattt ctcttcttgc gattcttcgc      1740
acctgccatc cttacccca  agctgtttga ccttcgggac caaacgcggg acccccagac      1800
tagccgctca ctgctgttgc ttgccaaggc tgtgcagagc attggaaacc tgggccagca      1860
gctgggccaa ggcaaggaac tgtggatggc ccccctgcac cccttcctgc tgcagtgtgt      1920
ctcacgtgtg agagacttcc tggaccggct ggtggatgtg gatggggatg aagctggtgt      1980
cccagccagg gccctggttcc cgcccctcggc cattgttcga gaaggctatc tgctgaagcg      2040
```

```
caaggaggag cctgccggcc tggccacgcg ctttgccttc aagaagcgct acgtctggct    2100
cagcggggag accctctcct tctccaagag tcctgagtgg cagatgtgtc actccatccc    2160
cgtgtctcac atccgcgccg tggagcgcgt agacgagggc gccttccaac tgccccacgt    2220
gatgcaggtg gtgacgcagg acggcacggg ggcgctgcac accacctacc tccagtgcaa    2280
gaatgtgaat gagctcaacc agtggctctc ggccttgcgc aaggccagcg cccccaaccc    2340
gaacaagctg gccgcctgcc accccggtgc cttccgcagc gcgcgctgga cctgctgcct    2400
ccaggctgag cgctcagccg ccggctgcag ccgtacacac tcagctgtca ccctggggga    2460
ctggagtgac ccactggatc ctgatgctga ggcccagaca gtgtatcggc agctgctcct    2520
ggggcgggac cagctcaggc tgaaattact ggaggattct aacatggata caactctgga    2580
ggcagacaca ggggcctgtc ctgaggtcct ggcccggcaa agagcagcaa ctgcccgcct    2640
gctggaggtg ctcgcagacc tggatcgtgc ccacgaggag ttccagcagc aggagcgagg    2700
gaaggcggcc ctgggccccc ttggcccta  aggaaatgcc agagctagcc cggaaggagg    2760
agcaagagcc agggggccct cttcagcgca tcctgccccg ggagtctcct gtctccttgg    2820
acctctttga ttctgtggtt tggaggctcc cagagacgtg cctagtcctg tgtgccttga    2880
gtccagaact cagggcatgg aagcccttg  gcaggggcca gccttgcact gagtgaaact    2940
tgccctctgg cttgattcag actggagtgg ataggataag gaacctgact tatttgactg    3000
agactggggt ctctacttca ccaaactggc ctctatccat accaaggagg ccagcctggc    3060
cctgagctgc tggatacagc tggacctgaa ttcctgatgc ccatgtgatg ttgttgcccc    3120
agatgggcac taaatggcct cactccttcc tgttttcatg tctgctaatc cctataacct    3180
cactgattct tctgtacccct gcccttggcc taggactcca accacaagct tccagaatca    3240
ggtgccctca ggaagaacca aggctgggtg ggggtccagt gtgccaaact cagacccttg    3300
gagcctggga gaccttgggc caggctgttt atctctctct gggtctcaga ttaccctgta    3360
taaaagagg  agggaaagtc tagatgtgtg gttttcaaac tggattccaa tgaggtagtt    3420
caagaacaag ggaggagttt ctctgactgt gggccaaaga ccacccgcta gaatgtctgc    3480
tagaaatgca gatttctgag gcccagccag ctactgactc agaatctgag ggtatatgaa    3540
ggcaagaatc agggttattt aacagattcc gtaggtcatt tggatgagta tcagctttga    3600
ggaccacagg cctggggaat gggcaatttt attttatttt gttttagag  ttggggtct     3660
cactctgttg cccaggctgc agtacagtgg catgatcata ggtcagtgca ccctcaaact    3720
tctggacttc agtgatcctc ccacgttagc ctccagagca gctgcgacta caggtgcaag    3780
ccatcacgcc tggctaattt ttaaatttt  gtagagatgg ggggtctcac tatgttgccc    3840
a                                                                    3841
```

<210> SEQ ID NO 86
<211> LENGTH: 804
<212> TYPE: PRT
<213> ORGANISM: Homo sapiens

<400> SEQUENCE: 86

```
Met Ala Lys Ser Ser Ser Leu Asn Val Arg Val Glu Gly Arg Ala
1               5                   10                  15

Leu Pro Ala Lys Asp Val Ser Gly Ser Ser Asp Pro Tyr Cys Leu Val
                20                  25                  30

Lys Val Asp Asp Glu Val Val Ala Arg Thr Ala Thr Val Trp Arg Ser
            35                  40                  45
```

-continued

```
Leu Gly Pro Phe Trp Gly Glu Glu Tyr Thr Val His Leu Pro Leu Asp
 50                  55                  60

Phe His Gln Leu Ala Phe Tyr Val Leu Asp Glu Asp Thr Val Gly His
 65                  70                  75                  80

Asp Asp Ile Ile Gly Lys Ile Ser Leu Ser Arg Glu Ala Ile Thr Ala
                 85                  90                  95

Asp Pro Arg Gly Ile Asp Ser Trp Ile Asn Leu Ser Arg Val Asp Pro
                100                 105                 110

Asp Ala Glu Val Gln Gly Glu Ile Cys Leu Ser Val Gln Met Leu Glu
                115                 120                 125

Asp Gly Gln Gly Arg Cys Leu Arg Cys His Val Leu Gln Ala Arg Asp
130                 135                 140

Leu Ala Pro Arg Asp Ile Ser Gly Thr Ser Asp Pro Phe Ala Arg Val
145                 150                 155                 160

Phe Trp Gly Ser Gln Ser Leu Glu Thr Ser Thr Ile Lys Lys Thr Arg
                165                 170                 175

Phe Pro His Trp Asp Glu Val Leu Glu Leu Arg Glu Met Pro Gly Ala
                180                 185                 190

Pro Ser Pro Leu Arg Val Glu Leu Trp Asp Trp Asp Met Val Gly Lys
                195                 200                 205

Asn Asp Phe Leu Gly Met Val Glu Phe Ser Pro Lys Thr Leu Gln Gln
210                 215                 220

Lys Pro Pro Lys Gly Trp Phe Arg Leu Leu Pro Phe Pro Arg Ala Glu
225                 230                 235                 240

Glu Asp Ser Gly Gly Asn Leu Gly Ala Leu Arg Val Lys Val Arg Leu
                245                 250                 255

Ile Glu Asp Arg Val Leu Pro Ser Gln Cys Tyr Gln Pro Leu Met Glu
                260                 265                 270

Leu Leu Met Glu Ser Val Gln Gly Pro Ala Glu Glu Asp Thr Ala Ser
                275                 280                 285

Pro Leu Ala Leu Leu Glu Glu Leu Thr Leu Gly Asp Cys Arg Gln Asp
290                 295                 300

Leu Ala Thr Lys Leu Val Lys Leu Phe Leu Gly Arg Gly Leu Ala Gly
305                 310                 315                 320

Arg Phe Leu Asp Tyr Leu Thr Arg Arg Glu Val Ala Arg Thr Met Asp
                325                 330                 335

Pro Asn Thr Leu Phe Arg Ser Asn Ser Leu Ala Ser Lys Ser Met Glu
                340                 345                 350

Gln Phe Met Lys Leu Val Gly Met Pro Tyr Leu His Glu Val Leu Lys
                355                 360                 365

Pro Val Ile Ser Arg Val Phe Glu Glu Lys Lys Tyr Met Glu Leu Asp
370                 375                 380

Pro Cys Lys Met Asp Leu Gly Arg Thr Arg Arg Ile Ser Phe Lys Gly
385                 390                 395                 400

Ala Leu Ser Glu Glu Gln Met Arg Glu Thr Ser Leu Gly Leu Leu Thr
                405                 410                 415

Gly Tyr Leu Gly Pro Ile Val Asp Ala Ile Val Gly Ser Val Gly Arg
                420                 425                 430

Cys Pro Pro Ala Met Arg Leu Ala Phe Lys Gln Leu His Arg Arg Val
                435                 440                 445

Glu Glu Arg Phe Pro Gln Ala Glu His Gln Asp Val Lys Tyr Leu Ala
450                 455                 460

Ile Ser Gly Phe Leu Phe Leu Arg Phe Phe Ala Pro Ala Ile Leu Thr
```

```
        465                 470                 475                 480
Pro Lys Leu Phe Asp Leu Arg Asp Gln His Ala Asp Pro Gln Thr Ser
                485                 490                 495
Arg Ser Leu Leu Leu Leu Ala Lys Ala Val Gln Ser Ile Gly Asn Leu
                500                 505                 510
Gly Gln Gln Leu Gly Gln Gly Lys Glu Leu Trp Met Ala Pro Leu His
                515                 520                 525
Pro Phe Leu Leu Gln Cys Val Ser Arg Val Arg Asp Phe Leu Asp Arg
                530                 535                 540
Leu Val Asp Val Asp Gly Asp Glu Ala Gly Val Pro Ala Arg Ala Leu
545                 550                 555                 560
Phe Pro Pro Ser Ala Ile Val Arg Glu Gly Tyr Leu Leu Lys Arg Lys
                565                 570                 575
Glu Glu Pro Ala Gly Leu Ala Thr Arg Phe Ala Phe Lys Lys Arg Tyr
                580                 585                 590
Val Trp Leu Ser Gly Glu Thr Leu Ser Phe Ser Lys Ser Pro Glu Trp
                595                 600                 605
Gln Met Cys His Ser Ile Pro Val Ser His Ile Arg Ala Val Glu Arg
                610                 615                 620
Val Asp Glu Gly Ala Phe Gln Leu Pro His Val Met Gln Val Val Thr
625                 630                 635                 640
Gln Asp Gly Thr Gly Ala Leu His Thr Thr Tyr Leu Gln Cys Lys Asn
                645                 650                 655
Val Asn Glu Leu Asn Gln Trp Leu Ser Ala Leu Arg Lys Ala Ser Ala
                660                 665                 670
Pro Asn Pro Asn Lys Leu Ala Ala Cys His Pro Gly Ala Phe Arg Ser
                675                 680                 685
Ala Arg Trp Thr Cys Cys Leu Gln Ala Glu Arg Ser Ala Gly Cys
                690                 695                 700
Ser Arg Thr His Ser Ala Val Thr Leu Gly Asp Trp Ser Asp Pro Leu
705                 710                 715                 720
Asp Pro Asp Ala Glu Ala Gln Thr Val Tyr Arg Gln Leu Leu Leu Gly
                725                 730                 735
Arg Asp Gln Leu Arg Leu Lys Leu Leu Glu Asp Ser Asn Met Asp Thr
                740                 745                 750
Thr Leu Glu Ala Asp Thr Gly Ala Cys Pro Glu Val Leu Ala Arg Gln
                755                 760                 765
Arg Ala Ala Thr Ala Arg Leu Leu Glu Val Leu Ala Asp Leu Asp Arg
770                 775                 780
Ala His Glu Glu Phe Gln Gln Gln Glu Arg Gly Lys Ala Ala Leu Gly
785                 790                 795                 800
Pro Leu Gly Pro
```

RASAL1 IS A MAJOR TUMOR SUPPRESSOR GENE IN THYROID CANCER

CROSS-REFERENCE TO RELATED APPLICATIONS

This application is a Divisional of U.S. patent application Ser. No. 14/909,590, filed Feb. 2, 2016, which is a is a 35 U.S.C. § 371 U.S. national entry of International Application PCT/US2014/049535, having an international filing date of Aug. 4, 2014, which claims the benefit of U.S. Provisional Application No. 61/861,822, filed Aug. 2, 2013; the content of each of the aforementioned applications is herein incorporated by reference in their entirety.

STATEMENT OF GOVERNMENTAL INTEREST

This invention was made with government support under grant no. R01CA134225, awarded by the National Institutes of Health. The government has certain rights in the invention.

FIELD OF THE INVENTION

The present invention relates to the field of cancer. More specifically, the present invention provides methods and compositions useful for treating thyroid cancer.

INCORPORATION-BY-REFERENCE OF MATERIAL SUBMITTED ELECTRONICALLY

This application contains a sequence listing. It has been submitted electronically via EFS-Web as an ASCII text file entitled "P12597-02_ST25.txt." The sequence listing is 29,012 bytes in size, and was created on Aug. 4, 2014. It is hereby incorporated by reference in its entirety.

BACKGROUND OF THE INVENTION

Thyroid cancer is the most common classical endocrine malignancy, and its incidence has been rising rapidly in the U.S. as well as other industrialized countries over the past few decades. Thyroid cancers are classified histologically into four groups: papillary, follicular, medullary, and undifferentiated or anaplastic thyroid carcinomas. If diagnosed at an early stage, thyroid cancer is a well manageable disease with a 5-year survival rate of 97% among all patients. Survival rate is poorer (about 40%) among individuals that are diagnosed with a more advanced disease; i.e., individuals with large, invasive tumors and/or distant metastases have a 5-year survival rate of about 40%. For radioiodine-resistant metastatic disease, there is no effective treatment and the 10-year survival rate among these patients is less than 15%.

Although relatively rare (1% of all malignancies in the US), the incidence of thyroid cancer more than doubled between 1984 and 2004 in the US. Between 1995 and 2004, thyroid cancer was the third fastest growing cancer diagnosis, behind only peritoneum, omentum, and mesentery cancers and "other" digestive cancers. Similarly, dramatic increases in thyroid cancer incidence have also been observed in Canada, Australia, Israel, and several European countries. Thus, there is a need for better understanding of the molecular causes of thyroid cancer development and progression to develop new diagnostic tools and better treatment options.

SUMMARY OF THE INVENTION

The present invention is based, at least in part, on the discovery of RASAL1 as a major tumor suppressor gene that is frequently inactivated by hypermethylation and mutations, providing a novel alternative genetic background in thyroid cancer. Of particular excitement is that the present inventors, for the first time, identified several common inactivating mutations in this gene and definitively demonstrated the tumor-suppressing activities of RASAL1 and its inactivation by the mutations. The present inventors also defined the important role of RASAL1 in the regulation of the RAS-coupled MAPK and PI3K pathways and its mutually exclusive relationship with classical genetic alterations in these signaling pathways. These data for the first time unequivocally establish RASAL1 as a prominent human tumor suppressor gene. These findings have significant clinical implications: 1) Aberrant methylation and mutations in the RASAL1 gene can be useful diagnostic molecular markers for human cancers, such as thyroid cancer; 2) Aberrant methylation and mutations in the RASAL1 gene can be useful prognostic molecular markers for human cancers, such as thyroid cancer, to predict tumor behavior and clinicopathological outcomes of cancers and help with their risk stratification and optimal management; 3) RASAL1 and its coupled signaling pathways can be novel therapeutic target for human cancers—for example, restoration of the deficient RASAL1 system may be therapeutic for cancers as guided by the methylation and mutation status of this gene. The aberrant methylation and mutations of RASAL1 identified herein may prove to be also present in other human diseases, including non-cancer diseases, and can be similarly used to help the diagnosis, prognostication, risk assessment and optimal management of such diseases.

As described herein, the diagnostic and prognostic value of RASAL1 as mutations and hypermethylation occurred in thyroid cancer, particularly aggressive types of cancer, but not in benign thyroid tumors. Thus, in particular embodiments, one can test these changes on thyroid needle biopsy to assist the diagnosis of thyroid cancer. Also, the genetic (mutation) and epigenetic (methylation) information of RASAL1 may be used in the future to guide targeted treatment of thyroid cancer. As genetic and epigenetic alteration-caused inactivation or defects of RASAL1 can result in activation of the MAP kinase and PI3K pathways, targeting these pathways using corresponding inhibitors (e.g., BRAF and MEK inhibitors, PI3K and Akt inhibitors) may be therapeutically effective particularly in human cancers, including thyroid cancer that harbor genetic or epigenetic alterations of the RASAL1 gene. Thus, these findings described herein on RASAL1 have general implication for targeted therapy. In other words, in particular embodiments, one could test RASAL1 mutations and/or methylation and, if the result is positive, one can treat the cancer with the currently known inhibitors of MAP kinase and PI3K pathways.

Accordingly, in one aspect, the present invention provides methods for predicting an increased risk of thyroid cancer in a patient. In certain embodiments, the method comprises the steps of (a) treating DNA isolated from a sample collected from the patient using bisulfite; (b) measuring the DNA methylation level of the promoter region of the RASAL1 gene from the bisulfite-treated DNA using methylation-specific polymerase chain reaction (MSP), wherein the MSP creates a methylation and unmethylation band; (c) normalizing the measured DNA methylation level using an internal reference gene; (d) calculating the percentage of allelic methylation using the formula [M/(M+U)×100%, wherein M and U represent the density of the methylation and unmethylation band; and (e) predicting an increased risk of thyroid cancer in the subject if the percentage of allelic methylation is at least 40%.

In particular embodiments, the MSP is performed using the primers shown in SEQ ID NOS:35-36. In specific embodiments, MSP is performed using the primers shown in SEQ ID NOS:35-38. In certain embodiments, an increased risk of thyroid cancer in the subject is predicted if the percentage of allelic methylation is at least 50%.

In another embodiment, a method for predicting an increased risk of thyroid cancer in a patient comprises the steps of (a) PCR amplifying exons 13, 14, 15 and 17 of the RASAL1 gene from DNA isolated from a sample collected from the patient, wherein the amplified products comprise nucleotide 1031 of Exon 13, nucleotides 1153, 1201, 1303, 1312, and 1313 of Exon 14, nucleotide 1422 of Exon 15, and nucleotide 1782 of Exon 17, where nucleotide 1 is defined as A of the ATG translation initiation codon of the RASAL1 gene; (b) sequencing the PCR amplification products; and (c) predicting an increased risk of thyroid cancer if one or more of the following nucleotide changes are present in the sequenced PCR amplification products: A1031G (Exon 13), C1153T (Exon 14), G1201A (Exon 14), C1303T (Exon 14), C1312T (Exon 14), G1313A (Exon 14), C1422A (Exon 15), and G1782A (Exon 17). In more specific embodiments, the following primers are used for the PCR amplification step: SEQ ID NOS:57-58 for Exon 13; SEQ ID NOS:59-60 for Exon 14, SEQ ID NOS:61-62 for Exon15, and SEQ ID NOS:65-66 for Exon 17. In other embodiments, the methods for assessing methylation and mutation status can be combined. Treatment methods can also comprise either one or both of such methods and can further include treatment with inhibitors of MAP kinase and/or PI3K pathways.

In another aspect, the present invention provides methods of inhibiting cellular proliferation. In a specific embodiment, the method comprises contacting a cell with (a) a recombinant vector comprising a nucleic acid sequence encoding RASAL1 protein or a biologically active fragment thereof or (b) a RASAL1 protein or biologically active fragment thereof. In a more specific embodiment, the RASAL1 protein comprises the amino acid sequence of SEQ ID NO:85. In particular embodiments, the cell is a tumor cell. In certain embodiments, the method is an in vivo method of inhibiting cellular proliferation.

The present invention also provides a recombinant vector comprising a nucleic acid sequence encoding RASAL1 or a biologically active fragment thereof. In another embodiment, the present invention provides a method for treating thyroid cancer in a patient comprising the step of administering to the patient an effective dose of a RASAL1 protein or biologically active fragment thereof. In yet another embodiment, a method for treating thyroid cancer in a patient comprises the step of administering to a patient a vector encoding RASAL1 protein or a biologically active fragment thereof. In other embodiments, the present invention provides a RASAL1 protein or biologically active fragment thereof for use in a method of treating thyroid cancer, wherein the RASAL1 protein or biologically active fragment thereof are administered to the recipient in a therapeutically effective amount.

BRIEF DESCRIPTION OF THE FIGURES

FIG. 2A-2E. Hypermethylation of RASAL1 and its re-expression induced by demethylation in thyroid cancer cells. A) Methylation-specific polymerase chain reaction (MSP) analysis revealed hypermethylation of the promoter area of RASAL1 in most of the 14 thyroid cell lines. B) Partial demethylation of RASAL1 revealed by MSP analysis in thyroid cancer cell lines after 5-Aza-dC treatment. After cells were treated with 5 μM 5-Aza-dC for 24 hours, RNA and genomic DNA were extracted and used for reverse-transcription polymerase chain reaction (RT-PCR) and MSP analysis, respectively. C) RT-PCR analysis of RASAL1 expression in thyroid cancer cell lines treated with or without demethylating agent 5-Aza-dC. D) MSP analysis of RASAL1 in matched normal and cancerous thyroid tissues. Six matched sample pairs are presented that had different methylation patterns between normal and matched tumor tissues. E) RASAL1 methylation levels represented by the indicated allelic methylation percentages (x-axis) and their frequencies (y-axis) in different types of thyroid cancers. ATC=anaplastic thyroid cancer; FTC=follicular thyroid cancer; PTC=papillary thyroid cancer.

DETAILED DESCRIPTION OF THE INVENTION

Figure 1A:
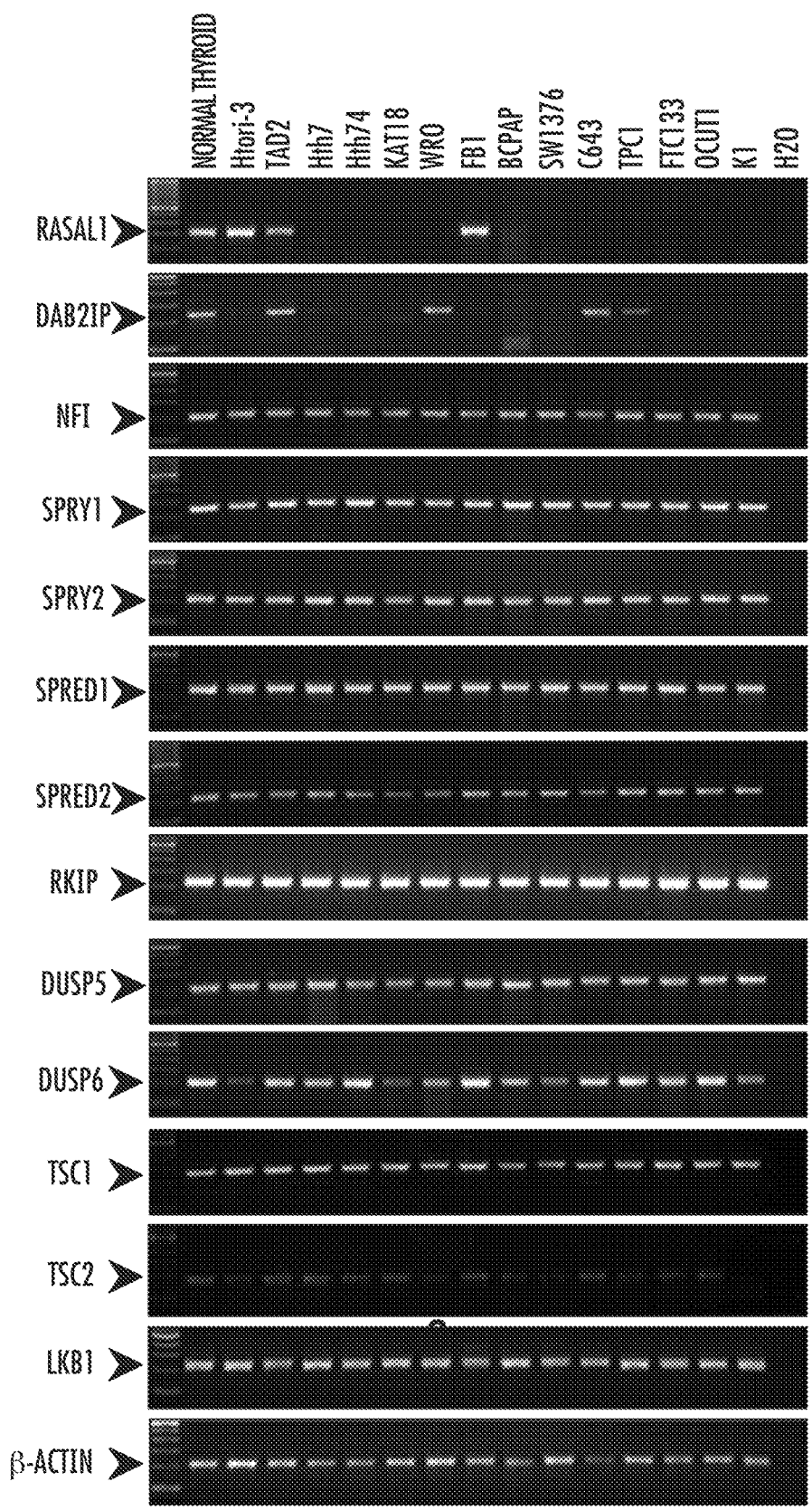
FIG. 1A-1B. Expression of candidate tumor-suppressor genes that negatively regulate RAS signaling in thyroid cancer cell lines. A) Reverse transcription analysis of a cDNA panel derived from 12 human thyroid cancer cell lines as indicated. The cDNA from normal human thyroid tissue and two immortalized normal human thyroid epithelial cell lines (Htori-3 and TAD2) were used as positive controls. β-Actin cDNA was used to show the integrity and quantity of cDNA samples. The primer sequences are presented in Table 3. B) Detection of RASAL1 protein in thyroid cell lines by western blotting assay. β-Actin protein level was used to show the quantity and integrity of protein samples.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term "about."

"Optional" or "optionally" means that the subsequently described event or circumstance can or cannot occur, and that the description includes instances where the event or circumstance occurs and instances where it does not.

The terms "patient," "individual," or "subject" are used interchangeably herein, and refer to a mammal, particularly, a human. The patient may have a mild, intermediate or severe disease or condition. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates. In particular, the term also includes mammals diagnosed with a RASAL1-mediated disease, disorder or condition. By "normal subject" is meant an individual who does not have cancer as well as an individual who has increased susceptibility for developing a cancer.

As used herein, the term "comparing" refers to making an assessment of how the methylation status, proportion, level or cellular localization of one or more biomarkers in a sample from a subject relates to the methylation status, proportion, level or cellular localization of the corresponding one or more biomarkers in a standard or control sample. For example, "comparing" may refer to assessing whether the methylation status, proportion, level, or cellular localization of one or more biomarkers in a sample from a subject is the same as, more or less than, or different from the methylation status, proportion, level, or cellular localization of the corresponding one or more biomarkers in standard or control sample. More specifically, the term may refer to assessing whether the methylation status, proportion, level, or cellular localization of one or more biomarkers in a sample from a subject is the same as, more or less than, different from or otherwise corresponds (or not) to the methylation status, proportion, level, or cellular localization of predefined biomarker levels that correspond to, for example, a subject at risk for thyroid cancer, not at risk for thyroid cancer, and the like. In a specific embodiment, the term "comparing" refers to assessing whether the methylation level of one or more biomarkers of the present invention in a sample from a subject is the same as, more or less than, different from other otherwise correspond (or not) to methylation levels of the same biomarkers in a control sample (e.g., predefined levels that correlate to subject not at risk for or predicted to develop thyroid cancer).

As used herein, the terms "indicates" or "correlates" (or "indicating" or "correlating," or "indication" or "correlation," depending on the context) in reference to a parameter, e.g., a modulated proportion, mutation status, level, or cellular localization in a sample from a subject, may mean that the subject is at risk for thyroid cancer. In specific embodiments, the parameter may comprise the mutation status and/or methylation status or level of one or more biomarkers of the present invention. A particular set or pattern of methylation of one or more biomarkers may indicate that a subject is at risk for thyroid cancer (i.e., correlates to a subject at risk for thyroid cancer). In other embodiments, a particular set or pattern of methylation of one or more biomarkers may be correlated to a subject being unaffected or not at risk of thyroid cancer. In certain embodiments, "indicating," or "correlating," as used according to the present invention, may be by any linear or non-linear method of quantifying the relationship between methylation levels of biomarkers to a standard, control or comparative value for the prediction of thyroid cancer, assessment of efficacy of clinical treatment, identification of a subject that may respond to a particular treatment regime or pharmaceutical agent, monitoring of the progress of treatment, and in the context of a screening assay, for the identification of an anti-thyroid cancer therapeutic.

The terms "measuring" and "determining" are used interchangeably throughout, and refer to methods which include obtaining a subject sample and/or detecting the mutation and/or methylation status or level of a biomarker(s) in a sample. In one embodiment, the terms refer to obtaining a subject sample and detecting the mutation and/or methylation status or level of one or more biomarkers in the sample. In another embodiment, the terms "measuring" and "determining" mean detecting the mutation and/or methylation status or level of one or more biomarkers in a subject sample. Measuring can be accomplished by methods known in the art and those further described herein including, but not limited to, methylation-specific polymerase chain reaction (MSP). The term "measuring" is also used interchangeably throughout with the term "detecting."

The term "methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively. By "hypermethylation" or "elevated level of methylation" is meant an increase in methylation of a region of DNA (e.g., a biomarker of the present invention) that is considered statistically significant over levels of a control population. "Hypermethylation" or "elevated level of methylation" may refer to increased levels seen in a subject over time.

In particular embodiments, a biomarker would be unmethylated in a normal sample (e.g., normal or control tissue, or normal or control body fluid, stool, blood, plasma, serum, urine, cerebrospinal fluid, saliva, amniotic fluid), most importantly in healthy stool, blood, plasma, serum, urine, cerebrospinal fluid, saliva, amniotic fluid or other body fluid. In other embodiments, a biomarker would be hypermethylated in a sample from a subject having or at risk of thyroid cancer, preferably at a methylation frequency of at least about 10%, at least about 20%, at least about 30%, at least about 40%, at least about 50%, at least about 60%, at least about 70%, at least about 75%, at least about 80%, at least about 85%, at least about 90%, at least about 95%, or about 100%.

A "methylation profile" refers to a set of data representing the methylation states or levels of one or more loci within a molecule of DNA from e.g., the genome of an individual or cells or sample from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus. In some embodiments, a methylation profile refers to the methylation states or levels of one or more biomarkers described herein, including RASAL1. In more specific embodiments, a methylation profile refers to the methylation states of the 5' region of the RASAL1 gene. In even more specific embodiments, a methylation profile refers to the methylation state of the promoter region of RASAL1.

The terms "methylation status" or "methylation level" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value" or "methylation level." A methylation value or level can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. An alternative method of expressing methylation level is described in the Examples section. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold or control value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., 22(17) NUCLEIC ACIDS RES. 3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The terms "sample," "subject sample," "biological sample," and the like, encompass a variety of sample types obtained from a patient, individual, or subject and can be used in a diagnostic or monitoring assay. The subject sample may be obtained from a healthy subject, a subject suspected to be at risk for thyroid cancer (family history) or a subject having a conditions associated with thyroid cancer. Moreover, a sample obtained from a subject can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or subject, e.g., a control or normal cell, organ, or subject, exhibiting, for example, normal traits. For example, the biomarkers of the present invention may be assayed for their methylation level in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., a thyroid cancer treatment (or treatment for a condition that may lead to thyroid cancer) on a subject. In yet another embodiment, a transcription rate, mRNA level, translation rate, protein level, biological activity, cellular characteristic or property, genotype, phenotype, etc. can be determined prior to, during, or after administering a therapy into a cell, organ, or subject. In a further embodiment, a "suitable control" or "appropriate control" is a predefined value, level, feature, characteristic, property, etc. A "suitable control" can be a methylation profile of one or more biomarkers of the present invention that correlates to thyroid cancer, to which a subject sample can be compared. The subject sample can also be compared to a negative control, i.e., a methylation profile that correlates to not at risk of developing thyroid cancer.

An "agonist" is a type of modulator and refers to an agent that binds a target and can activate one or more functions of the target. For example, an agonist of a protein can bind the protein and activate the protein in the absence of its natural or cognate ligand.

As used herein, an "antagonist" is a type of modulator and is used interchangeably with the term "inhibitor." In certain non-limiting embodiments, the term refers to an agent that binds a target (e.g., a protein) and can inhibit a one or more functions of the target. For example, an antagonist of an enzymatic protein can bind the protein and inhibit the enzymatic activity of the protein.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against RASAL1 and used as RASAL1 modulators.

As used herein, the term "effective," means adequate to accomplish a desired, expected, or intended result. More particularly, a "therapeutically effective amount" as provided herein refers to an amount of a RASAL1 modulator of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of a RASAL1 modulator, necessary to provide the desired therapeutic effect, e.g., an amount that is effective to prevent, alleviate, or ameliorate symptoms of disease or prolong the survival of the subject being treated. In a particular embodiment, the disease or condition is cancer. In a more specific embodiment, the cancer is thyroid cancer. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

By "high stringency conditions" is meant conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. See, for example, F. Ausubel et al., Current Protocols in Molecular Biology, John Wiley & Sons, New York, N.Y., 1998.

The term "inhibitor" is a type of modulator and is used interchangeably with the term "antagonist." The term "inhibitor" includes any type of molecule or agent that directly or indirectly inhibits the expression or activity of a target gene or protein. An inhibitor can be any type of compound, such as a small molecule, antibody or antisense compound. In certain embodiments, the target gene or protein is BRAF. The term also includes agents that have activity in addition to BRAF inhibitory activity. Examples of BRAF inhibitors include Sorafenib (Bay 43-9006, Nexavar) and Vemurafenib (PLX4032), BDC-0879, PLX-4720, Dabrafenib (Tafinlar), and LGX818. In still another embodiment, the target gene or protein is MEK, a protein downstream BRAF in the BRAF/MEK/MAP kinase pathway.

Examples of MEK inhibitors include trametinib, selumetinib (AZD6244), trametinib, CI1040, PD0325901, RDEA119 (refametinib, BAY 869766). In still another embodiment, the combination use of BRAF, TERT and/or MEK inhibitors targeting all genes or proteins is more effective. In still another embodiment, the treatment targets simultaneously RASAL1, TERT and BRAF/MEK using their corresponding agonists/inhibitors.

As used herein, the term "modulate" indicates the ability to control or influence directly or indirectly, and by way of non-limiting examples, can alternatively mean inhibit or stimulate, agonize or antagonize, hinder or promote, and strengthen or weaken. Thus, the term "RASAL1 modulator" refers to an agent that modulates the expressions and/or activity of RASAL1. Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid; glycopeptides; glycoprotein; proteoglycan and the like; and synthetic analogues or derivatives thereof, including peptidomimetics, small molecule organic compounds and the like, and mixtures thereof. A modulator identified according to the invention is preferably useful in the treatment of a disease disclosed herein.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. In addition, as used herein, the term "polypeptide" refers to amino acids joined to each other by peptide bonds or modified peptide bonds, e.g., peptide isosteres, etc., and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983).

"Biologically active" or "functional fragments" and variants of a polypeptide include those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. Third, part of a polypeptide chain can be deleted without impairing or eliminating all of its functions. Fourth, insertions or additions can be made in the polypeptide chain for example, adding epitope tags, without impairing or eliminating its functions. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides and labels useful for such purposes are well known in the art, and include radioactive isotopes such as $^{32}$P, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, or 200 amino acid residues. A biologically active or functional fragment or variant of RASAL1 is defined herein as a polypeptide which is capable of having RASAL1 tumor suppressor activity. It includes any polypeptide five or more amino acid residues in length which is capable of having RASAL1 tumor suppressor activity.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for RASAL1 nucleic acids (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the RASAL1 nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

By "specifically hybridizes" is meant that a probe, primer, or oligonucleotide recognizes and physically interacts (that is, base-pairs) with a substantially complementary nucleic acid (for example, a RASAL1 nucleic acid) under high stringency conditions, and does not substantially base pair with other nucleic acids.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In a specific embodiment, the disease or condition is cancer. In particular embodiments, the cancer is thyroid cancer.

The terms "RASAL1-related disease, disorder or condition" or "RASAL1-mediated disease, disorder or condition," and the like mean diseases, disorders or conditions associated with aberrant RASAL1 activity. In a specific embodiment, the disease or condition is cancer. In general, the term refers to any abnormal state that involves RASAL1 activity. The abnormal state can be due, for example, to a genetic defect. In certain embodiments, the abnormal state or aberrant activity refers to reduced or no biological activity.

II. Hypermethylated RASAL1 and Detection Thereof

The biomarkers of the present invention are differentially methylated in subjects at risk of thyroid cancer versus "normal" individuals. Such biomarkers can be used individually as diagnostic tool, or in combination as a biomarker panel. In particular embodiments, the biomarkers include RASAL1. In more specific embodiments, the biomarkers comprise the 5' region of RASAL1. In even more specific embodiments, the biomarkers comprise the promoter region of RASAL1.

The DNA biomarkers of the present invention comprise fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particular, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease or condition.

There are a number of methods that can be employed to measure, detect, determine, identify, and characterize the methylation status/level of a biomarker (i.e., a region/fragment of DNA or a region/fragment of genome DNA (e.g., CpG island-containing region/fragment)) in the development of a disease or condition (e.g., thyroid cancer) and thus diagnose risk or status of the disease or condition.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al., 34(1) BIOTECHMQUES 106-15 (2003); Deiman B, et al., 20(2) MOL. BIOTECHNOL. 163-79 (2002); and Gibson et al., 6 GENOME RESEARCH 995-1001 (1996). Amplifications may be monitored in "real time."

Additional methods for detecting DNA methylation can involve genomic sequencing before and after treatment of the DNA with bisulfite. See, e.g., Frommer et al., 89 PROC. NATL. ACAD. SCI. USA 1827-31 (1992). When sodium bisulfite is contacted to DNA, unmethylated cytosine is converted to uracil, while methylated cytosine is not modified. In some embodiments, restriction enzyme digestion of PCR products amplified from bisulfite-converted DNA is used to detect DNA methylation. See, e.g., Xiong & Laird, 25 NUCLEIC ACIDS RES. 2532-34 (1997); and Sadri & Hornsby, 24 NUCL. ACIDS RES. 5058-59 (1996).

In some embodiments, a MethyLight assay is used alone or in combination with other methods to detect DNA methylation. See, Eads et al., 59 CANCER RES. 2302-06 (1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In other embodiments, a Methylation-sensitive Single Nucleotide Primer Extension (Ms-SNuPE) reaction is used alone or in combination with other methods to detect DNA methylation. See Gonzalgo & Jones, 25 NUCLEIC ACIDS RES. 2529-31 (1997). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In further embodiments, a methylation-specific PCR reaction is used alone or in combination with other methods to detect DNA methylation. A methylation-specific PCR assay entails initial modification of DNA by sodium bisulfite, converting all unmethylated, but not methylated, cytosines to uracil, and subsequent amplification with primers specific for methylated versus unmethylated DNA. See, Herman et al., 93 PROC. NATL. ACAD. SCI. USA 9821-26, (1996); and U.S. Pat. No. 5,786,146.

Additional methylation detection methods include, but are not limited to, methylated CpG island amplification (see, Toyota et al., 59 CANCER RES. 2307-12 (1999)) and those methods described in, e.g., U.S. Pat. Nos. 7,553,627; 6,331, 393; U.S. patent Ser. No. 12/476,981; U.S. Patent Publication No. 2005/0069879; Rein, et al., 26(10) NUCLEIC ACIDS RES. 2255-64 (1998); and Olek et al., 17(3) NAT. GENET. 275-6 (1997).

In another aspect, the present invention provides kits for qualifying thyroid cancer risk status, which kits are used to detect or measure the methylation status/levels of the biomarkers described herein. Such kits can comprise at least one polynucleotide that hybridizes to at least one of the diagnostic biomarker sequences of the present invention and at least one reagent for detection of gene methylation. Reagents for detection of methylation include, e.g., sodium bisulfite, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides (e.g., primers and/or probes) capable of specifically amplifying at least a portion of a DNA region of a biomarker of the present invention including RASAL1. Optionally, one or more detectably-labeled polypeptides capable of hybridizing to the amplified portion can also be included in the kit. In some embodiments, the kits comprise sufficient primers to amplify 1, 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of a biomarker of the present invention including RASAL1.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of a biomarker of the present invention including RASAL1.

In some embodiments, the kits comprise a methylation binding moiety and one or more polynucleotides to quantify the number of copies of at least a portion of a DNA region of a biomarker of the present invention including RASAL1. A methylation binding moiety refers to a molecule (e.g., a polypeptide) that specifically binds to methyl-cytosine. Examples include restriction enzymes or fragments thereof that lack DNA cutting activity but retain the ability to bind methylated DNA, antibodies that specifically bind to methylated DNA, etc.).

III. RASAL1 Mutations as Biomarkers and Detection Thereof

The present inventors have discovered that certain mutations in the RASAL1 gene provide a unique genetic background that predict or result in an increased likelihood of human thyroid cancer. Thyroid cancer can include follicular thyroid cancer (FTC), papillary thyroid cancer (PTC), conventional PTC, follicular variant PTC (FVPTC), tall-cell PTC (TCPTC).

Thus, in certain embodiments, the RASAL1 mutations can thus be used to identify individuals having or at risk of developing cancer. In further embodiments, the RASAL1 mutations can be used to identify individuals at risk for having or developing aggressive thyroid cancer such as TCPTC, PDTC, ATC and PTC. The mutations can be identified in subjects who have or have not been diagnosed with cancer.

In certain embodiments, DNA can be isolated from a biological sample taken from a subject. DNA can be extracted and purified from biological samples using any suitable technique. A number of techniques for DNA extraction and/or purification are known in the art, and several are commercially available (e.g., ChargeSwitch®, MELT™ total nucleic acid isolation system, MagMAX™ FFPE total nucleic acid isolation kit, MagMAX™ total nucleic acid isolation kit, QIAamp DNA kit, Omni-Pure™ genomic DNA purification system, WaterMaster™ DNA purification kit). Reagents such as DNAzol® and TR1 Reagent® can also be used to extract and/or purify DNA. DNA can be further purified using Proteinase K and/or RNAse.

In further embodiments, primer/probes can be used to amplify a region of the RASAL1 gene. More specifically, primers/probes are capable of amplifying the loci listed in Table 1, including nucleotide changes at A1031G (Exon 13), C1153T (Exon 14), G1201A (Exon 14), C1303T (Exon 14), C1312T (Exon 14), G1313A (Exon 14), C1422A (Exon 15), and G1782A (Exon 17), where nucleotide 1 is defined as A of the ATG translation initiation codon (GeneBank Accession No. NM_004658) of the RASAL1 gene (SEQ ID NO:85). In certain embodiments, useful primers comprise one or more of the nucleic acid sequences shown in SEQ ID NOS:39-76. In specific embodiments, useful primers comprise one or more of the nucleic acid sequences shown in 57-62 and 65-66.

In particular embodiments, a primer is contacted with isolated DNA from the subject under conditions such that the primer specifically hybridizes with the RASAL1 genes. The primer and DNA thus form a primer:DNA complex. In certain embodiments, the hybridization conditions are such that the formation of the primer:DNA complex is the detection step itself, i.e., the complex forms only if the mutation is present. In other embodiments, the primer:DNA complex is amplified using polymerase chain reaction, the presence (or not) of the mutation is detected. In certain embodiments, the mutations are detected by sequencing.

As described herein, in certain embodiments, the primers can used to support DNA amplification reactions. Typically the primers will be capable of being extended in a sequence specific manner. Extension of a primer in a sequence specific manner includes any methods wherein the sequence or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the polynucleotide sequences disclosed herein or region of the polynucleotide sequences disclosed herein or they hybridize with the complement of the polynucleotide sequences disclosed herein or complement of a region of the polynucleotide sequences disclosed herein.

The size of the primers or probes for interaction with the polynucleotide sequences disclosed herein in certain embodiments can be any size that supports the desired enzymatic manipulation of the primer, such as DNA amplification or the simple hybridization of the probe or primer. A typical primer or probe would be at least 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long or any length in-between.

The probes or primers of the present invention can be prepared by conventional techniques well-known to those skilled in the art. For example, the probes can be prepared using solid-phase synthesis using commercially available equipment. Modified oligonucleotides can also be readily prepared by similar methods. The probes can also be synthesized directly on a solid support according to methods standard in the art. This method of synthesizing polynucleotides is particularly useful when the polynucleotide probes are part of a nucleic acid array.

The present invention therefore also provides predictive, diagnostic, and prognostic kits comprising degenerate primers to amplify a target nucleic acid in the RASAL1 gene and instructions comprising amplification protocol and analysis of the results. The kit may alternatively also comprise buffers, enzymes, and containers for performing the amplification and analysis of the amplification products. The kit may also be a component of a screening, diagnostic or prognostic kit comprising other tools such as DNA microarrays. In some embodiments, the kit also provides one or more control templates, such as nucleic acids isolated from normal tissue sample, and/or a series of samples representing different variances in the RASAL1 gene.

In one embodiment, the kit provides at least one primer capable of amplifying a different region of the RASAL1 gene. The kit may comprise additional primers for the analysis of expression of several gene variances in a biological sample in one reaction or several parallel reactions. Primers in the kits may be labeled, for example fluorescently labeled, to facilitate detection of the amplification products and consequent analysis of the nucleic acid variances.

In one embodiment, more than one mutation/variance can be detected in one analysis. A combination kit will therefore comprise of primers capable of amplifying different segments of the RASAL1 gene. The kit may also comprise primers capable of amplifying segments of another gene(s) including BRAF and/or TERT. The primers may be differentially labeled, for example, using different fluorescent labels, so as to differentiate between the variances. The primers contained within the kit may include primers selected from complementary sequences to the coding sequence of RASAL1, TERT or BRAF.

In certain embodiments, a patient can be diagnosed or identified by adding a biological sample (e.g., blood or blood serum) obtained from the patient to the kit and detecting the RASAL1 mutations(s), for example, by a method which comprises the steps of: (i) collecting blood or blood serum from the patient; (ii) separating DNA from the patient's blood; (iii) adding the DNA from patient to a diagnostic kit; and, (iv) detecting (or not) the RASAL1 mutation(s). In this exemplary method, primers are brought into contact with the patient's DNA. The formation of the primer:DNA complex can, for example, be PCR amplified and, in some embodiments, sequenced to detect (or not) the RASAL1 mutation. In other kit and diagnostic embodiments, blood or blood serum need not be collected from the patient (i.e., it is already collected). Moreover, in other embodiments, the sample may comprise a tissue sample, urine or a clinical sample.

IV. Determination of a Subject's Risk of Thyroid Cancer

The present invention relates to the use of biomarkers to predict thyroid cancer. More specifically, the biomarkers of the present invention can be used in diagnostic tests to predict or determine the risk of thyroid cancer in an individual, subject or patient. More specifically, the biomarkers to be detected in predicting thyroid cancer risk include RASAL1.

A. Biomarker Panels

The biomarkers of the present invention can be used in diagnostic tests to assess, determine, and/or qualify (used interchangeably herein) thyroid cancer risk in a subject. The phrases "at risk of thyroid cancer," "predictive of thyroid cancer" and the like include any distinguishable manifestation of the risk or associated condition, including non-risk. Based on this status, further procedures may be indicated, including additional diagnostic tests or therapeutic procedures or regimens. It is understood that although the description below is recited in the context of the methylation of RASAL1, the description applies equally to the RASAL1 mutations described herein, and should be construed to apply only to methylation.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker of the present invention may show a statistical difference in different thyroid cancer risks of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially methylated mutated in UI (or NC) and individuals at risk of thyroid cancer. In certain embodiments, the biomarkers are measured in a subject sample using the methods described herein and compared, for example, to predefined biomarker levels and correlated to thyroid cancer risk. In particular embodiments, the measurement(s) may then be compared with a relevant diagnostic amount(s), cut-off(s), or multivariate model scores that distinguish a positive thyroid cancer risk status from a negative thyroid cancer risk status. The diagnostic amount(s) represents a measured amount of a hypermethylated biomarker(s) above which or below which a subject is classified as having a particular thyroid cancer risk status. For example, if the biomarker(s) is/are hypermethylated compared to normal, then a measured amount(s) above the diagnostic cutoff(s) provides a diagnosis of thyroid cancer risk. Alternatively, if the biomarker(s) is/are hypomethylated in a subject, then a measured amount(s) at or below the diagnostic cutoff(s) provides a diagnosis of non-thyroid cancer risk. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarker hypermethylation in a statistically significant number of samples from subjects with the different thyroid cancer risk statuses, and drawing the cut-off to suit the desired levels of specificity and sensitivity.

Indeed, as the skilled artisan will appreciate there are many ways to use the measurements of the methylation status of two or more biomarkers in order to improve the diagnostic question under investigation. In a quite simple, but nonetheless often effective approach, a positive result is assumed if a sample is hypermethylation positive for at least one of the markers investigated.

Furthermore, in certain embodiments, the methylation values measured for markers of a biomarker panel are mathematically combined and the combined value is correlated to the underlying diagnostic question. Methylated biomarker values may be combined by any appropriate state of the art mathematical method. The values may be combined with the detected RASAL1 missense/non-sense mutations described herein. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating methylation status of a biomarker combination of the present invention, e.g. to predict thyroid cancer, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of Thyroid Cancer

In a specific embodiment, the present invention provides methods for determining the risk of thyroid cancer by a subject. RASAL1 mutation and/or biomarker methylation percentages, amounts or patterns are characteristic of various risk states, e.g., high, medium or low. The risk of thyroid cancer is determined by measuring the methylation status of the relevant biomarkers and then either submitting them to a classification algorithm or comparing them with a reference amount, i.e., a predefined level or pattern of methylated (and/or unmethylated) biomarkers that is associated with the particular risk level.

C. Subject Management

In certain embodiments of the methods of the present invention, the methods further comprise managing subject treatment based on the RASAL1 mutation and/or biomarker methylation status. Such management includes the actions of the physician or clinician subsequent to determining thyroid cancer risk status. For example, if a physician makes a prognosis of thyroid cancer, then a certain regime of monitoring would follow. An assessment of the risk using the methods of the present invention may then require a certain therapy regimen. Alternatively, a diagnosis of non-risk of thyroid cancer might be followed with further testing to determine a specific disease that the subject might be suffering from. Also, further tests may be called for if the test gives an inconclusive result on thyroid cancer risk status.

D. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a subject on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of hypermethylation of one or more of the biomarkers of the present invention may change toward a non-thyroid cancer risk profile. Therefore, one can follow the course of the methylation status of one or more biomarkers in the subject during the course of treatment. Accordingly, this method involves measuring methylation levels of one or more biomarkers in a subject receiving drug therapy, and correlating the levels with the thyroid cancer risk status of the subject (e.g., by comparison to predefined methylation levels of the biomarkers that correspond to different thyroid cancer risk statuses). One embodiment of this method involves determining the methylation levels of one or more biomarkers at at least two different time points during a course of drug therapy, e.g., a first time and a second time, and comparing the change in methylation levels of the biomarkers, if any. For example, the methylation levels of one or more biomarkers can be measured before and after drug administration or at two different time points during drug administration. The effect of therapy is determined based on these comparisons. If a treatment is effective, then the methylation status of one or more biomarkers will trend toward normal, while if treatment is ineffective, the methylation status of one or more biomarkers will trend toward thyroid cancer risk indications.

E. Generation of Classification Algorithms for Qualifying Thyroid Cancer Risk

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition or risk of thyroid cancer.

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002/0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarker biomarkers already discovered, and for finding new biomarker biomarkers. The classification algorithms, in turn, form the base for diagnostic tests by providing diagnostic values (e.g., cut-off points) for biomarkers used singly or in combination.

Without further elaboration, it is believed that one skilled in the art, using the preceding description, can utilize the present invention to the fullest extent. The following examples are illustrative only, and not limiting of the remainder of the disclosure in any way whatsoever.

V. Pharmaceutical Compositions and Administration

The RASAL1 agonists described herein have in vitro and in vivo diagnostic and therapeutic utilities. For example, these molecules can be administered to cells in culture, e.g., in vitro or in vivo, or in a subject, e.g., in vivo, to treat, prevent or diagnose cancer or other disease, disorder or condition that may be affected or mediated by RASAL1. In a specific embodiment, the disease, disorder or condition is thyroid cancer. RASAL1 agonists are particularly suitable for treating human patients suffering from thyroid cancer.

In certain embodiments, the RASAL1 agonist is selected from the group consisting of a small molecule, a polypeptide, a nucleic acid molecule, a peptidomimetic, or a combination thereof. In a specific embodiment, the agent can be a polypeptide. The polypeptide can, for example, comprise the full length RASAL1 protein. In another embodiment, the agent can be a biologically active fragment of RASAL1. The polypeptide can also comprise an antibody. In another embodiment, the agent can be a nucleic acid molecule.

The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77 (1985)) and by Boemer et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362:255-8 (1993); Bruggermann et al., Year in Immunol. 7:33 (1993)).

In other embodiments, a RASAL1 agonist is a small molecule. The term "small molecule organic compounds" refers to organic compounds generally having a molecular weight less than about 5000, 4000, 3000, 2000, 1000, 800, 600, 500, 250 or 100 Daltons, preferably less than about 500 Daltons. A small molecule organic compound may be prepared by synthetic organic techniques, such as by combinatorial chemistry techniques, or it may be a naturally-occurring small molecule organic compound.

Compound libraries may be screened for RASAL1 agonists. A compound library is a mixture or collection of one or more putative modulators generated or obtained in any manner. Any type of molecule that is capable of interacting, binding or has affinity for RASAL1 may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, receptors, nucleic acids, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such as peptidomimetics and the like; and non-naturally occurring molecules, such as "small molecule" organic compounds generated, for example, using combinatorial chemistry techniques; and mixtures thereof.

A library typically contains more than one putative modulator or member, i.e., a plurality of members or putative modulators. In certain embodiments, a compound library may comprise less than about 50,000, 25,000, 20,000, 15,000, 10000, 5000, 1000, 500 or 100 putative modulators, in particular from about 5 to about 100, 5 to about 200, 5 to about 300, 5 to about 400, 5 to about 500, 10 to about 100, 10 to about 200, 10 to about 300, 10 to about 400, 10 to about 500, 10 to about 1000, 20 to about 100, 20 to about 200, 20 to about 300, 20 to about 400, 20 to about 500, 20 to about 1000, 50 to about 100, 50 to about 200, 50 to about 300, 50 to about 400, 50 to about 500, 50 to about 1000, 100 to about 200, 100 to about 300, 100 to about 400, 100 to about 500, 100 to about 1000, 200 to about 300, 200 to about 400, 200 to about 500, 200 to about 1000, 300 to about 500, 300 to about 1000, 300 to 2000, 300 to 3000, 300 to 5000, 300 to 6000, 300 to 10,000, 500 to about 1000, 500 to about 2000, 500 to about 3000, 500 to about 5000, 500 to about 6000, or 500 to about 10,000 putative modulators. In particular embodiments, a compound library may comprise less than about 50,000, 25,000, 20,000, 15,000, 10,000, 5,000, 1000, or 500 putative modulators.

A compound library may be prepared or obtained by any means including, but not limited to, combinatorial chemistry techniques, fermentation methods, plant and cellular extraction procedures and the like. A library may be obtained from synthetic or from natural sources such as for example, microbial, plant, marine, viral and animal materials. Methods for making libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Compound libraries may also be obtained from commercial sources including, for example, from Maybridge, ChemNavigator.com, Timtec Corporation, ChemBridge Corporation, A-Syntese-Biotech ApS, Akos-SC, G & J Research Chemicals Ltd., Life Chemicals, Interchim S.A., and Spectrum Info. Ltd.

Accordingly, a pharmaceutical composition of the present invention may comprise an effective amount of a RASAL1 agonist. As used herein, the term "effective," means adequate to accomplish a desired, expected, or intended result. More particularly, an "effective amount" or a "therapeutically effective amount" is used interchangeably and refers to an amount of a RASAL1 agonist, perhaps in further combination with yet another therapeutic agent, necessary to provide the desired "treatment" (defined herein) or therapeutic effect, e.g., an amount that is effective to prevent, alleviate, treat or ameliorate symptoms of a disease or prolong the survival of the subject being treated. In particular embodiments, the pharmaceutical compositions of the present invention are administered in a therapeutically effective amount to treat patients suffering from thyroid cancer. As would be appreciated by one of ordinary skill in the art, the exact low dose amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which a RASAL1 agonist is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a RASAL1 agonist together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising a RASAL1 agonist may be used alone or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising a RASAL1 agonist, optionally in combination with another therapeutic agent) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

The pharmaceutical compositions may further be combined with one or more additional therapeutic agents. In particular embodiments, the second therapeutic agent can be an anti-cancer compound. A combination therapy regimen may be additive, or it may produce synergistic results.

The compositions can be administered simultaneously or sequentially by the same or different routes of administration. The determination of the identity and amount of the pharmaceutical compositions for use in the methods of the present invention can be readily made by ordinarily skilled medical practitioners using standard techniques known in the art. In specific embodiments, a RASAL1 agonist of the present invention can be administered in combination with an effective amount of another therapeutic agent, depending on the disease or condition being treated.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Human Thyroid Tissues and Cell Lines.

The study included 101 human thyroid tumors. Protocols using human thyroid tumor tissues were approved by the institutional review board of the Johns Hopkins Medical Institution. Written informed consent was provided from patients where required. All follicular thyroid cancer tumors used in this study were conventional type. Some genomic DNA samples were from our previous studies (27).

Thyroid cancer cell lines and their genetic backgrounds are summarized in Table 2, which we gratefully received as acknowledged previously (28). They were all grown in Roswell Park Memorial Institute 1640 medium with 10% fetal bovine serum, except for FTC133, which was cultured in Dulbecco's modified Eagle's medium/Ham's F-12 medium as described previously (28).

Methylation-Specific Polymerase Chain Reaction (MSP).

DNA bisulfite treatment was performed as previously described (29). See Table 3 for MSP primer sequences. The relative level of methylation was normalized using the ratio obtained from the values of the gene of interest over the values of the internal reference gene (β-actin). The relative methylation level was calculated by the formula $[M/(M+U)] \times 100\%$, in which M and U represent the density of the methylation and unmethylation band, respectively. Results represent the percentage of allelic methylation of the tumor.

Mutational Analysis by Genomic Sequencing.

Exons 2 to 22 that span the whole coding region of RASAL1 were polymerase chain reaction (PCR) amplified, and the sequences were analyzed by Sanger sequencing (see Table 3 for primer sequences). The sequencing and primers for mutation analysis of BRAF, PTEN, PIK3CA, N2-RAS, H2-RAS, and K1-RAS genes are as described previously (27).

Tumor Formation in Nude Mice.

The animals' care was in accord with the guidelines of Johns Hopkins Medical Institutions. K1 cells stably transfected with doxycycline-inducible wild-type RASAL1 or RASAL1 mutants constructed as described above were injected ($1 \times 10^7$ cells/mouse) subcutaneously into flanks of female nude mice at the age of 4 weeks (Harlan Sprague Dawley, Indianapolis, Ind.). Mice were fed vehicle or 0.2 mg/mL doxycycline, which was stored in a 0.5% sucrose solution in light-proof bottles, beginning when the tumor grew to a size of 2 mm at 1.5 weeks after the inoculation of cells. Tumor size was measured, and volume was calculated using the formula (length×width2)/2. After 5 weeks, mice were sacrificed, and tumors were surgically removed, photographed, and weighed.

Statistical Analysis.

For continuous data with a normal distribution or an abnormal distribution, Student t test and Wilcoxon Mann-Whitney test was used to analyze the statistical significance of differences between two groups, respectively. For categorical data, Fisher exact test was used. All reported P values were two-sided, and P less than 0.05 was considered statistically significant.

Western Blot Analysis.

Cells were lysed in the RIPA buffer supplemented with phosphatase and protease inhibitors (Sigma, St. Louis, Mo.) and protein blot analyses were performed as previously described (Liu et al., 18 CANCER RES. 7311-19 (2009)). The anti-human RASAL1 antibody was from Everestbiotech, Oxfordshire, UK (#EB06176). Other antibodies used in the present study, including anti-phospho-ERK (Sc-7383), anti-ERK1 (Sc-94), anti-phospho-Akt (Sc-7985-R), anti-Akt (sc-8312), anti c-myc (sc-47694), and anti-actin (Sc-1616-R) were all purchased from Santa Cruz Biotechnology (Santa Cruz, Calif.).

RT-PCR Analysis.

RNA extraction and semi-quantitative RT-PCR were performed as previously described (Liu et al., 13(4) CLIN. CANCER RES. 1341-49 (2007)). Normal human thyroid RNA samples (Stratagene, La Jolla, Calif.) were used as the control. The RT-PCR primers are presented Table 3.

Colony Formation Assay.

Colony formation assays were performed as described previously (Liu et al., 92(6) J. CLIN. ENDOCRINOL. METAB. 2264-71 (2007)). For colony formation in monolayer culture, transfected cells ($1 \times 10^5$ cells/well) were inoculated into a 6-well plate, and 24-h later cells were selected with blasticidin (2 µg/mL) for 2 weeks. Surviving colonies were counted after staining with crystal violet. For colony formation in soft agar, cells ($5 \times 10^3$ cells/well) were plated in RPMI 1640 containing 10% FBS and 0.33% agar in 12-well plates. After 3-4 weeks of culture, colonies were photographed and colony number was counted under a microscope.

RAS Pull-Down Assays.

The protocol for cell treatment was as described previously (Walker et al., 23(8) EMBO J. 1749-60 (2004)). Briefly, cells were serum starved for 2 h in serum-free medium at 24h post-transfection of wild-type H-RAS. Cells were then treated with 50 µM ATP for 1 min. A RAS activation assay kit (Cell Biolabs, San Diego, Calif.) was used to assess RAS activity. After treatment, cells were washed twice with ice-cold PBS and then lysed in 1 mL of assay lysis buffer. After centrifugation at 14,000×g for 10 min at 4° C., cell lysates were incubated at 4° C. for 1 h with 40 µL of the RAF1 RAS-binding domain-agarose beads. The beads were pelleted and washed three times with assay lysis buffer, and then resuspended in 2× reducing SDS-PAGE sample buffer. The quantities of activated RAS (RAS-GTP) were analyzed by Western blotting using anti-RAS monoclonal antibody.

Plasmids and Cell Transfection.

RASAL1 cDNA, which was amplified from normal thyroid (Stratagene, La Jolla, Calif.) and tagged with c-myc epitope, was inserted into a modified lenti-virus vector that was derived from plenti6/V5-DEST (Invitrogen, Grand Island, N.Y.). The virus packaging and cell infection were performed as described previously (Liu et al., 18 CANCER RES. 7311-19 (2009)). To construct the plasmid for doxycycline-inducible expression of RASAL1, the CMV promoter in the modified plenti6/V5-DEST plasmid was replaced with the Xho I-EcoR V fragment of plasmid pUHG10-3 (Gossen et al., 89(12) PROC. NATL. ACAD. SCI. USA 5547-51 (1992)), which contained hCMV minimal promoter with heptamerized upstream tet-operators. The K1 cell line was transfected with plasmid pUHD 172-1 neo to express the rTetR-VP16 fusion protein (Gossen et al., 268(5218) SCIENCE 1766-69 (1995)) before the line was used for inducible expression of RASAL1. Oligonucleotide-directed mutagenesis of RASAL1 was performed using a QuikChange mutagenesis kit (Stratagene, La Jolla, Calif.) according to the manufacturer's instructions (see Table 3 for primers).

Results

Screening for Potential Candidate TSGs in Thyroid Cancer Cells.

Figure 1B:
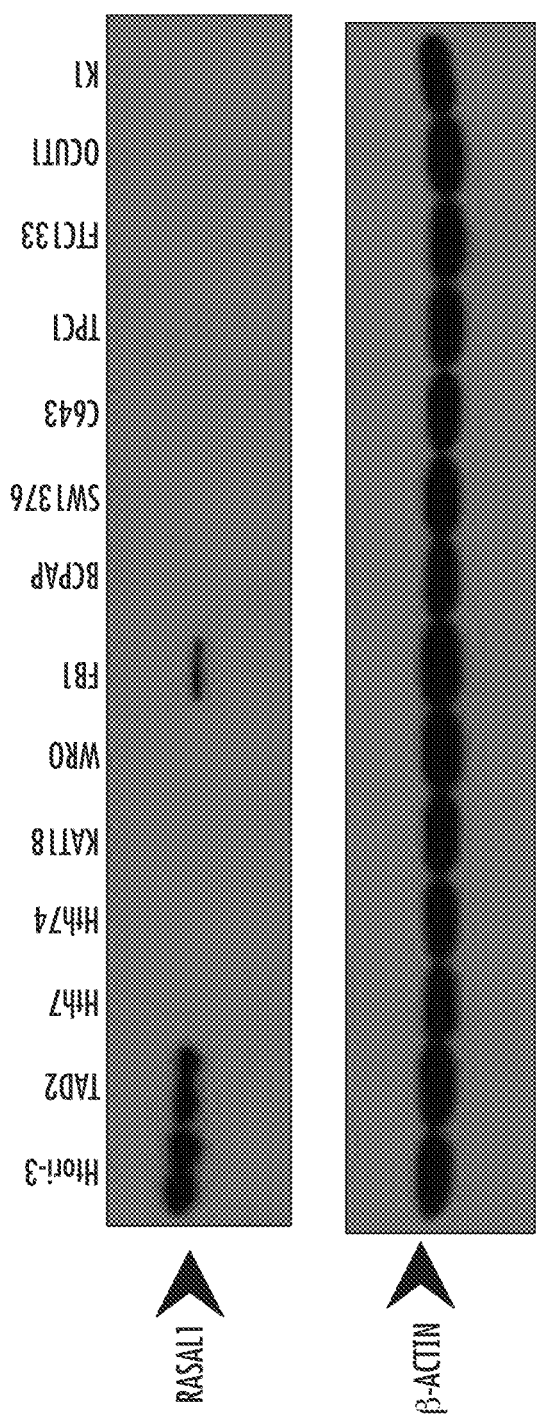

A common feature of TSGs in human cancer is aberrant silencing, so we initially screened for potential candidate TSGs involved in the modulation of RAS signaling by examining the expression pattern of the negative modulators of the pathway. RASSF1A and PTEN are two negative modulators that are known to be downregulated in thyroid cancer (26,30,31). Here we examined the expression of another 13 negative modulators of the RAS signaling pathway that are candidate human TSGs by RT-PCR analysis of a cDNA panel derived from 12 human thyroid cancer cell lines (Table 2). Among these, the expression of two RasGAP genes, RASAL1 and DAB2IP, was silenced in 11 and seven of the 12 thyroid cancer cell lines, respectively, whereas they were abundantly expressed in a normal human thyroid tissue pool derived from five persons and two immortalized normal human thyroid epithelial cell lines (Htori-3 and TAD2) (FIG. 1A). In contrast, the genes for the remaining 11 negative modulators of the RAS signaling pathway (NF1, SPRY1, SPRY2, SPRED1, SPRED2, RKIP, DUSP5, DUSP6, TSC1, TSC2, LKB1) were expressed in all of the thyroid cancer cell lines, except for K1 cells, in which TSC2 was not expressed. We were particularly interested in RASAL1 because its mRNA expression was completely lost in all of the thyroid cancer cell lines except for FB1 (FIG. 1A), which was confirmed by the corresponding loss of the expression of RASAL1 protein (FIG. 1B). Like mRNA, normal expression of RASAL1 protein was also seen in normal thyroid cell lines Htori-3 and TAD2 and thyroid cancer cell line FB1.

Figures 2A, 2B:
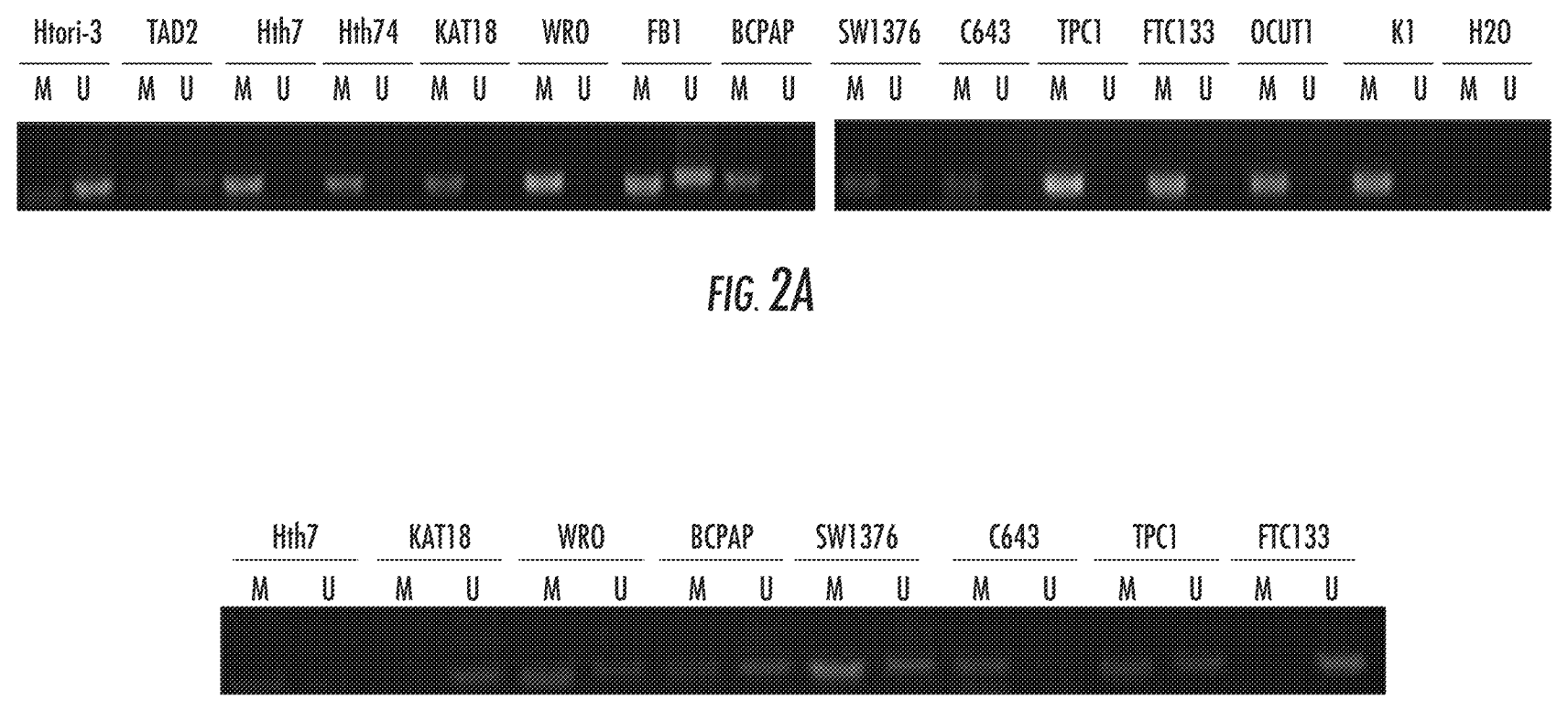
Figure 2C:
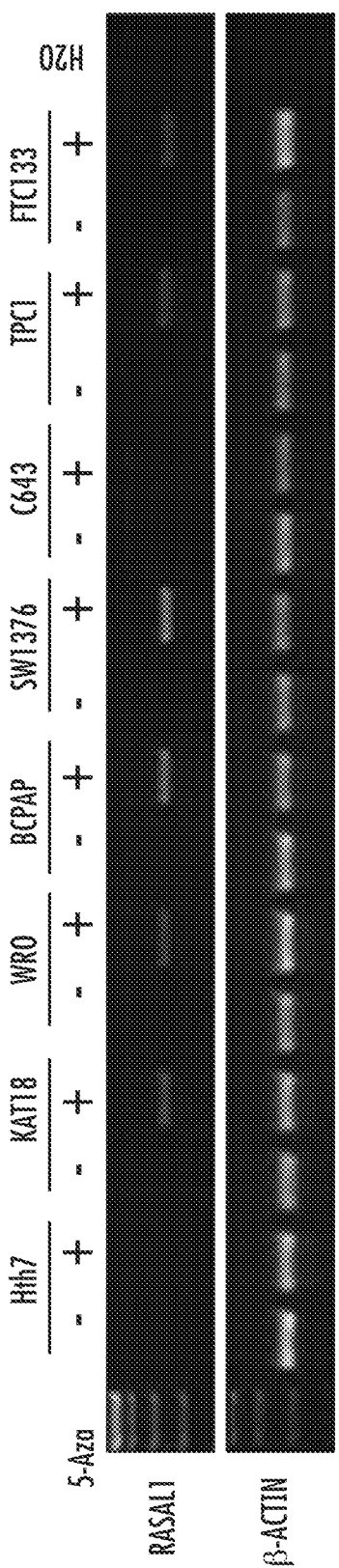

Another common feature of TSGs is their aberrant hypermethylation in the promoter and 5' regions, as exemplified by PTEN and RASSF1A in thyroid cancer (30,31). We found that the RASAL1 promoter region was completely methylated in 11 thyroid cancer cell lines that lost the expression of RASAL1, whereas it was only partially methylated in the two normal thyroid cell lines and cancer cell line FB1 that expressed RASAL1 (FIG. 2A). Treatment of cells with demethylating agent 5-aza-2-deoxycytidine (5-Aza) induced demethylation of RASAL1 (FIG. 2B) and restored its expression (FIG. 2C) in six of the eight thyroid cancer cell lines tested, suggesting that promoter methylation was a mechanism for the loss of RASAL1 expression in thyroid cancer cells.

Figure 2D:
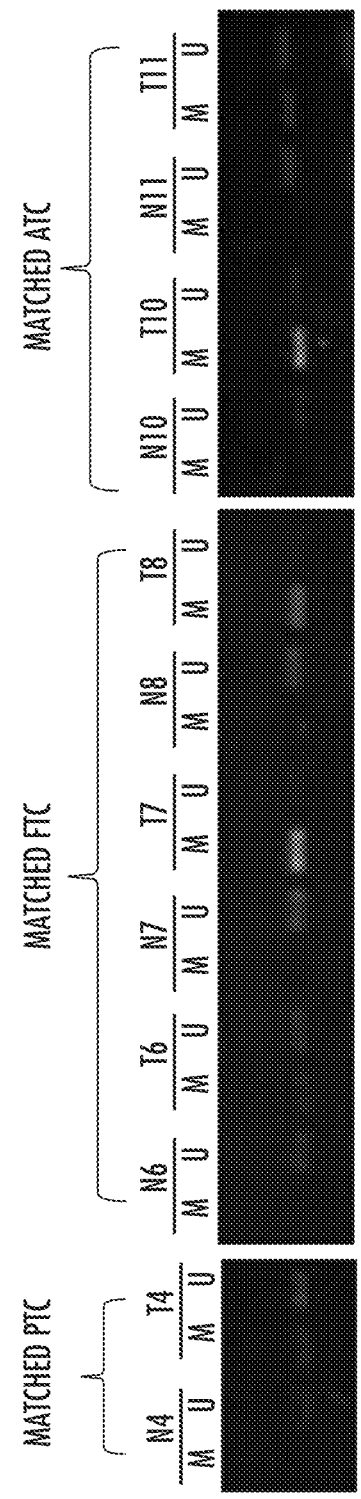
Figure 2E:
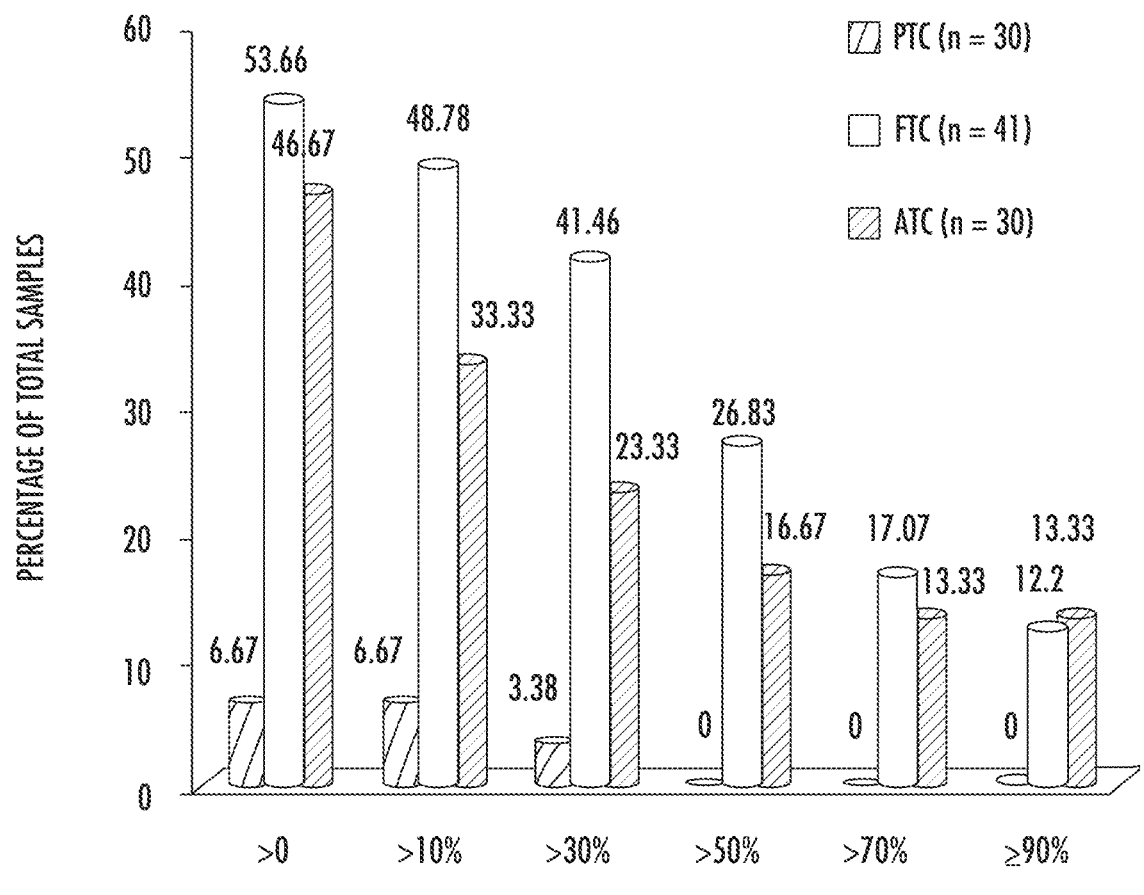
Figure 3A:
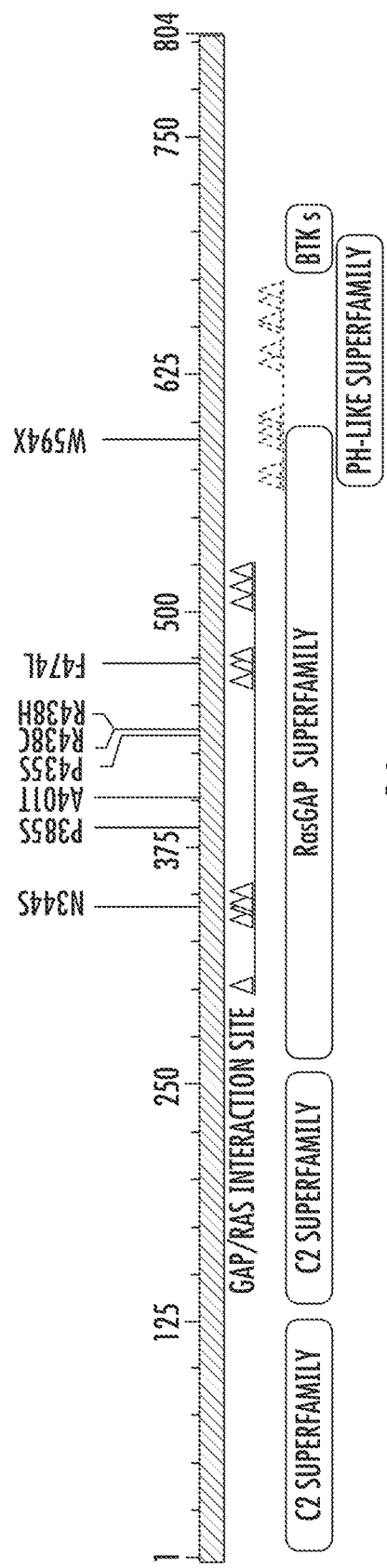
FIG. 3A-3C. Analysis of the relationship between mutations and hypermethylation of RASAL1 and the collective rates of the two events in thyroid cancer. A) Shown are the functional domains of RASAL1, including the RasGAP domain where all eight RASAL1 mutations are located. The amino acid numbers of the RASAL1 protein (shown as a black bar) are shown above the black bar. The annotation of RASAL1 domains, which was generated by the National Center for Biotechnology Information (NCBI) online tool Conserved Domain Search (http://www.ncbi.nlm.nih.gov/Structure/cdd/wrpsb.cgi), is presented under the black bar at corresponding sites. B) Mutation and methylation of RASAL1 in individual cases of various types of thyroid tumor. The y-axis represents the allelic percentage of RASAL1 methylation of an individual tumor. Each individual case of thyroid tumor is represented by a circle, with solid circles representing the cases positive for RASAL1 mutation. Mutation-positive cases generally had low methylation levels, indicating an inverse relationship between the genetic and epigenetic alterations of RASAL1. P values were calculated by Wilcoxon Mann-Whitney test for comparison of the methylation levels between different types of thyroid cancer. C) Rates (percentage of total samples of each tumor type) of collective RASAL1 alterations (mutation and hypermethylation). Two cutoff values (50% and 70%) were used to define the level of RASAL1 methylation. ATC=anaplastic thyroid cancer; FTC=follicular thyroid cancer; PTC=papillary thyroid cancer.
Figure 3B:
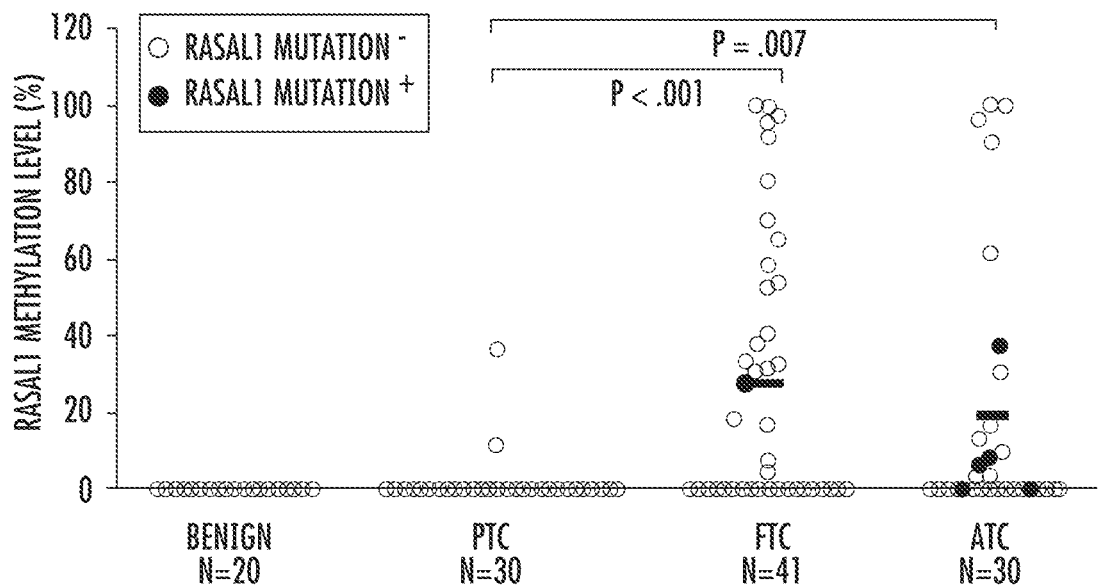

We next investigated the methylation status of RASAL1 in thyroid tumors. We first examined 13 primary thyroid cancers with matched normal thyroid tissues. We found RASAL1 methylation in six thyroid cancers (n=1 of 5 PTCs, n=3 of 4 FTCs, and n=2 of 4 ATCs) but no methylation in any of the matched normal thyroid tissues (FIG. 2D). MSP analysis of an additional 88 thyroid tumor samples showed that RASAL1 was hypermethylated predominantly in FTC and ATC no matter what methylation levels were used as cutoff values (FIG. 2E). If a level of greater than 50% allelic methylation was used, which means that at least in some cells of the tumor both alleles of RASAL1 are methylated, 26.83% (n=11 of 41) of FTCs and 16.67% (n=5 of 30) ATCs met this cutoff point but no PTCs did. No RASAL1 methylation at all was seen in 20 benign thyroid tumors, and the average methylation level of RASAL1 in PTC was statistically significantly lower than that in ATC (1.59±6.88 vs 19.32±33.79; P=0.007) or FTC (1.59±6.88 vs 27.97±34.75; P<0.001) (FIG. 3B). Thus, epigenetic impairment of RASAL1 was a common event in thyroid cancers, particularly in FTC and ATC.

Identification of RASAL1 Mutations in Thyroid Cancers.

The above findings strongly suggest that RASAL1 is an important TSG in thyroid cancer. Because mutations are a classical mechanism in the impairment of TSGs and no RASAL1 mutations are currently known in human cancers, we next sought RASAL1 mutations as genetic support for the TSG candidacy of RASAL1 in thyroid cancer. We sequenced all 21 exons of RASAL1 that span its whole coding region on genomic DNA from 101 primary thyroid cancer samples. We found seven missense mutations and one nonsense mutation in eight thyroid cancers, including one of 30 PTCs (3.33%), two of 41 (4.88%) FTCs, and five of 30 (16.67%) ATCs, which were all located in the RAS GTPase-activating domain of RASAL1 (FIG. 3A; Table 1; and Table 4; see also Supplementary FIG. 2 (not shown, but available online)). All the mutations were confirmed by repeating the amplification PCR and bidirectional sequencing. No RASAL1 mutation was found in 20 benign thyroid tumors. Six of the eight mutations were C→T or G→A transitions, including three (37.5%) transitions that occurred at CpG dinucleotide sequences (Table 1). In addition, six of the eight mutations occurred at the site of short direct repeats.

Amino acid sequence alignment analysis of the RAS GTPase activating domains derived from six human RasGAPs showed that six of the seven missense mutations of RASAL1 were located at conserved sites, which is similar to the missense mutations of NF1, another RasGAP, in human cancers (data not shown). On the similarity plot that was generated on the basis of the multiple alignment of RASAL1 homologues from 18 species, we observed that the RASAL1 missense mutations were situated on top of the similarity peaks in regions of high similarity (data not shown).

Figure 3C:
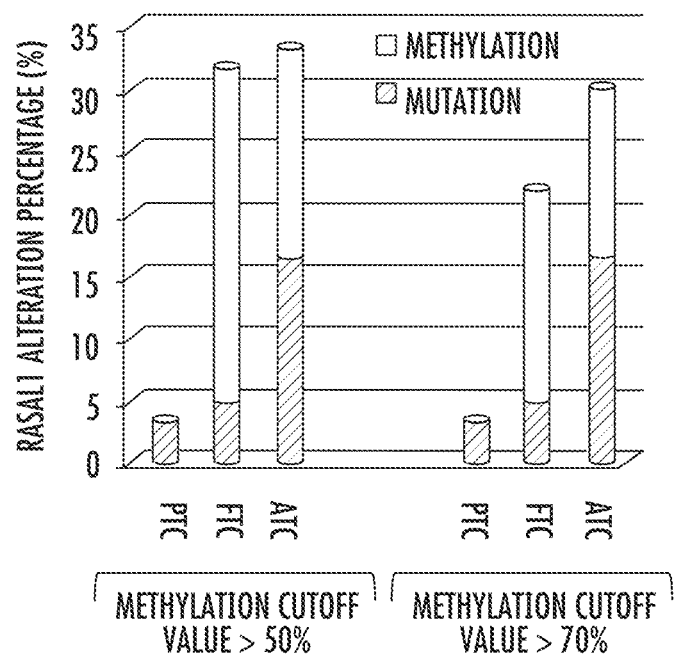

There was a reciprocal relationship between mutations and the methylation of RASAL1. None of the thyroid cancers harboring RASAL1 mutations had RASAL1 methylation level higher than 50%; in fact, most of the RASAL1 mutation-positive cancers had RASAL1 methylation levels lower than 20% (FIG. 3B). This was in contrast with the RASAL1 mutation-negative cancers, in which high levels of RASAL1 methylation were common and many had a methylation level greater than 50%. Thus, mutation and hypermethylation of RASAL1 were mutually exclusive, suggesting that either the genetic or epigenetic alteration of this gene was sufficient for its role in tumorigenesis. When both RASAL1 mutation and allelic methylation level of greater than 50% were counted, the genetic and epigenetic alterations were collectively found in 3.22% (n=1 of 31) of PTCs, 31.70% (n=13 of 41) of FTCs, and 33.33% (n=10 of 30) of ATCs (FIG. 3C). This FTC- and ATC-preferential distribution pattern of genetic and epigenetic alterations of RASAL1 remained even under a methylation cutoff value of greater than 70%

Relationship Between RASAL1 Alterations and Classical Mutations in RAS-Coupled Signaling Pathways.

Figure 4A:
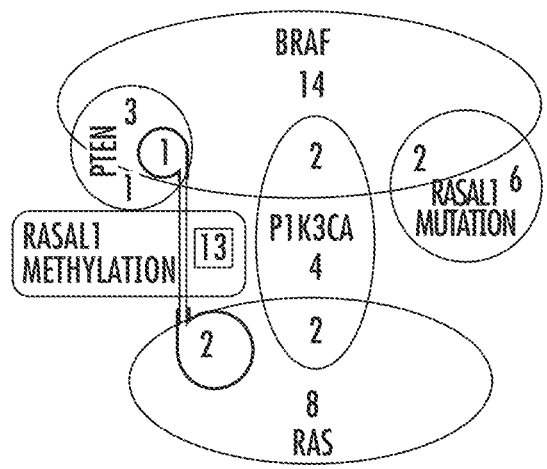
FIG. 4A-4G. Analysis of the relationship between RASAL1 alterations and mutations of classical genes in the RAS signaling pathway. A) Schematic illustration of the mutual exclusion of hypermethylation and mutations of RASAL1 with mutations of classical genes (RAS, BRAF, PIK3CA, and PTEN) in the RAS signaling pathway analyzed on 101 thyroid cancer samples (30 papillary thyroid cancer, 41 follicular thyroid cancer, and 30 anaplastic thyroid cancer). A methylation level greater than 50% was the cutoff value for RASAL1 methylation. Each shape with different color represents one gene alteration as indicated inside the shape. The overlap regions of the shapes represent the samples that contain two or more indicated gene alterations. All of the gene alterations are mutations, except for RASAL1, which also has hypermethylation as indicated. The number of tumor samples with the indicated gene alteration is represented by white printed numbers in each case. B) Association of RASAL1 methylation with mutations of genes in the PI3K pathway. Four cutoff allelic methylation values, as indicated on the x-axis, were used to define RASAL1 methylation levels. The y-axis represents the percentages of cancer samples that reached the indicated RASAL1 methylation level indicated on the x-axis. The empty bars (PI3K−) represent samples negative for mutations in RAS, PIK3CA, or PTEN in the PI3K pathway, and the solid bars (PI3K+) represent samples positive for mutations in RAS, PIK3CA, or PTEN in the PI3K pathway. C) Inverse association of RASAL1 methylation with mutations of genes (RAS or BRAF) in the MAPK pathway. The empty bars (MAPK−) represent samples negative for mutations in RAS or BRAF in the MAPK pathway, and the solid bars (MAPK+) represent samples positive for mutations in RAS or BRAF in the MAPK pathway. The remaining definitions are the same as those in (B). D) Inverse association of RASAL1 methylation with mutations of genes (RAS, PIK3CA, PTEN, or BRAF) in the RAS-signaling pathway (including both PI3K and MAPK pathways). The empty bars (RAS signaling−) represent samples negative for mutations in RAS, PIK3CA, PTEN, or BRAF in the RAS signaling pathway, and the solid bars (RAS signaling+) represent samples positive for mutations in RAS, PIK3CA, PTEN, or BRAF in the RAS signaling pathway. The remaining definitions are the same as those in (B). E-G) Inverse association of RASAL1 alterations (collectively including both RASAL1 methylation and mutations) with gene mutations in the PI3K pathway (E), MAPK pathway (F), or RAS signaling pathway (G) as defined for (B), (C), and (D), respectively. The y-axis in (E), (F), and (G) represents the percentage of tumor samples that were collectively positive for RASAL mutations or the methylation levels indicated on the x-axis. The remaining definitions are the same as those in (B). In each panel of FIG. 4, the upper portion shows the cases with RASAL1 methylation less than the level indicated on the x-axis, and the lower portion shows the cases with RASAL1 methylation equal to or greater than the level indicated on the x-axis. Comparisons of the upper and lower groups in each of panels (C-G) were performed using two-tailed Fisher exact test, and those that were statistically significant are indicated with specific P values in the figure.
Figure 4B:
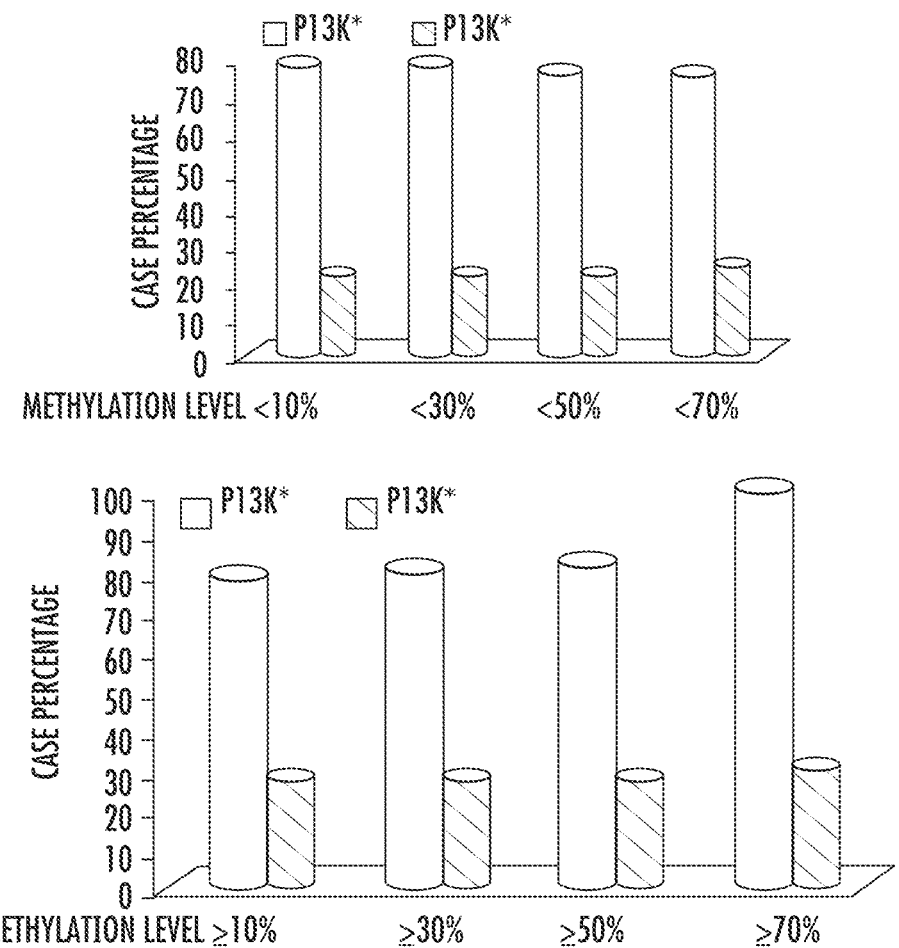
Figure 4C:
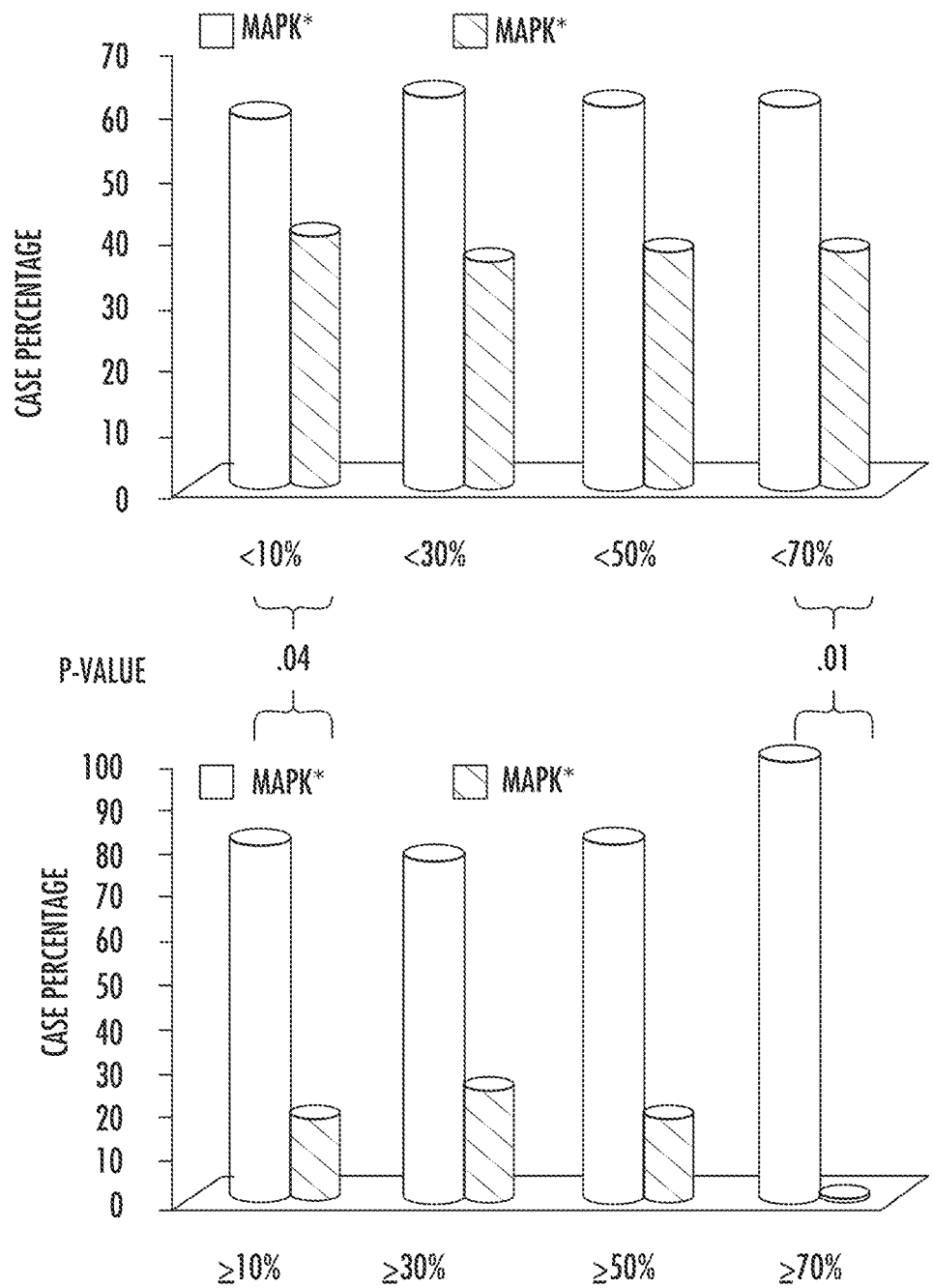
Figure 4D:
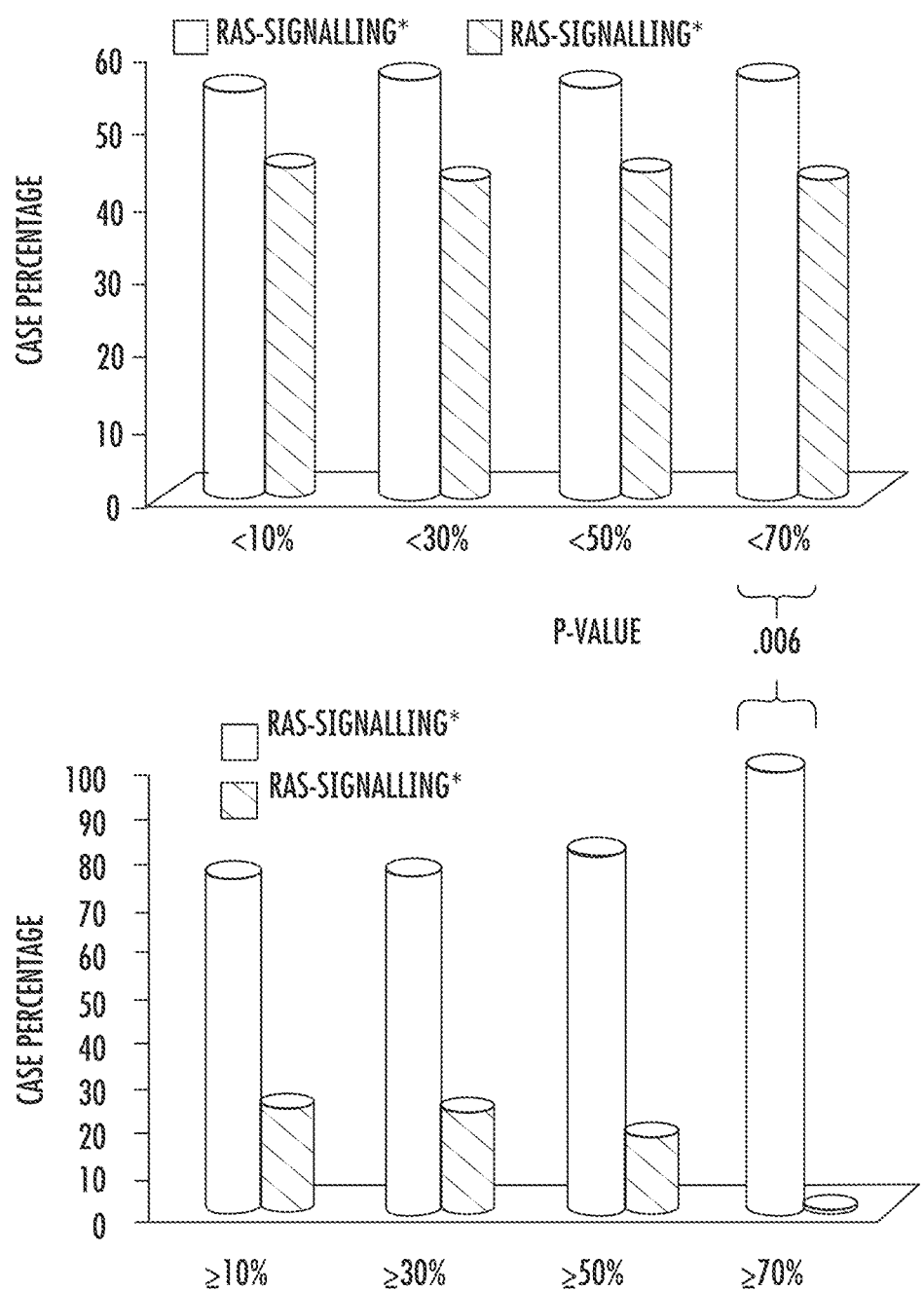
Figure 4E:
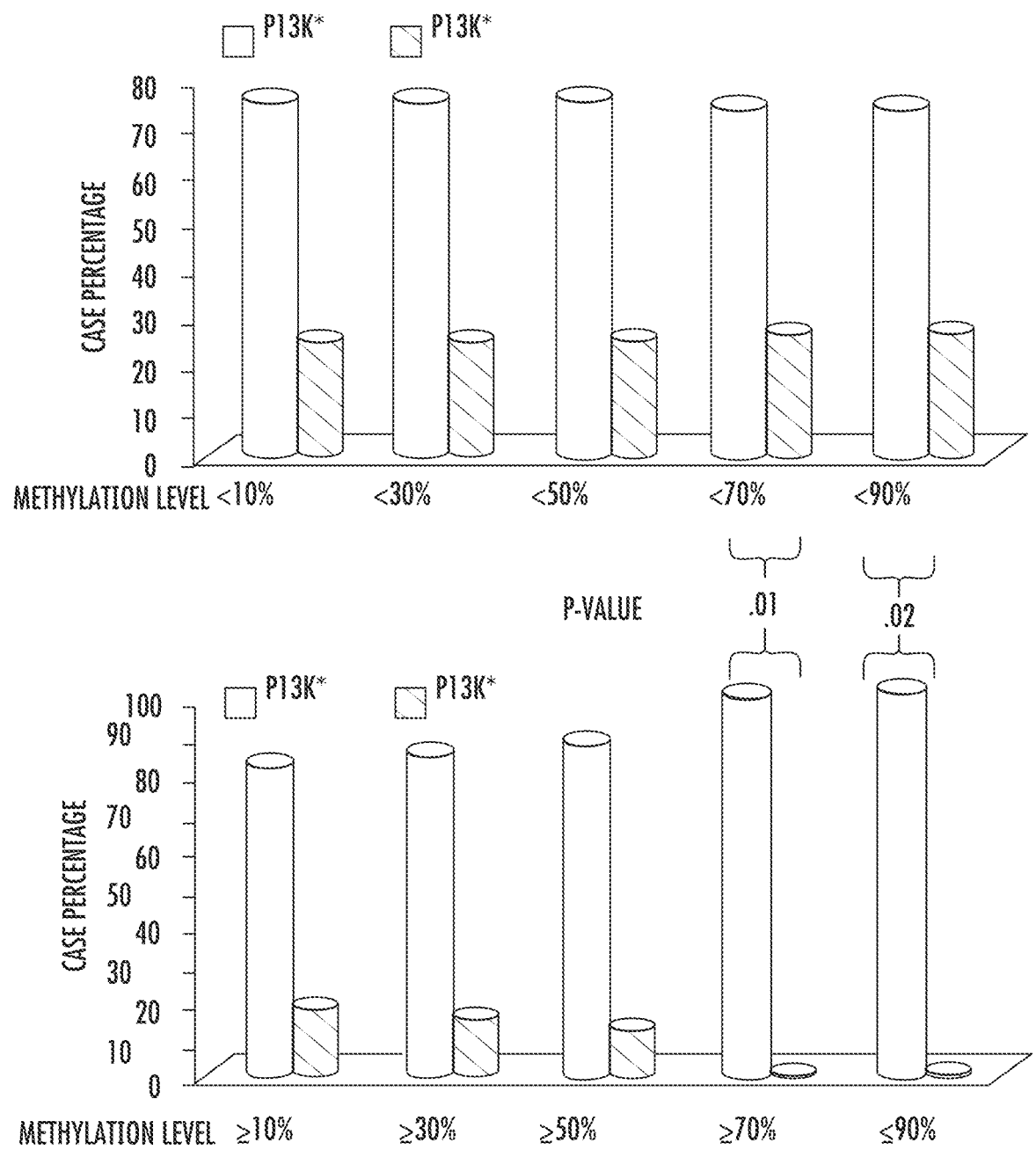
Figure 4F:
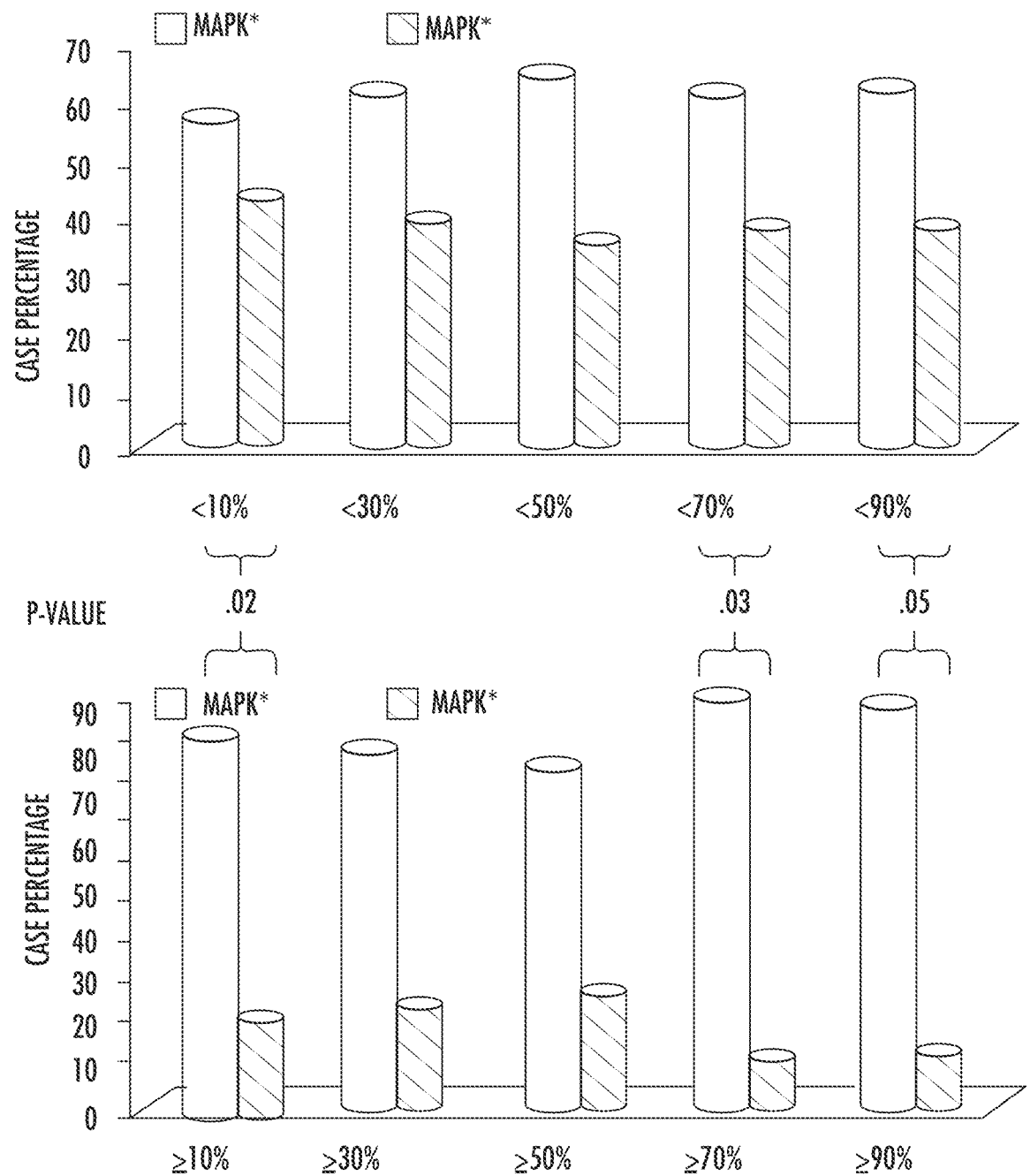
Figure 4G:
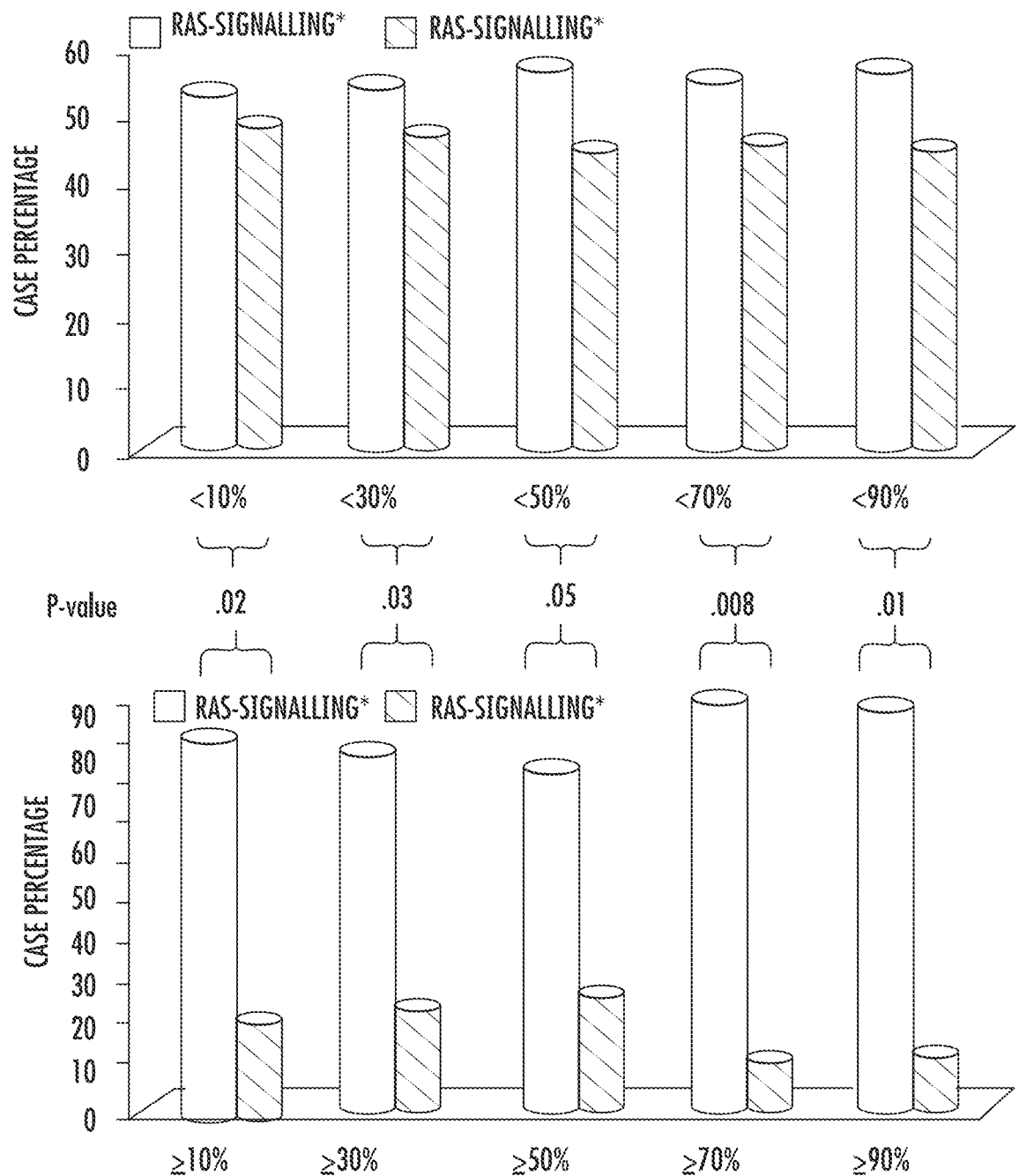

We examined the relationship between RASAL1 alterations and hotspot mutations of six classical genes in RAS-coupled MAPK and PI3K pathways, including BRAT PTEN, PIK3CA, and the three RASs in 101 thyroid cancer samples. We found that five of 24 (20.83%) tumors carrying RASAL1 mutation or methylation at high levels (>50%) vs 34 of 77 (44.16%) tumors carrying no RASAL1 mutation or methylation at low levels (<50%) harbored any of the classical mutations in the six genes (P=0.02, Fisher Exact test) (Table 4). This preferential distribution pattern revealed a largely mutually exclusive relationship between RASAL1 alterations and the classical mutations in RAS pathways. This relationship is also illustrated in FIG. 4A. We further classified the six classical RAS-signaling pathway-related genes into three pathway groups, including PI3K, MAPK, and RAS pathways, as defined in the legend to FIG. 4, and analyzed the relationship between RASAL1 alterations and the genetic alterations in the three pathway groups. As shown in FIG. 4, B-D, with increasing the cutoff values of methylation level, tumors carrying RASAL1 methylation showed a decreasing rate of concurrence with mutations in all of the three pathways. A statistically significant mutual exclusivity was always achieved between the RASAL1 methylation and the alterations in MAPK and RAS pathways at a 90% cutoff value of methylation (P=0.01 and 0.005, respectively). A similar mutually exclusive relationship was also observed between the collective RASAL1 alterations (either methylation at 90% cutoff value or mutation) and the mutations in the PI3K, MAPK, and RAS pathways (P=0.02, 0.05, and 0.01, respectively at 90% cutoff value for methylation level) (FIG. 4, E-G).

Functional Characterization of RASAL1 and Its Mutations in Thyroid Tumorigenesis.

Figure 5A:
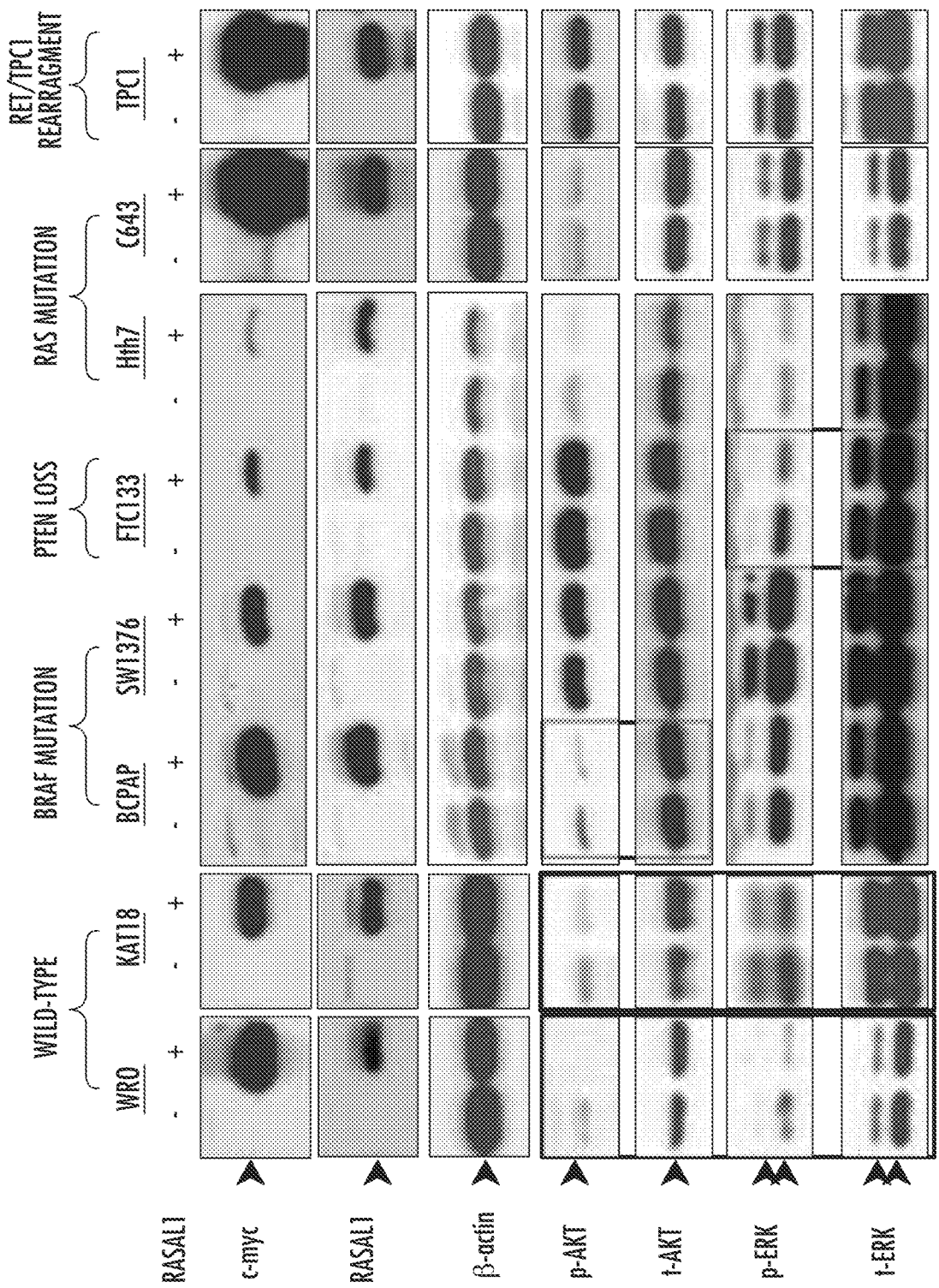
FIG. 5A-5D. Examination of the effects of reintroduction of RASAL1 on RAS signaling and growth of thyroid cancer cells. A) A representative result of Western blotting analysis of RASAL1 expression and phosphorylation of ERK and Akt as well as other related proteins as indicated in various thyroid cancer cell lines that harbor different genetic alterations. B) A representative result of colony formation of thyroid cancer cells in monolayer culture after transfection of plasmids with or without insertion of RASAL1 cDNA followed by drug selection for 2 weeks. Cell colonies were stained with crystal violet. Scale bar=1 cm. C) Western blotting analysis of RASAL1 expression and phosphorylation of ERK and Akt and related proteins as indicated in three selected thyroid cancer cell lines stably transfected with RASAL1. D) Bar graph presentation of the colony numbers (mean±standard deviation) from three experiments for cells stably transfected with empty vectors or RASAL1 as in (C). Only cell colonies containing more than 50 cells were included. Statistically significant P values (two-sided Student t test) are shown where indicated in the figure.

To further test the role of RASAL1 in thyroid tumorigenesis, we investigated its biological functions in various thyroid cancer cell lines. We cloned RASAL1 cDNA and constructed expression vectors to test the impact of induced expression of RASAL1 on the MAPK and PI3K signaling pathways and cellular behaviors. FIG. 5A shows the effects of RASAL1 on the phosphorylation of the downstream signaling molecules ERK and AKT of the MAPK and PI3K pathways, respectively; these effects of RASAL1 were cell type and classical mutation type dependent. Specifically, acute expression of RASAL1 decreased both pERK and pAkt levels in WRO and KAT18 cells, which harbored wild-type RAS, BRAF, PIK3CA, and PTEN, whereas expression of RASAL1 only reduced pAKT but not pERK in BCPAP cells, which harbored BRAF mutation, resulting in activation of the MAPK pathway, and reduced pERK but not pAKT in FTC-133 cells, which harbored PTEN mutation, resulting in activation of the PI3K pathway. No effect was observed in C643 and Hth7 cells, which harbored RAS mutation that could activate both MAPK and PI3K pathways. There was also no effect of RASAL1 expression in TPC1 cells harboring RET-PTC1 rearrangement that could also activate both MAPK and PI3K pathways (32). No effect was observed in SW1736 cells, which harbored BRAE mutation. Whether SW1736 also harbors PI3K pathway-activating genetic alterations is unknown. Thus, overall, RASAL1 suppressed the MAPK pathway or PI3K pathway when it was not activated by classical genetic alterations in thyroid cancer cells.

Figure 5B:
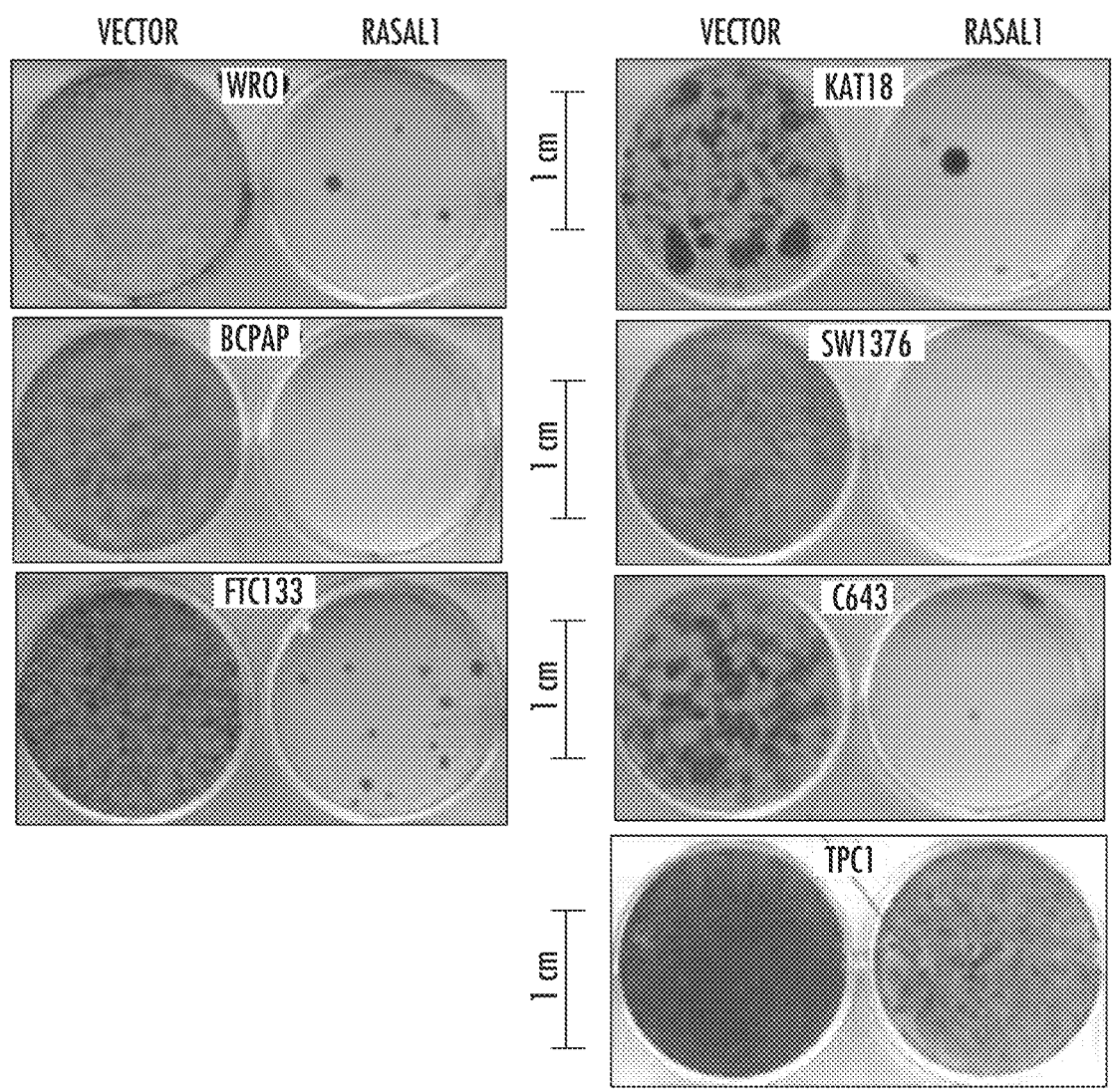
Figure 5C:
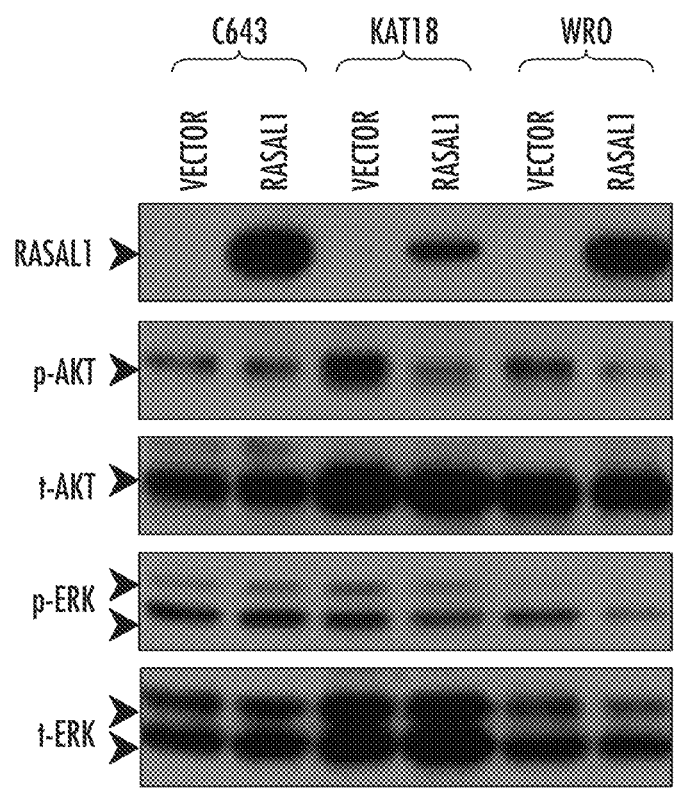
Figure 5D:
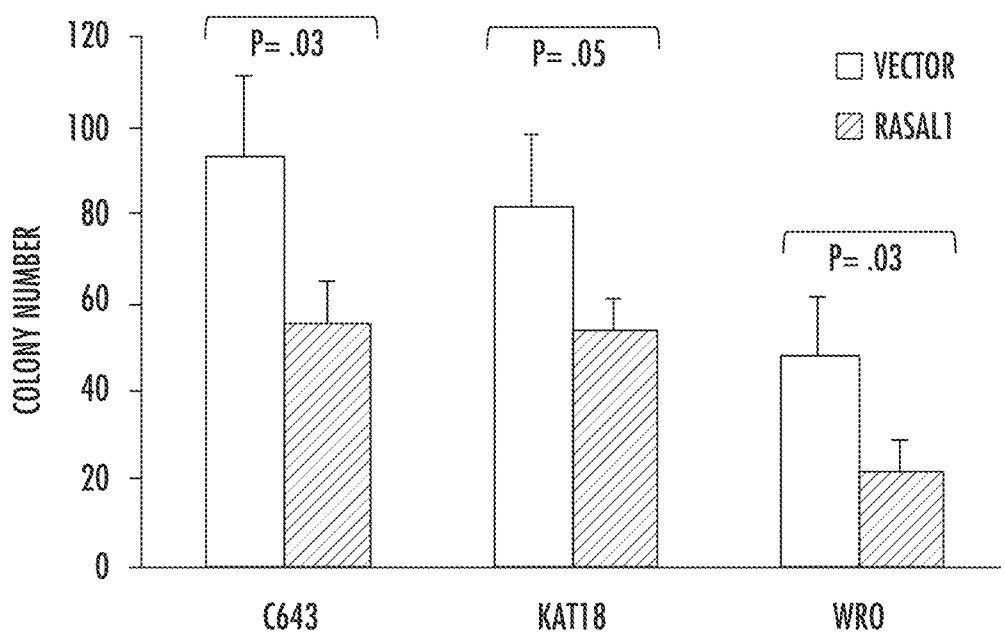

Compared with the control vector, transient reintroduction of RASAL1 dramatically inhibited cell colony growth in monolayer culture in six of seven thyroid cancer cell lines tested (FIG. 5B). We also generated three cell pools with stable expression of RASAL1 (FIG. 5C). Among these, inhibition of pERK and pAKT was observed in KAT18 and WRO cells (FIG. 5C), as seen with transient expression of RASAL1 (FIG. 5A). Anchorage independent cell growth was statistically significantly suppressed in all three stably transfected thyroid cancer cell lines. Specifically, the colony numbers for control vector vs RASAL1 transfection were 92.67±18.15 vs 55.33±9.71, (P=0.03) for C643; 81.67±16.29 vs 54.00±6.56 (P=0.05) for KAT18; and 48.00±13.45 vs 21.67±6.35 (P=0.03) for WRO cells (n=3 in all cases) (FIG. 5D).

Figure 6A:
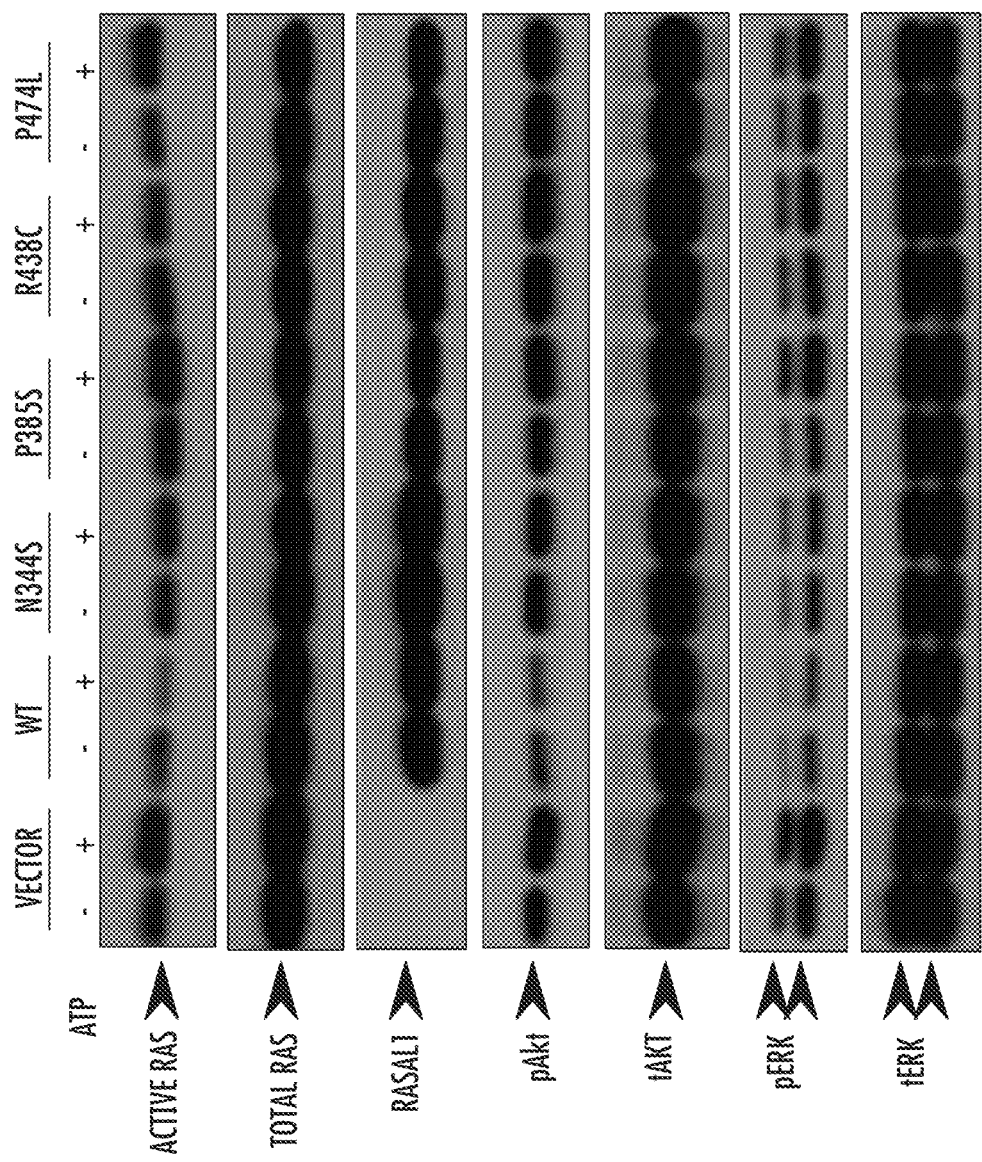
FIG. 6A-6I. Examination of tumor-suppressing functions of the wild-type and mutant RASAL1 in vitro and in vivo. A) Effects of wild-type RASAL1 and various indicated RASAL1 mutants on the activation of RAS in WRO cells. Cells stably transfected with various indicated RASAL1 constructs were treated with or without ATP, and the active RAS (RAS-GTP) was pulled down and analyzed by Western blotting using an RAS Activation Assay Kit as described in the Methods. Cell lysates from the same treatment were also used for Western blotting analysis of pAkt, pERK, and other related proteins as indicated. B) Effects of wild-type and mutant RASAL1 on the colony formation of WRO cells in soft agar. Scale bar=100 μm. C) Bar graph presentation of colony numbers from three experiments (mean±standard deviation) corresponding to (B). Two-tailed Student t test was used for the statistical analysis. D) Western blotting analysis of inducible expression of RASAL1 in K1 cells. The procedures for the construction of doxycycline (Dox)-inducible expression device for RASAL1 and transfection of K1 cells are as described in the Materials and Methods section below. E) Effects of Dox-induced expression of wild-type and mutant RASAL1 on the colony formation of K1 cells. Scale bar=100 μm. F) Bar graph presentation of cell colony numbers from three experiments (mean±standard deviation) corresponding to (E). Two-tailed Student t test was used for statistical analysis. G) Time course of growth of xenograft thyroid tumors that developed in mice after subcutaneous inoculation with K1 cell clones transfected with wild-type RASAL1 or the indicated RASAL1 mutants. Each time point represents the average±standard deviation of the values obtained from four mice in each group. Two-tailed paired Student t test was used to compare tumor sizes at week 5. H) Photographs of the tumors that were surgically removed from mice in each group after they were killed at the end of 5 weeks from the cell inoculation. I) Weight of individual tumors surgically removed from the animals in each group corresponding to (H). The average weight of the tumors from each group is indicated with a short horizontal bar. A statistically significant inhibitory effect of wild-type RASAL1 on tumor growth was observed (P=0.047 on two-tailed paired Student t test), but no such effect was observed for the two indicated RASAL1 mutants.
Figure 6B:
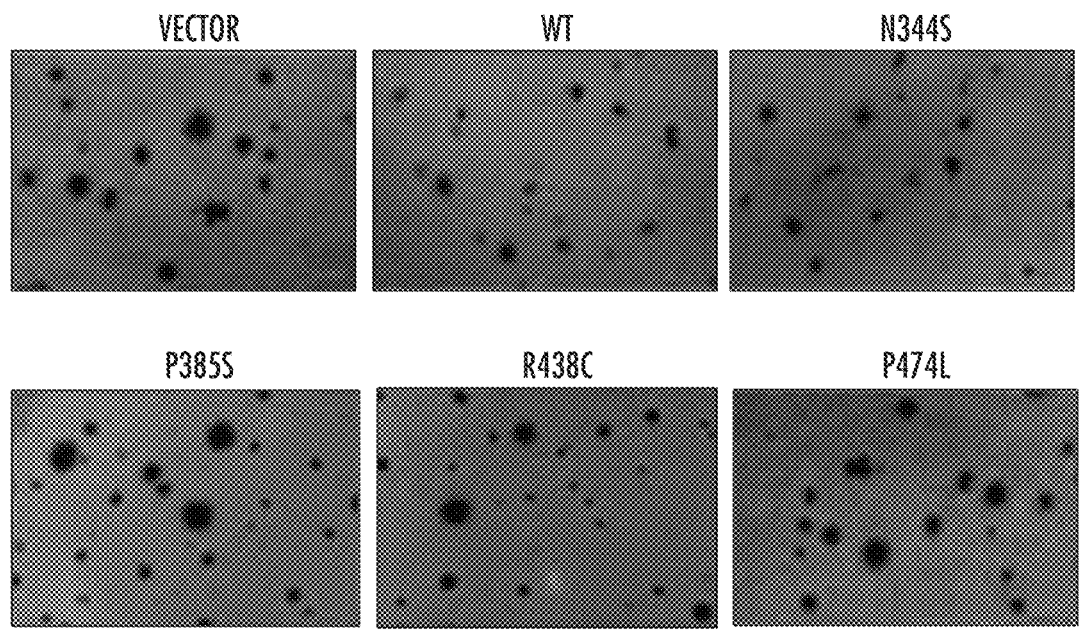
Figure 6C:
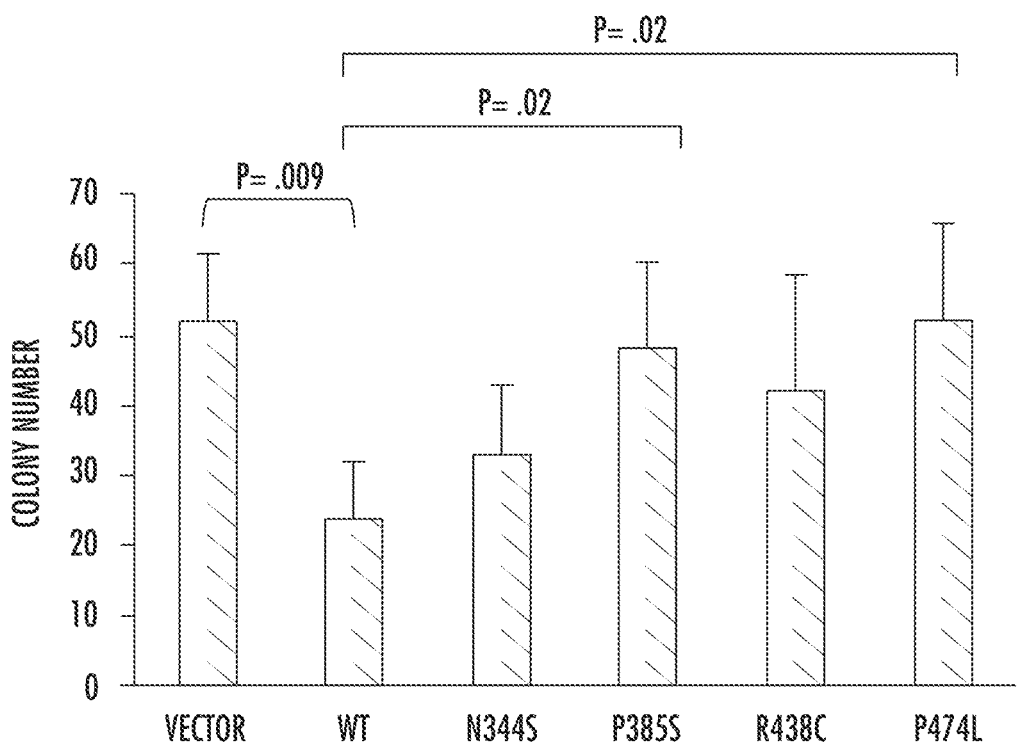
Figure 6D:
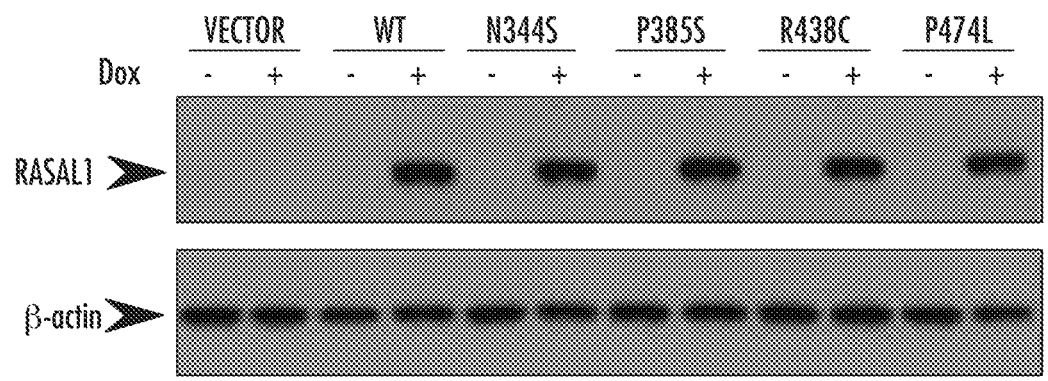
Figure 6E:
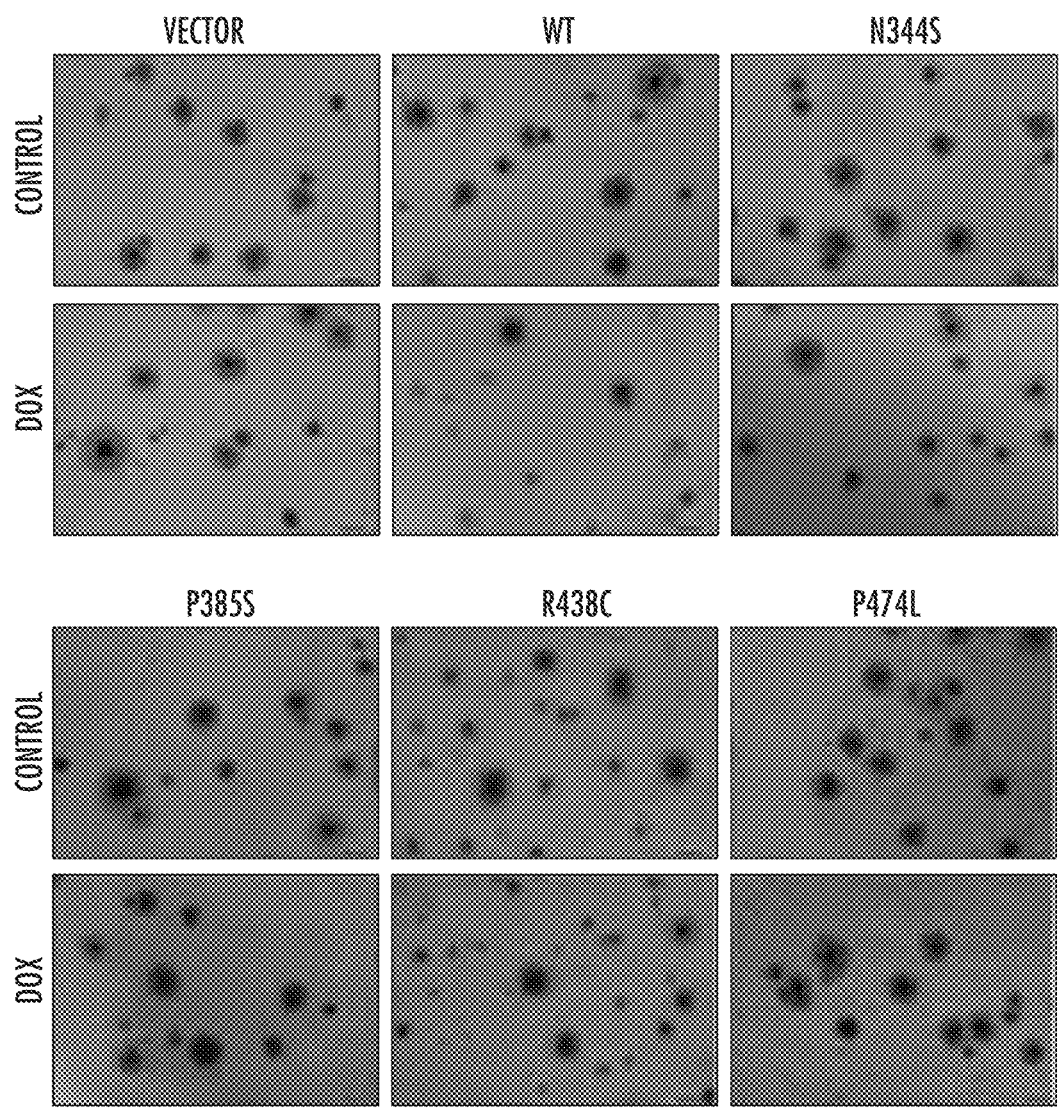
Figure 6F:
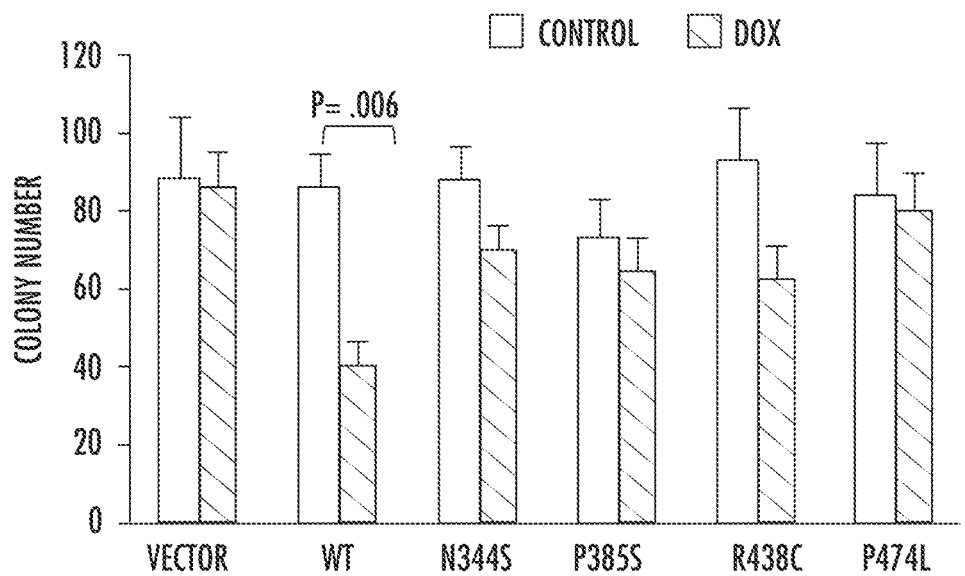
Figure 6G:
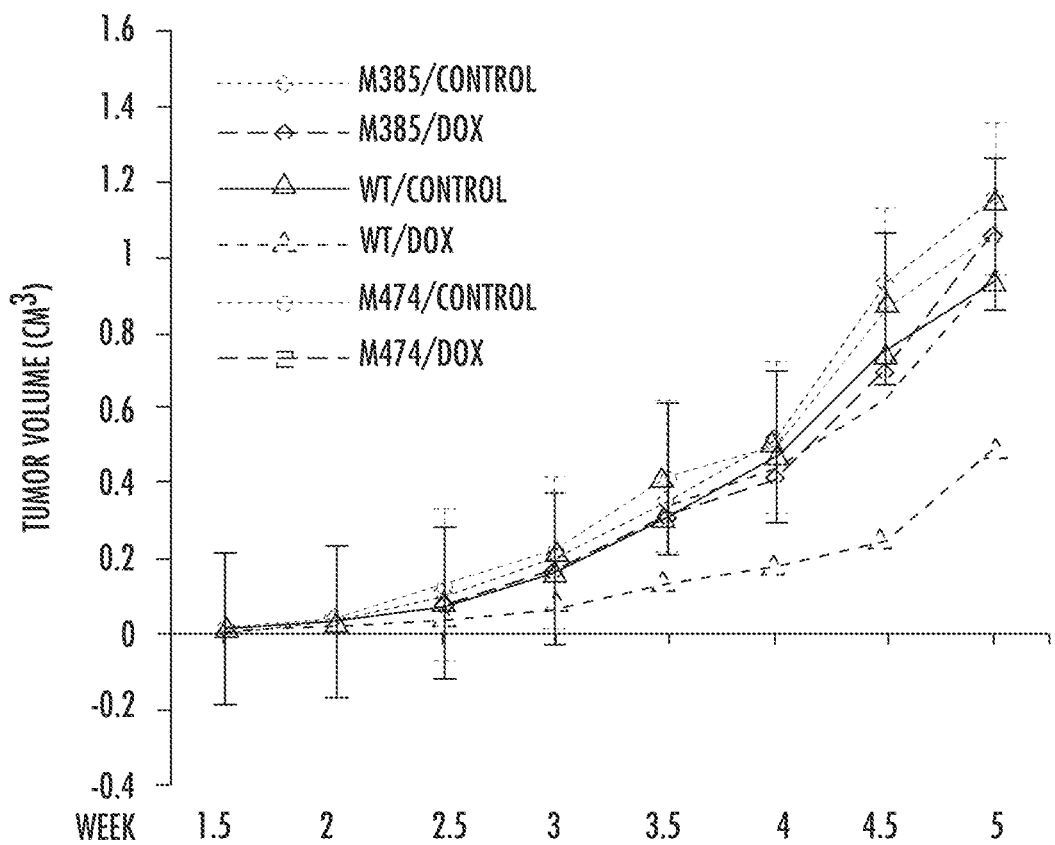
Figure 6H:
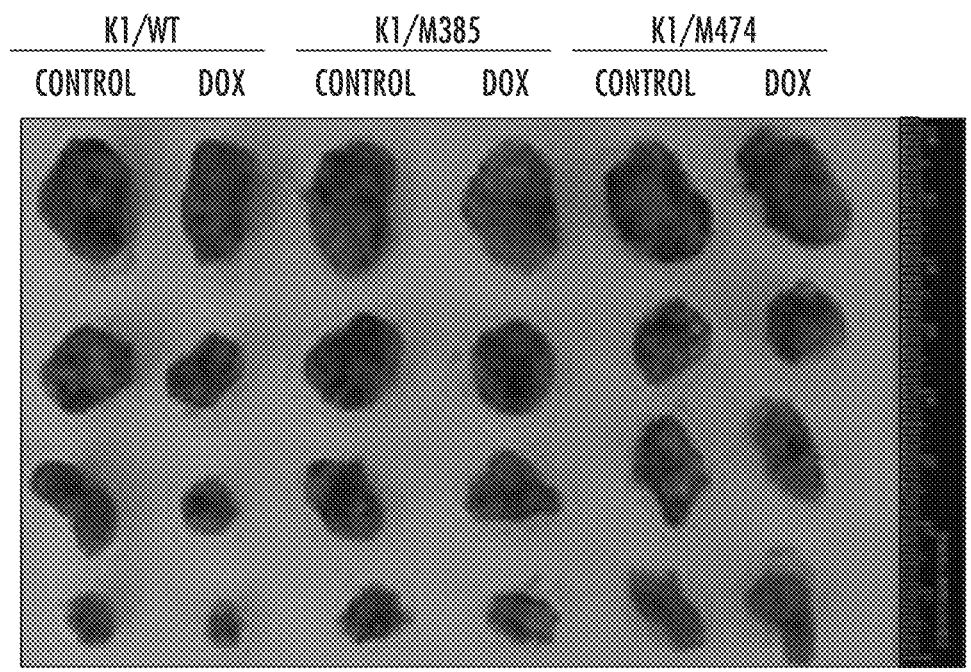
Figure 6I:
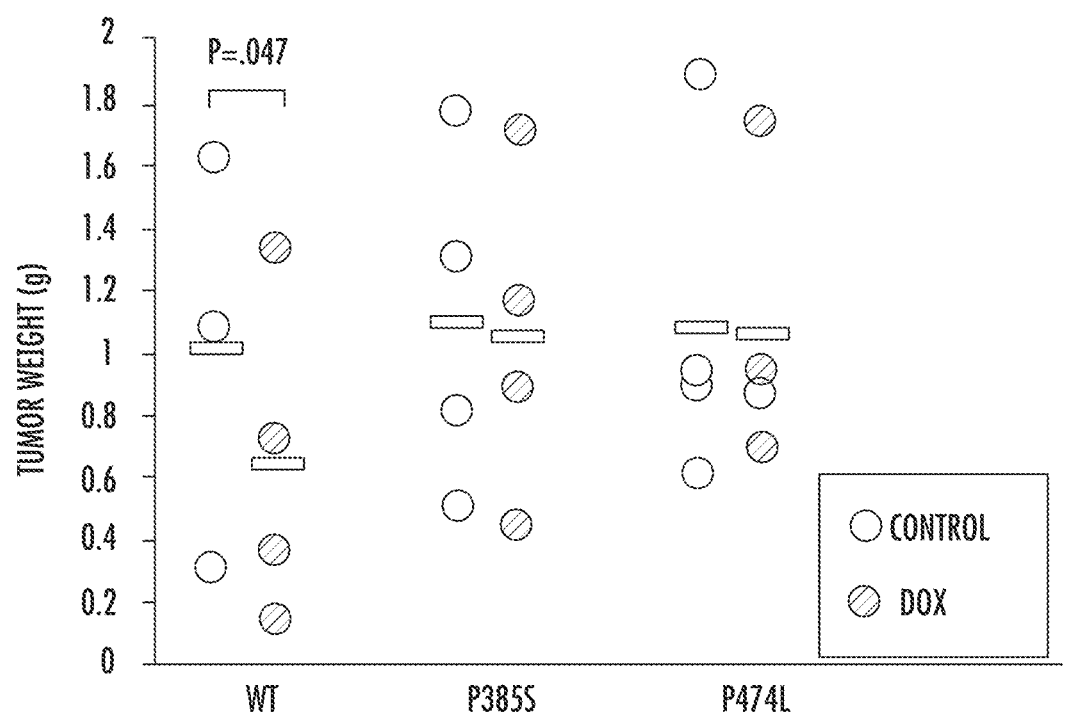

To test the biological relevance of the RASAL1 mutations in thyroid tumorigenesis, we selectively generated four RASAL1 mutants by site-directed in vitro mutagenesis and established WRO cell pools that stably expressed these mutants. Although wild-type RASAL1 suppressed the activation of RAS and the increase in pAKT and pERK stimulated by ATP treatment of cells, RASAL1 mutants P385S and F474L lost such inhibitory functions (FIG. 6A). Correspondingly, these two mutants failed to inhibit the colony formation of WRO cells, which, in contrast, was suppressed by the wild-type RASAL1 (colony number: vector 52.00±9.54 vs wild-type 24.00±7.81; P=0.009) (FIGS. 6, B and C). The other two mutants, N344S and R438C, showed a slight inhibitory effect on RAS activation (FIG. 6A) and cell colony formation (FIGS. 6, B and C), which was weaker than the inhibitory effect of the wild-type RASAL1, suggesting that these two mutations partially impaired the function of RASAL1. To further test the impact of RASAL1 mutations on the function of RASAL1, we established K1 thyroid cancer cell pools with doxycycline-inducible expression of RASAL1 proteins. As shown in FIG. 6D, wild-type RASAL1 and its mutants could be abundantly expressed upon doxycyline treatment of cells. Again, compared with wild-type RASAL1 (colony number: control 86.00±8.54 vs Dox 40.33±6.03; P=0.006), the four mutants displayed varying impairment in their inhibitory effects on K1 cell colony formation, with P474L having almost completely lost the inhibitory function (FIGS. 6, E and F). We finally performed in vivo studies to test the impact of RASAL1 and its mutants on xerograph thyroid tumor growth. Upon doxycycline-induced expression of wild-type RASAL1, the growth of K1 cell-derived xenograft tumors in nude mice was statistically significantly suppressed both in tumor volume (0.94±0.52 cm3 vs 0.49±0.4 cm3; P=0.02) (FIG. 6G) and tumor weight (1.01±0.54 g vs 0.66±0.53 g; P=0.047) (FIGS. 6, H and I). In contrast, RASAL1 mutants P385S and F474L showed no effect on tumor growth.

Discussion

As a negative modulator of the RAS signaling pathway by functioning as a RasGAP that catalyzes RAS inactivation, RASAL1 has been suggested to be a candidate TSG in recent years (3-5). However, direct evidence to demonstrate its tumor suppressor function is lacking. Moreover, there has been no genetic evidence to support RASAL1 as a typical TSG. The relative role of RASAL1 with respect to that of classical genes in MAPK- and PI3K-promoted tumorigenesis is also unknown. Thus, whether RASAL1 is truly a major tumor suppressor that plays an important role in human tumorigenesis has not been definitively established.

Our in vitro and in vivo data, at various levels, establish RASAL1 as a true TSG and, in particular, a major TSG in thyroid cancer. The evidence to support this conclusion includes the following: 1) RASAL1 inhibited both in vitro thyroid cancer cell growth and in vivo thyroid tumor growth; 2) RASAL1 was commonly hypermethylated in the 5' region in thyroid cancers, causing its silencing in thyroid cancer cells; 3) nonrecurrent impairing mutations were identified in the RAS GTPase-activating domain of RASAL1; and 4) RASAL1 mutations and hypermethylation were mutually exclusive, suggesting equal importance of either genetic or epigenetic inactivation of this gene. These characteristics of RASAL1 fully meet the classical criteria of TSG. Moreover, the ability of RASAL1 to suppress both RAS-coupled MAPK and PI3K pathways when there was no classical genetic alteration in the two pathways and the mutual exclusivity of the inactivating genetic and epigenetic alterations of RASAL1 with the classical mutations in these pathways also strongly support RASAL1 being an important TSG.

All our results on RASAL1 can be explained by its function as a classical RasGAP except for its inhibitory effect on C643 cell growth (FIG. 5). This cell harbors mutant H-RAS, which is constitutively activated and hence is independent of RASAL1 regulation in signaling through the MAPK and PI3K pathways (5); in fact, we found that introduction of RASAL1 had no effect on pERK and pAKT in C643 cells (FIG. 4). This raises the possibility that RASAL1 may be able to negatively regulate cell growth through an unidentified RAS-independent mechanism. This possibility is suggested by the case of NF1, another RasGAP, which could suppress cells through a RAS-independent mechanism (33-35).

MAPK and PI3K pathways play a fundamental role in thyroid tumorigenesis, in which the known classical genetic alterations in the two pathways, such as mutations in RAS, BRAF, PIK3CA, and PTEN, account for 65% to 70% of thyroid cancers (23). The inactivating genetic and epigenetic alterations of RASAL1 in the MAPK and PI3K pathways provide an alternative genetic background for thyroid cancers that do not harbor classical genetic alterations in the two pathways. It is interesting to note that hypermethylation and mutations of RASAL1 were particularly common in FTC and ATC but uncommon in PTC. Because the BRAF/MAPK pathway plays a fundamental role in the tumorigenesis of PTC (23, 36-38), whereas the PI3K/AKT pathway plays a fundamental role in FTC and ATC (26), it seems that impairment of RASAL1 may preferentially result in upregulation of the PI3K pathway over the MAPK pathway in thyroid tumorigenesis and promote the development of FTC and ATC over PTC. This possibility is consistent with the fact that in thyroid cancer RAS preferentially activates the PI3K pathway over the MAPK pathway (23). Although this study definitely establishes RASAL1 as a TSG in thyroid cancer, it is limited by leaving several issues undefined. For example, what is the mechanism of the RAS-independent function of RASAL1 in some cells such as C643 cells? What is the clinical implication of genetic and epigenetic findings of this study? Could germline genetic alterations of RASAL1, like those in other TSGs in the RAS pathway, exist and cause inherited cancer syndromes? These important questions need future studies to answer.

In summary, we provide strong evidence demonstrating that RASAL1 is a prominent TSG that is frequently inactivated by hypermethylation and mutations in thyroid cancer, particularly FTC and ATC. Impairment of RASAL1 is an alternative genetic background in thyroid cancers that do not harbor classical genetic alterations in the RAS-coupled MAPK and PI3K pathways.

TABLE 1

Mutations and Associated Sequence Motifs of RASAL1 in Thyroid Cancer

| Nucleotide Change* | Codon Change | Amino Acid Change | Exon of Location† | Sequence‡ | CpG | Direct Repeats |
|---|---|---|---|---|---|---|
| A1031G | AAC → AGC | N344S | Exon 13 | CGTTCTAACTCCCTG (SEQ ID NO: 1) | | |
| C1153T | CCC → TCC | P385S | Exon 14 | TGGATCCCTGCAAG (SEQ ID NO: 2) | | Yes |
| G1201A | GCA → ACA | A401T | Exon 14 | TCAAAGGCGCACTCTC (SEQ ID NO: 3) | Yes | Yes |
| C1303T | CCC → TCC | P435S | Exon 14 | CTGCCCGCCCGCCAT (SEQ ID NO: 4) | | Yes |
| C1312T | CGC → TGC | R438C | Exon 14 | GCCATGCGCCTCGCC (SEQ ID NO: 5) | Yes | Yes |
| G1313A | CGC → CAC | R438H | Exon 14 | GCCATGCGCCTCGCC (SEQ ID NO: 6) | Yes | Yes |
| C1422A | TTC → TTA | F474L | Exon 15 | CGATTCTTCGCACC (SEQ ID NO :7) | Yes | Yes |
| G1782A | TGG → TGA | W594X | Exon 17 | ACGTCTGGCTCAGCG (SEQ ID NO: 8) | | |

*Nucleotide number1 is defined as A of the ATG translation initiation codon (GeneBank Accession No. NM_004658 (SEQ ID NO: 85)).
†The exon structure is based on the RASAL1 cDNA sequence (GeneBank Accession No. NM_004658 (SEQ ID NO: 85)).
‡The mutated nucleotides are underlined and all the motif sequences containing the mutation are in italics. The direct repeat sequences are further italicized to distinguish them from the CpG motif. Only direct repeats with less than two nucleotides in-between are taken into account in this study. A single mutation could be classified into more than one specific sequence (e.g., CpG motif or direct repeat), because a mutation might be caused independently by more than one mechanism (40).

TABLE 2

Genotypes of Thyroid Cancer Cell Lines

| Cell line | Derived from | Genetic alterations | | | |
|---|---|---|---|---|---|
| | | RET Rearrangement | RAS | BRAF | PIK3CA or PTEN |
| WRO | FTC | — | — | — | |
| KAT18 | ATC | — | — | — | |
| Hth74 | ATC | — | — | — | |
| TPC1 | ATC | RET/PTC1 | — | — | |
| C643 | ATC | — | H-RAS(G13R$^{+/-}$) | — | |
| Hth7 | ATC | — | N-RAS (Q61R$^{+/-}$) | — | |
| FTC133 | FTC | — | — | — | PTEN (R130X$^{+/+}$) |
| OCUT1 | ATC | — | — | V600E$^{+/-}$ | PIK3CA (H1047R$^{+/+}$) |
| K1 | PTC | — | — | V600E$^{+/-}$ | PIK3CA (E542K$^{+/+}$) |
| BCPAP | PTC | — | — | V600E$^{+/+}$ | — |
| SW1736 | ATC | — | — | V600E$^{+/-}$ | — |

*$^{+/-}$heterozygous mutation; $^{+/+}$homozygous mutation; X: stop codon

TABLE 3

Sequence of PCR Primers

| Purpose | Oligo name | Sequence | | Product size (bp) |
|---|---|---|---|---|
| | | Forward | Reverse | |
| RT-PCR | RASAL1 | GTGGATGTGGATGGGGATGA (SEQ ID NO: 9) | TTCTTGCACTGGAGGTAGGT (SEQ ID NO: 10) | 326 |
| | DAB2IP | CATGGAGGAAGAGGTGGTCA (SEQ ID NO: 11) | AGGTACTTCTTCTTGGCTGG (SEQ ID NO: 12) | 246 |
| | NF1 | TGGCACTGCAAGCAAATGGA (SEQ ID NO: 13) | TAGGCCACGCTCTGTGTATT (SEQ ID NO: 14) | 209 |
| | SPRED1 | GATGACTCAAGTGGTGGATG (SEQ ID NO: 15) | CCTCTATCAAAAGCCCTAGC (SEQ ID NO: 16) | 271 |
| | SPRED2 | TCATCCATGGTGAACGACAG (SEQ ID NO: 17) | ATGGATGGTGGAAGATGACG (SEQ ID NO: 18) | 229 |
| | SPRY1 | TCCACTGATTGCCAGAACTC (SEQ ID NO: 19) | TTCTTGTCTTGGTGCTGTCC (SEQ ID NO: 20) | 248 |
| | SPRY2 | TTGGTGCAAAGCCGCGATCA (SEQ ID NO: 21) | TTGGTGTTTCGGATGGCTCT (SEQ ID NO: 22) | 212 |
| | RKIP | GCCCACCCAGGTTAAGAATA (SEQ ID NO: 23) | CTCGTAAACCAGCCAGACAT (SEQ ID NO: 24) | 253 |
| | DUSP5 | CTTCCTCAAAGGGGGATATG (SEQ ID NO: 25) | TCGCACTTGGATGCATGGTA (SEQ ID NO: 26) | 225 |
| | DUSP6 | AGCGACTGGAACGAGAATAC (SEQ ID NO: 27) | CGATGTCCGAGGAAGAGTCA (SEQ ID NO: 28) | 234 |
| | TSC1 | CAACAAGCAAATGTCGGGGA (SEQ ID NO: 29) | AGGATGGATAAACGAGTGGC (SEQ ID NO: 30) | 263 |
| | TSC2 | TGTTGGCTTGTCCTCGGAAT (SEQ ID NO: 31) | CAGGCAGTTGTAGCAGACCA (SEQ ID NO: 32) | 190 |
| | LKB1 | ATGGACACGTTCATCCACCG (SEQ ID NO: 33) | GCCGTAACCTCCTCAGTAGT (SEQ ID NO: 34) | 255 |
| MSP of RASAL1 | methylation | GTTTTTATTTGTAGAGTTCGGAC (SEQ ID NO: 35) | ATCCCAATACCGCCTATCCG (SEQ ID NO: 36) | 172 |
| | un-methylation | GGTTTTTATTTGTAGAGTTTGGAT (SEQ ID NO: 37) | AATCCCAATACCACCTATCCA (SEQ ID NO: 38) | 174 |
| Genomic DNA sequencing of RASAL1 | Exon 2 | TGAAGCAGGTGACATGTAGACG (SEQ ID NO: 39) | GGGCATCTGCTAACTCTAGGC (SEQ ID NO: 40) | 361 |
| | Exon 3 | TATTTCTATGGGTGGAAGCCC (SEQ ID NO: 41) | AATTCTTGGTCCCAGATTCCC (SEQ ID NO: 42) | 364 |
| | Exon 4 | GTGTCTGGGTCTCCAGGTGTC (SEQ ID NO: 43) | ACGTGAAGGTCTGAGTCAGGG (SEQ ID NO: 44) | 360 |
| | Exon 5 | CACCCAGACCTTGACACCTG (SEQ ID NO: 45) | TATGATAGCACCACCGCACTC (SEQ ID NO: 46) | 365 |
| | Exon 6 | CAACAGAACCAGACCCTGTG (SEQ ID NO: 47) | GGACTGAGGAGGTCCCAAAC (SEQ ID NO: 48) | 351 |
| | Exon 7 | GTTTGGACGGTCATGGTTAGG (SEQ ID NO: 49) | GGAAGCGAGTCTTCTTGATGG (SEQ ID NO: 50) | 367 |
| | Exon 8 | CAGAGCTTGGAGACCTCAGTG (SEQ ID NO: 51) | GCTGTACATCCACCCTTCTGA (SEQ ID NO: 52) | 360 |
| | Exon 9 | CTGTTCTTCCAGGGCTAGGTG (SEQ ID NO: 53) | GGTGAACGGGTGTAAAGTAAC (SEQ ID NO: 54) | 373 |

TABLE 3-continued

Sequence of PCR Primers

| Purpose | Oligo name | Sequence Forward | Reverse | Product size (bp) |
|---|---|---|---|---|
| | Exon10-11 | ATCGTGTTCGGCCAGATCTT (SEQ ID NO: 55) | TCCTGCAAGCCCACCATTGA (SEQ ID NO: 56) | 521 |
| | Exon12-13 | GTTCAGCTCCCTAAATCCCA (SEQ ID NO: 57) | AGGTCAGGGTCCTCAGGCTT (SEQ ID NO: 58) | 538 |
| | Exon 14 | AAGATGAGTCCTCTCGGAGC (SEQ ID NO: 59) | CAGTTCTGTCCTGACTCCTC (SEQ ID NO: 60) | 368 |
| | Exon 15 | TGTGGCTTCCTGGTCAATTC (SEQ ID NO: 61) | GCTCTGCTCCTACCATGCTT (SEQ ID NO: 62) | 335 |
| | Exon 16 | TGCCCGGCAATATGAGTCTT (SEQ ID NO: 63) | GAAGTCCCTGAGTGGTGTCT (SEQ ID NO: 64) | 318 |
| | Exon 17 | CTAGGGAGCAGAGAACCAT (SEQ ID NO: 65) | ACAAAGAGGCAGCACACTGA (SEQ ID NO: 66) | 357 |
| | Exon 18 | ATGGACGAGCACACAGAGCA (SEQ ID NO: 67) | CCATCGCGGTGGGGTCTCA (SEQ ID NO: 68) | 306 |
| | Exon 19 | AAGGTGAGACCCCACCGCGA (SEQ ID NO: 69) | CCACGAGATAGGCACTGTTA (SEQ ID NO: 70) | 385 |
| | Exon20 | AGTAGTAGGTTTGAGGAGGG (SEQ ID NO: 71) | ATCCACCAACACACATGGGA (SEQ ID NO: 72) | 350 |
| | Exon21 | GTGATGGTGATGGTTCAGGA (SEQ ID NO: 73) | TGGGCTCAAGCAATTCTCA (SEQ ID NO: 74) | 396 |
| | Exon22 | AGCATGAGAAACCATTGGGTC (SEQ ID NO: 75) | GACTAGGCACGTCTCTGGGAG (SEQ ID NO: 76) | 358 |
| Mutagenesis for RASAL1 | N3445 | CCCTCTTCCGTTCTAgCTCCCTG GCATCC (SEQ ID NO: 77) | GGATGCCAGGGAGcTAGAACG GAAGAGGG (SEQ ID NO: 78) | |
| | P385S | ACATGGAGCTGGATTCCTGCAA GATGGACC (SEQ ID NO: 79) | GGTCCATCTTGCAGGAATCCA GCTCCATGT (SEQ ID NO: 80) | |
| | R438C | CCGCCCGCCATGtGCCTCGCCTT CA (SEQ ID NO: 81) | TGAAGGCGAGGCaCATGGCGG GCGG (SEQ ID NO: 82) | |
| | P474L | CTCTTCTTGCGATTCTTAGCAC CTGCCATCC (SEQ ID NO: 83) | GGATGGCAGGTGCTAAGAATC GCAAGAAGAG (SEQ ID NO: 84) | |

TABLE 4

Alterations of Genes in the RAS Signaling Pathway in 101 Cases of Thyroid Tumor

| | | RASAL1 | | PIK3CA | | PTEN | N-RAS | K-RAS | BRAF |
|---|---|---|---|---|---|---|---|---|---|
| Case | Type | Mutation (amino acid substitution)*† | Methylation level | Mutation | Amplification | mutation | mutation | mutation | mutation |
| 1 | PTC | WT | 0 | WT | No | WT | WT | WT | WT |
| 2 | PTC | WT | 0 | WT | No | WT | Q61R | WT | WT |
| 3 | PTC | WT | 0 | WT | No | WT | WT | WT | V600E |
| 4 | PTC | WT | 0 | S553N | No | WT | WT | WT | V600E |
| 5 | PTC | WT | 0 | WT | No | WT | WT | WT | WT |
| 6 | PTC | WT | 0 | WT | No | WT | WT | WT | V600E |
| 7 | PTC | WT | 0 | I1062V | No | WT | WT | WT | V600E |
| 8 | PTC | WT | 0 | WT | No | WT | WT | WT | V600E |
| 9 | PTC | WT | 0 | WT | Yes | WT | WT | WT | V600E |
| 10 | PTC | WT | 0 | WT | No | WT | WT | WT | V600E |
| 11 | PTC | WT | 11.39 | F1039L | No | WT | WT | WT | WT |
| 12 | PTC | WT | 0 | WT | No | WT | WT | WT | WT |
| 13 | PTC | WT | 0 | WT | No | WT | WT | WT | WT |
| 14 | PTC | WT | 0 | WT | No | WT | WT | WT | WT |
| 15 | PTC | WT | 0 | WT | No | WT | WT | WT | V600E |
| 16 | PTC | WT | 0 | WT | No | WT | WT | WT | V600E |
| 17 | PTC | WT | 0 | WT | No | WT | WT | WT | V600E |
| 18 | PTC | WT | 0 | WT | No | WT | WT | WT | WT |
| 19 | PTC | WT | 0 | WT | No | WT | Q61R | WT | WT |
| 20 | PTC | WT | 0 | WT | No | WT | WT | WT | WT |
| 21 | PTC | WT | 0 | WT | No | WT | WT | WT | WT |
| 22 | PTC | C1312T (R438C) | 0 | WT | No | WT | WT | WT | WT |
| 23 | PTC | WT | 0 | WT | Yes | R142Q | WT | WT | V600E |
| 24 | PTC | WT | 0 | WT | No | WT | WT | WT | V600E |
| 25 | PTC | WT | 0 | WT | No | WT | WT | WT | T1799-1801TG Adel |

TABLE 4-continued

Alterations of Genes in the RAS Signaling Pathway in 101 Cases of Thyroid Tumor

| | | RASAL1 | | PIK3CA | | PTEN | N-RAS | K-RAS | BRAF |
|---|---|---|---|---|---|---|---|---|---|
| Case | Type | Mutation (amino acid substitution)*† | Methylation level | Mutation | Amplification | mutation | mutation | mutation | mutation |
| 26‡ | PTC | WT | 0 | WT | N/A | WT | WT | WT | WT |
| 27‡ | PTC | WT | 0 | WT | N/A | WT | WT | WT | WT |
| 28‡ | PTC | WT | 0 | WT | N/A | WT | WT | WT | V600E |
| 29‡ | PTC | WT | 36.32 | WT | N/A | WT | WT | WT | WT |
| 30‡ | PTC | WT | 0 | WT | N/A | WT | WT | WT | WT |
| 31 | FTC | G1782A (W594X) | 27.66 | WT | Yes | WT | WT | WT | WT |
| 32 | FTC | WT | 0 | D520N | Yes | WT | WT | WT | WT |
| 33 | FTC | WT | 0 | WT | Yes | WT | WT | WT | WT |
| 34 | FTC | WT | 32.73 | WT | Yes | WT | Q61R | WT | WT |
| 35 | FTC | WT | 100 | WT | Yes | WT | WT | WT | WT |
| 36 | FTC | WT | 0 | WT | No | WT | Q61R | WT | WT |
| 37 | FTC | WT | 0 | WT | Yes | WT | WT | WT | WT |
| 38 | FTC | WT | 65.06 | WT | Yes | WT | WT | WT | WT |
| 39 | FTC | WT | 91.85 | WT | Yes | WT | WT | WT | WT |
| 40 | FTC | G1201A (A401T) | 0 | WT | Yes | WT | WT | WT | WT |
| 41 | FTC | WT | 100 | WT | Yes | WT | WT | WT | WT |
| 42 | FTC | WT | 58.57 | WT | No | WT | Q61R | WT | WT |
| 43 | FTC | WT | 52.68 | WT | No | WT | Q61R | WT | WT |
| 44 | FTC | WT | 0 | WT | Yes | WT | WT | WT | WT |
| 45 | FTC | WT | 33.58 | WT | Yes | WT | WT | WT | WT |
| 46 | FTC | WT | 70.19 | WT | No | WT | WT | WT | WT |
| 47 | FTC | WT | 0 | WT | Yes | WT | WT | WT | WT |
| 48 | FTC | WT | 0 | WT | Yes | WT | WT | WT | WT |
| 49 | FTC | WT | 0 | WT | No | WT | WT | WT | WT |
| 50 | FTC | WT | 0 | WT | No | WT | WT | WT | WT |
| 51 | FTC | WT | 0 | WT | No | WT | WT | WT | WT |
| 52 | FTC | WT | 0 | WT | No | WT | WT | WT | WT |
| 53 | FTC | WT | 0 | WT | Yes | WT | WT | WT | WT |
| 54 | FTC | WT | 30.57 | WT | Yes | WT | WT | WT | WT |
| 55 | FTC | WT | 0 | F506S | No | WT | WT | WT | WT |
| 56 | FTC | WT | 0 | WT | No | WT | Q61R | WT | WT |
| 57 | FTC | WT | 0 | WT | No | WT | WT | WT | WT |
| 58 | FTC | WT | 40.38 | WT | Yes | WT | WT | WT | WT |
| 59 | FTC | WT | 95.83 | WT | Yes | WT | WT | WT | WT |
| 60 | FTC | WT | 4.39 | WT | No | WT | WT | G12R | WT |
| 61 | FTC | WT | 0 | WT | No | WT | WT | WT | WT |
| 62 | FTC | WT | 7.49 | L1001I | No | WT | Q61R | WT | WT |
| 63 | FTC | WT | 16.97 | WT | No | WT | WT | WT | WT |
| 64 | FTC | WT | 0 | WT | No | WT | WT | WT | WT |
| 65 | FTC | WT | 37.49 | WT | No | WT | WT | WT | WT |
| 66 | FTC | WT | 18.48 | WT | No | WT | WT | WT | WT |
| 67 | FTC | WT | 53.84 | WT | No | WT | WT | WT | WT |
| 68‡ | FTC | WT | 31.66 | WT | N/A | WT | Q61R | WT | WT |
| 69‡ | FTC | WT | 96.97 | WT | N/A | WT | WT | WT | WT |
| 70‡ | FTC | WT | 80.28 | WT | N/A | WT | WT | WT | WT |
| 71‡ | FTC | WT | 0 | WT | N/A | WT | WT | WT | WT |
| 72‡ | ATC | WT | 90.00 | WT | N/A | WT | WT | WT | WT |
| 73‡ | ATC | G1313A (R438H)§ | 37.32 | WT | Yes | WT | WT | WT | V600E |
| 74 | ATC | WT | 0 | WT | Yes | WT | WT | WT | WT |
| 75 | ATC | WT | 30.91 | WT | Yes | WT | WT | WT | WT |
| 76 | ATC | WT | 0 | WT | Yes | WT | WT | WT | WT |
| 77 | ATC | WT | 0 | L1047L | No | WT | Q61R | WT | WT |
| 78 | ATC | WT | 13.81 | I1001L | Yes | WT | WT | WT | WT |
| 79 | ATC | WT | 0 | WT | Yes | WT | WT | WT | WT |
| 80 | ATC | WT | 0 | WT | No | WT | WT | WT | WT |
| 81 | ATC | WT | 0 | WT | No | WT | WT | WT | V600E |
| 82‡ | ATC | C1303T (P435S) | 0 | WT | Yes | WT | WT | WT | WT |
| 83 | ATC | WT | 0 | WT | No | WT | WT | WT | WT |
| 84 | ATC | WT | 0 | WT | Yes | WT | WT | WT | WT |
| 85 | ATC | WT | 0 | WT | Yes | WT | WT | WT | V600E |
| 86 | ATC | WT | 0 | WT | No | P226L | WT | WT | WT |
| 87‡ | ATC | A1031G (N344S) | 6.26 | WT | Yes | WT | WT | WT | WT |
| 88 | ATC | WT | 62.11 | WT | No | D162G, | WT | WT | V600E |
| 89 | ATC | WT | 0 | WT | No | WT | WT | WT | WT |
| 90 | ATC | WT | 96.32 | WT | No | WT | WT | WT | WT |

TABLE 4-continued

Alterations of Genes in the RAS Signaling Pathway in 101 Cases of Thyroid Tumor

| | | RASAL1 | | PIK3CA | | | | | |
| | | Mutation (amino acid | Methylation | | | PTEN | N-RAS | K-RAS | BRAF |
| Case | Type | substitution)*† | level | Mutation | Amplification | mutation | mutation | mutation | mutation |
|---|---|---|---|---|---|---|---|---|---|
| 91 | ATC | C1422A (F474L)§ | 8.35 | WT | No | WT | WT | WT | V600E |
| 92 | ATC | WT | 0 | WT | Yes | WT | WT | WT | V600E |
| 93 | ATC | C1153T (P385S) | 0 | WT | No | WT | WT | WT | WT |
| 94 | ATC | WT | 0 | WT | No | WT | Q61K | WT | WT |
| 95 | ATC | WT | 16.91 | WT | No | WT | WT | WT | WT |
| 96 | ATC | WT | 0 | WT | Yes | F154S | WT | WT | T1799A |
| 97 | ATC | WT | 100 | WT | No | WT | WT | WT | WT |
| 98 | ATC | WT | 4.11 | WT | No | WT | WT | WT | WT |
| 99 | ATC | WT | 10.22 | WT | No | WT | WT | WT | WT |
| 100 | ATC | WT | 100 | WT | No | WT | WT | WT | WT |
| 101 | ATC | WT | 3.25 | WT | No | WT | WT | WT | V600E |

*Nucleotide numbering is based on GeneBank accession no. NM_004658. Nucleotide number 1 is the A of the ATG-translation initiation codon.
†X means a stop codon
‡means that a matched normal thyroid sample of the patient was also examined for genetic alterations which were negative in the normal tissues.
§means homozygous mutation.
||No H-RAS mutation was detected in these thyroid samples and the results therefore was not listed in the table.

REFERENCES

1. Rebollo A, Martinez A. Ras proteins: recent advances and new functions. *Blood*. 1999; 94(9):2971-2980.
2. Vigil D, Cherfils J, Rossman K L, et al. Ras superfamily GEFs and GAPs: validated and tractable targets for cancer therapy? *Nat Rev Cancer*. 2010; 10(12):842-857.
3. Kolfschoten I G, van Leeuwen B, Berns K, et al. A genetic screen identifies PITX1 as a suppressor of RAS activity and tumorigenicity. *Cell*. 2005; 121(6):849-858.
4. Jin H, Wang X, Ying J, et al. Epigenetic silencing of a Ca(2+)-regulated Ras GTPase-activating protein RASAL defines a new mechanism of Ras activation in human cancers. *Proc Natl Acad Sci USA*. 2007; 104(30):12353-12358.
5. Ohta M, Seto M, Ijichi H, et al. Decreased expression of the RAS-GTPase activating protein RASAL1 is associated with colorectal tumor progression. *Gastroenterology*. 2009; 136(1):206-216.
6. Yohay K H. The genetic and molecular pathogenesis of NF1 and NF2. *Semin Pediatr Neurol*. 2006; 13(1):21-26.
7. Johannessen C M, Reczek E E, James M F, et al. The NF1 tumor suppressor critically regulates TSC2 and mTOR. *Proc Natl Acad Sci USA*. 2005; 102(24):8573-8578.
8. Viskochil D. Genetics of neurofibromatosis 1 and the NF1 gene. *J Child Neurol*. 2002; 17(8):562-570.
9. Wakioka T, Sasaki A, Kato R, et al. Spred is a Sprouty-related suppressor of Ras signalling. *Nature*. 2001; 412 (6847):647-651.
10. Sasaki A, Taketomi T, Wakioka T, et al. Identification of a dominant negative mutant of Sprouty that potentiates fibroblast growth factor but not epidermal growth factor-induced ERK activation. *J Biol Chem*. 2001; 276(39): 36804-36808.
11. Granovsky A E, Rosner M R. Raf kinase inhibitory protein: a signal transduction modulator and metastasis suppressor. *Cell Res*. 2008; 18(4):452-457.
12. Ueda K, Arakawa H, Nakamura Y. Dual-specificity phosphatase 5 (DUSP5) as a direct transcriptional target of tumor suppressor p53. *Oncogene*. 2003; 22(36):5586-5591.
13. Furukawa T, Sunamura M, Motoi F, et al. Potential tumor suppressive pathway involving DUSP6/MKP-3 in pancreatic cancer. *Am J Pathol*. 2003; 162(6):1807-1815.
14. Wrighton K H. Tumour suppressors: Role of nuclear PTEN revealed. *Nat Rev Cancer*. 2011; 11(3):154.
15. Hezel A F, Bardeesy N. LKB1; linking cell structure and tumor suppression. *Oncogene*. 2008; 27(55):6908-6919.
16. van Veelen W, Korsse S E, van de L L, et al. The long and winding road to rational treatment of cancer associated with LKB1/AMPK/TSC/mTORC1 signaling. *Oncogene*. 2011; 30(20):2289-2303.
17. Richter A M, Pfeifer G P, Dammann R H. The RASSF proteins in cancer; from epigenetic silencing to functional characterization. *Biochim Biophys Acta*. 2009; 1796(2): 114-128.
18. Bentires-Alj M, Kontaridis M I, Neel B G. Stops along the RAS pathway in human genetic disease. *Nat Med*. 2006; 12(3):283-285.
19. Brems H, Chmara M, Sahbatou M, et al. Germline loss-of-function mutations in SPRED1 cause a neurofibromatosis 1-like phenotype. *Nat Genet*. 2007; 39(9): 1120-1126.
20. Howlader N, Noone A M, Krapcho M, et al. SEER Cancer Statistics Review, 1975-2009 (Vintage 2009 Populations). http://seer.cancer.gov/csr/1975_2009_pops09. Accessed Aug. 13, 2013.
21. Jemal A, Bray F, Center M M, et al. Global cancer statistics. *CA Cancer J Clin*. 2011; 61(2):69-90.
22. Hundahl S A, Fleming I D, Fremgen A M, et al. A National Cancer Data Base report on 53,856 cases of thyroid carcinoma treated in the U.S., 1985-1995 [see comments]. *Cancer*. 1998; 83(12):2638-2648.
23. Xing M. Molecular pathogenesis and mechanisms of thyroid cancer. *Nat Rev Cancer*. 2013; 13(3):184-199.
24. Xing M. BRAF mutation in thyroid cancer. *Endocr Relat Cancer*. 2005; 12(2):245-262.
25. Xing M. BRAF mutation in papillary thyroid cancer: pathogenic role, molecular bases, and clinical implications. *Endocr Rev*. 2007; 28(7):742-762.
26. Xing M. Genetic alterations in the phosphatidylinositol-3 kinase/Akt pathway in thyroid cancer. *Thyroid*. 2010; 20(7):697-706.

27. Hou P, Liu D, Shan Y, et al. Genetic alterations and their relationship in the phosphatidylinositol 3-kinase/Akt pathway in thyroid cancer. Clin Cancer Res. 2007; 13(4): 1161-1170.
28. Liu D, Hou P, Liu Z, et al. Genetic alterations in the phosphoinositide 3-kinase/Akt signaling pathway confer sensitivity of thyroid cancer cells to therapeutic targeting of Akt and mammalian target of rapamycin. Cancer Res. 2009; 69(18):7311-7319.
29. Liu D, Hu S, Hou P, et al. Suppression of BRAF/MEK/MAP kinase pathway restores expression of iodide-metabolizing genes in thyroid cells expressing the V600E BRAF mutant. Clin Cancer Res. 2007; 13(4):1341-1349.
30. Hou P, Ji M, Xing M. Association of PTEN gene methylation with genetic alterations in the phosphatidylinositol 3-kinase/AKT signaling pathway in thyroid tumors. Cancer. 2008; 113(9):2440-2447.
31. Xing M, Cohen Y, Mambo E, et al. Early occurrence of RASSF1A hypermethylation and its mutual exclusion with BRAF mutation in thyroid tumorigenesis. Cancer Res. 2004; 64(5):1664-1668.
32. Ishizaka Y, Ushijima T, Sugimura T, et al. cDNA cloning and characterization of ret activated in a human papillary thyroid carcinoma cell line. Biochem Biophys Res Commun. 1990; 168(2):402-408.
33. Shapira S, Barkan B, Friedman E, et al. The tumor suppressor neurofibromin confers sensitivity to apoptosis by Ras-dependent and Rasindependent pathways. Cell Death Differ. 2007; 14(5):895-906.
34. Nur-E-Kamal M S, Varga M, Maruta H. The GTPase-activating NF1 fragment of 91 amino acids reverses v-Ha-Ras-induced malignant phenotype. J Biol Chem. 1993; 268(30):22331-22337.
35. Gutmann D H, Collins F S. The neurofibromatosis type 1 gene and its protein product, neurofibromin. Neuron. 1993; 10(3):335-343.
36. Nucera C, Porrello A, Antonello Z A, et al. B-Raf (V600E) and thrombospondin-1 promote thyroid cancer progression. Proc Natl Acad Sci USA. 2010; 107(23): 10649-10654.
37. Chakravarty D, Santos E, Ryder M, et al. Small-molecule MAPK inhibitors restore radioiodine incorporation in mouse thyroid cancers with conditional BRAF activation. J Clin Invest. 2011; 121(12):4700-4711.
38. Hu S, Liu D, Tufano R P, et al. Association of aberrant methylation of tumor suppressor genes with tumor aggressiveness and BRAF mutation in papillary thyroid cancer. Int J Cancer. 2006; 119(10):2322-2329.
39. Scheffzek K, Lautwein A, Kabsch W, et al. Crystal structure of the GTPase-activating domain of human p120GAP and implications for the interaction with Ras. Nature. 1996; 384(6609):591-596.
40. Todorova A, Danieli G A. Large majority of single-nucleotide mutations along the dystrophin gene can be explained by more than one mechanism of mutagenesis. Hum Mutat. 1997; 9(6):537-547.

I claim:

1. A method for predicting an increased risk of thyroid cancer in a human patient comprising the steps of:

(a) treating DNA isolated from a sample comprising thyroid cells collected from the patient using bisulfite;

(b) measuring the DNA methylation level of the promoter region of the RASAL1 gene from the bisulfite-treated DNA using methylation-specific polymerase chain reaction (MSP), wherein gel electrophoresis of the MSP amplification products creates a methylation and unmethylation band, wherein the MSP is performed using the methylation-specific primers shown in SEQ ID NOS:35-36;

(c) normalizing the measured DNA methylation level using an internal reference gene;

(d) calculating the percentage of allelic methylation using the formula [M/(M+U)]×100%, wherein M and U represent the density of the methylation and unmethylation band; and (e) predicting an increased risk of thyroid cancer in the patient if the percentage of allelic methylation is at least 50%.

2. The method of claim 1, wherein MSP is performed using the unmethylated primers shown in SEQ ID NOS: 37-38.

* * * * *